United States Patent

Morisawa et al.

[11] Patent Number: 5,364,844
[45] Date of Patent: Nov. 15, 1994

[54] RENIN-INHIBITORY OLIGOPEPTIDES, THEIR PREPARATION AND USE

[75] Inventors: Yasuhiro Morisawa; Mitsuru Kataoka; Yuichiro Yabe; Hiroyuki Koike; Yasuteru Iijima; Hidekuni Takahagi, all of Hiromachi; Tatsuo Kokubu, Ehimi; Kunio Hiwada, Ehime, all of Japan

[73] Assignee: Sankyo Company, Limited, Tokyo, Japan

[21] Appl. No.: 936,883

[22] Filed: Aug. 27, 1992

Related U.S. Application Data

[63] Continuation of Ser. No. 301,793, Jan. 25, 1989, abandoned.

[30] Foreign Application Priority Data

Jan. 26, 1988 [JP] Japan ................................. 63-15446
Aug. 22, 1988 [JP] Japan ................................ 63-207729

[51] Int. Cl.$^5$ ........................ A61K 37/02; C07K 5/06; C07K 5/08
[52] U.S. Cl. ........................................ 514/18; 514/19; 530/331; 548/180; 548/204; 548/205; 548/217; 548/236; 548/517; 548/527; 548/542; 548/561
[58] Field of Search ................ 530/331; 514/18, 19; 548/180, 344, 342, 336, 337, 217, 527, 517, 562, 561, 374, 375, 378, 205, 236, 327, 329, 330, 204

[56] References Cited

U.S. PATENT DOCUMENTS

| | | | |
|---|---|---|---|
| 4,424,207 | 1/1984 | Szelke et al. | 514/19 |
| 4,455,303 | 6/1984 | Burton | 514/19 |
| 4,548,926 | 10/1985 | Matsueda et al. | 514/19 |
| 4,560,505 | 12/1985 | Pinori et al. | 514/19 |
| 4,585,586 | 4/1986 | DiTrapani et al. | 514/19 |
| 4,645,759 | 2/1987 | Luly et al. | 514/19 |
| 4,650,661 | 3/1987 | Szelke | 514/19 |
| 4,652,551 | 3/1987 | Luly et al. | 514/19 |
| 4,657,931 | 4/1987 | Baran et al. | 514/19 |
| 4,665,055 | 5/1987 | Evans | 514/19 |
| 4,680,284 | 7/1987 | Luly et al. | 514/19 |
| 4,698,329 | 10/1987 | Matsueda et al. | 514/19 |

(List continued on next page.)

FOREIGN PATENT DOCUMENTS

| | | | |
|---|---|---|---|
| 0173481 | 3/1986 | European Pat. Off. | 514/19 |
| 0237202 | 9/1987 | European Pat. Off. | 514/19 |
| 0278158 | 8/1988 | European Pat. Off. | 514/19 |
| WO8704349 | 7/1987 | WIPO | 514/19 |

OTHER PUBLICATIONS

Wolff, *Burger's Medical Chemistry*, "Antihypertensive Agents", Fourth Edition, Part III, Wiley-Interscience, N.Y. 1981, pp. 288–289.

(List continued on next page.)

*Primary Examiner*—Lester L. Lee
*Attorney, Agent, or Firm*—Frishauf, Holtz, Goodman & Woodward

[57] ABSTRACT

Compounds of formula (I):

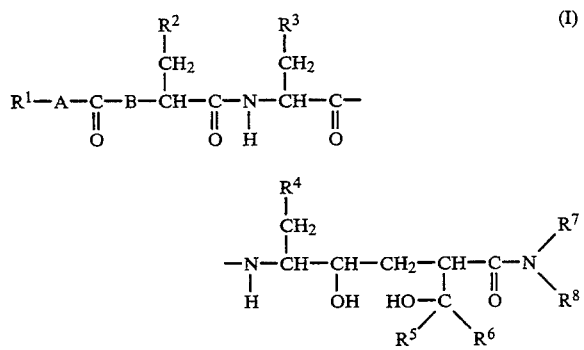

A is a carbon-carbon bond or $C_1$–$C_3$ alkylene; B is imino group or $C_1$–$C_2$ alkylene; $R^1$ is $C_1$–$C_4$ alkyl, $C_1$–$C_4$ alkoxy, heterocyclic or optionally substituted amino; $R^2$ is optionally substituted phenyl or optionally substituted naphthyl; $R^3$ is thiazolyl, isoxazolyl or imidazolyl; $R^4$ is isopropyl or cyclohexyl; $R^5$ and $R^6$ are $C_1$–$C_4$ alkyl, or, together with the carbon atom to which they are attached, $C_3$–$C_7$ cycloalkyl; $R^7$ is hydrogen, optionally substituted $C_1$–$C_6$ alkyl group; and $R^8$ is hydrogen or $C_1$–$C_4$ alkyl. These compounds have renin-inhibitory and, hence, hypotensive activities. The invention also provides a method for the treatment or prophylaxis of hypertension induced by failures in the renin-angiotensin system.

57 Claims, No Drawings

U.S. PATENT DOCUMENTS

| | | |
|---|---|---|
| 4,705,846 | 11/1987 | Thaisrivongs ............... 514/19 |
| 4,725,583 | 2/1988 | Luly et al. ............... 514/19 |
| 4,725,584 | 2/1988 | Luly et al. ............... 514/19 |
| 4,727,060 | 2/1988 | Bühlmayer et al. ............... 514/18 |
| 4,729,985 | 3/1988 | Kleinman et al. ............... 514/19 |
| 4,735,933 | 4/1988 | Hudspeth et al. ............... 514/19 |
| 4,743,585 | 5/1988 | Hudspeth et al. ............... 514/19 |
| 4,749,687 | 6/1988 | Bindra et al. ............... 514/19 |
| 4,758,584 | 7/1988 | Bühlmayer et al. ............... 514/400 |
| 4,804,743 | 2/1989 | Kaltenbronn et al. ............... 514/19 |
| 4,826,815 | 5/1989 | Luly et al. ............... 514/19 |
| 4,826,958 | 5/1989 | Sham ............... 530/331 |
| 4,857,507 | 8/1989 | Rosenberg et al. ............... 514/18 |
| 4,857,650 | 8/1989 | Iizuka et al. ............... 514/19 |
| 4,863,905 | 9/1989 | Hudspeth et al. ............... 514/19 |
| 4,864,017 | 9/1989 | Thairsrivongs ............... 530/329 |
| 4,877,785 | 10/1989 | Hanson et al. ............... 514/19 |
| 4,880,781 | 11/1989 | Hester, Jr. et al. ............... 514/19 |
| 4,882,420 | 11/1989 | Thaisrivongs ............... 514/19 |
| 4,885,292 | 12/1989 | Ryono et al. ............... 514/211 |
| 4,894,437 | 1/1990 | TenBrink ............... 514/19 |
| 4,895,834 | 1/1990 | Hudspeth et al. ............... 514/19 |
| 4,900,745 | 2/1990 | Hanson et al. ............... 514/19 |
| 4,900,746 | 2/1990 | Hanson et al. ............... 514/19 |
| 4,902,706 | 2/1990 | Hanson et al. ............... 514/19 |
| 4,904,660 | 2/1990 | Nakano et al. ............... 514/19 |
| 4,906,613 | 3/1990 | Watkins ............... 514/19 |
| 4,921,855 | 5/1990 | Hemmi et al. ............... 514/19 |
| 4,927,807 | 5/1990 | Stein et al. ............... 514/19 |
| 4,931,429 | 6/1990 | Hanson et al. ............... 514/19 |
| 4,977,141 | 12/1990 | Hanson et al. ............... 514/19 |
| 4,981,843 | 12/1991 | Ryono et al. ............... 514/19 |
| 4,994,477 | 2/1991 | Kempf et al. ............... 514/359 |
| 5,010,057 | 4/1991 | Henning et al. ............... 514/19 |
| 5,024,994 | 6/1991 | Doherty et al. ............... 514/19 |
| 5,036,051 | 7/1991 | Stein et al. ............... 514/19 |
| 5,036,053 | 7/1991 | Himmelsbach et al. ............... 514/19 |
| 5,036,054 | 7/1991 | Kaltenbronn et al. ............... 514/19 |
| 5,045,537 | 9/1991 | Weidmann ............... 514/19 |
| 5,059,589 | 10/1991 | Stein et al. ............... 514/19 |
| 5,063,207 | 11/1991 | Doherty et al. ............... 514/19 |
| 5,066,643 | 11/1991 | Abeles et al. ............... 514/19 |
| 5,071,837 | 12/1991 | Doherty et al. ............... 514/19 |
| 5,089,471 | 2/1992 | Hanson et al. ............... 514/19 |
| 5,095,006 | 3/1992 | Bender et al. ............... 514/19 |
| 5,098,924 | 3/1992 | Poss ............... 514/19 |
| 5,114,937 | 5/1992 | Hamby et al. ............... 514/19 |
| 5,122,514 | 6/1992 | Boger et al. ............... 514/19 |
| 5,147,888 | 9/1992 | Hanson et al. ............... 514/19 |
| 5,149,692 | 9/1992 | Doherty et al. ............... 514/19 |
| 5,171,751 | 12/1992 | Hanson et al. ............... 514/19 |
| 5,175,170 | 12/1992 | Hanson et al. ............... 514/19 |
| 5,175,181 | 12/1992 | Hanson et al. ............... 514/19 |
| 5,178,877 | 1/1993 | Garren et al. ............... 514/19 |
| 5,179,102 | 1/1993 | Hanson et al. ............... 514/19 |
| 5,180,725 | 1/1993 | Hanson et al. ............... 514/19 |
| 5,180,744 | 1/1993 | Hanson et al. ............... 514/19 |
| 5,198,426 | 3/1993 | Hamby et al. ............... 514/19 |
| 5,210,095 | 5/1993 | Hanson et al. ............... 514/19 |

OTHER PUBLICATIONS

Greenlec, Pharmaceutical Research, "Renin Inhibitors," vol. 4, No. 5, 1987, pp. 364–376.

Burger, *Medical Chemistry*, 1960 pp. 565–571, 578–581, 600–601.

Denkewalter et al. *Progress In Drug Research*, vol. 10, 1966, pp. 510–512.

Plattner et al. *J. Med. Chem.*, 1988, 31(12) pp. 2277–2288.

Kokubu et al., Biochemical Pharmacology, "Peptide Inhibitors of Renin Angiotensinogen Reaction System", vol. 22, pp. 3217–3223 (1973).

Repine et al., J. Med. Chem., "Renin Inhibitors Containing Esters at the $P_2$ Position. Oral Activity in Derivative of Methyl Aminomalonate," vol. 34, No. 7 (1991).

Burger, Medicinal Chemistry, 1960, pp. 565–571, 578–581, 600–601.

Denkewalter et al. Progess In Drug Research, 1967, vol. 10, pp. 510–512.

*Goodman and Gilman's The Pharmacological Basis of Therapeutics*, 1990, pp. 593–595.

"The Renin-Angiotensis System: Inhibitors and Antagonists", *The Handbook of Hypertension*, 1986, Hofbauer and Wood pp. 467–488.

Szelke M., Leckie B. J., Tree M., Brown A., Grant J., Hallett A., Hughes M., Jones D. M., Lever A. F. (1982) H–77: "A potent new renin inhibitor, in. vitro and in vivo studies", *Hypertension*, 4, Suppl. 2, 59.

Tree M., Atrash B., Donovon B., Gamble J., Hallett A., Hughes M., Jones D. M., Leckie B., Lever A. F., Morton J. J., Szelke M. (1983) "New Inhibitors of human renin tested in vitro and in vivo in the anaesthetized baboon," *J. Hypertension*, 1, 399.

"Renin Inhibitors", Kleinert et al, pp. 207–241, *Advance in Pharmacology*, 1991.

Journal Of Medicinal Chemistry, S. Thaisrivongs et al: "Renin inhibitors. Design of angiotensinogen transition-state analogues containing novel (2R, 3R, 4R, 5S)-5-amino-3,4-dihydroxy-2-isopropyl-7-methyloctanic acid", Jun. 1987, pp. 976–982.

RENIN-INHIBITORY OLIGOPEPTIDES, THEIR PREPARATION AND USE

This application is a continuation of application Ser. No. 07/301,793 filed Jan. 25, 1989 and now abandoned.

BACKGROUND TO THE INVENTION

The present invention relates to a series of new oligopeptides which have renin-inhibitory and, hence, hypotensive activities and thus are of particular value in the diagnosis and treatment of hypertension induced by failures in the renin-angiotensin system. The invention also relates to the preparation of such compounds and to their use in such treatment.

There is considerable evidence that reduction of elevated blood pressure reduces the risks of morbidity and mortality. Elevated blood pressure (hypertension) can be caused by a variety of factors and a large number of drugs is available for the treatment of hypertension, the drug of choice being dictated in large measure by the cause of the hypertension.

Angiotensin I is a polypeptide formed by the action of renin upon a plasma protein and is converted to angiotensin II by the action of ACE (angiotensin converting enzyme). Angiotensin II causes constriction of the arterioles and can produce hypertension. Hypertension of this type can be reduced by reducing the plasma concentration of angiotensin which, in turn, can be achieved by inhibiting the activity of renin. The number of available drugs having this type of inhibitory activity is very limited, and, to date, no such drug is commercially available. A variety of peptide derivatives having this type of activity is known. Those prior art compounds believed to be closest to the compounds of the present invention, are disclosed in European Patent Publications No. 184 550, 173 481, 236 734 and 278 158.

A serious disadvantage common to almost all of the known renin-inhibitory oligopeptides, including those mentioned in the previous paragraph, is that, in practice, it is necessary to administer them by parenteral routes, e.g. by injection, as suppositories or even by inhalation. This applies even in those cases where the compounds have been suggested for oral use, since it has subsequently been found that they either are insufficiently stable to enzymes, e.g. esterases, present in the digestive system or are inadequately absorbed from the stomach and/or intestines or both. Of course, this poor stability in the digestive system is expected with oligopeptides, as the mammalian digestive system is specifically designed to break down compounds of that type. Consequently, even if the compounds can be administered orally, such high doses are necessary in order to make up for poor absorption and/or losses caused by digestion as to make oral administration impractical.

It is, of course, well known that the oral route is the preferred route of administration, particularly where (as with the drugs with which the present invention is concerned) drugs are intended for self-administration by the patient, generally over a long period of time.

Hence, the inability of the known renin-inhibitory oligopeptides to be administered via the oral route is a serious disadvantage to their practical therapeutic use, despite what may appear their useful activities.

We have now discovered a series of peptide derivatives having a very marked ability to inhibit the activity of renin, which ability is believed to be significantly better than that of the prior art compounds. However, most significantly and surprisingly, the compounds of the invention have been found to have excellent absorptive properties (especially through the intestinal and digestive tracts) upon oral administration, quite contrary to what has been generally experienced with prior art oligopeptide compounds. Moreover, certain of the compounds of the invention have additionally and unexpectedly demonstrated very good stability on oral administration (i.e. they are stable to digestive enzymes, e.g. esterases).

These unexpected properties render the compounds of the invention especially suited to oral administration, as well, of course, as to the more traditional parenteral routes of administration.

The compounds of the invention are peptides, which may be represented by the general formula (I):

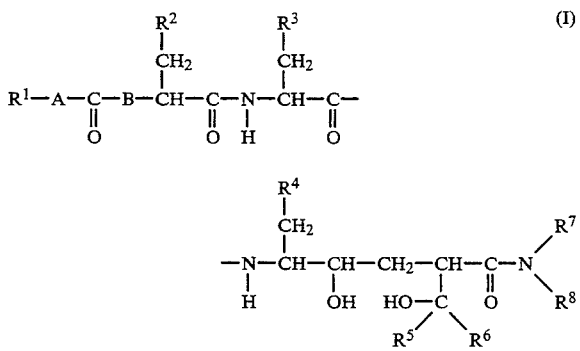

in which:

A represents a single carbon-carbon bond or an alkylene group containing from 1 to 3 carbon atoms;

B represents an imino group or an alkylene group containing 1 or 2 carbon atoms;

$R^1$ represents a $C_1$-$C_4$ alkyl group, a $C_1$-$C_4$ alkoxy group, a heterocyclic group or a group of formula (II):

in which:

$R^9$ and $R^{10}$ are independently selected from the group consisting of hydrogen atoms, $C_1$-$C_4$ alkyl groups, phenyl groups, substituted phenyl groups having at least one substituent selected from the group consisting of substituents (a), defined below, aralkyl groups, substituted aralkyl groups having at least one substituent selected from the group consisting of substituents (a), defined below, and $C_3$-$C_7$ cycloalkyl groups;

$R^2$ represents a phenyl group, a substituted phenyl group having at least one substituent selected from the group consisting of substituents (a), defined below, a naphthyl group or a substituted naphthyl group having at least one substituent selected from the group consisting of substituents (a), defined below;

$R^3$ represents a thiazolyl group, an isoxazolyl group or an imidazolyl group;

$R^4$ represents an isopropyl group or a cyclohexyl group;

$R^5$ and $R^6$ are independently selected from the group consisting of $C_1$–$C_4$ alkyl groups, or, together with the carbon atom to which they are attached, form a $C_3$–$C_7$ cycloalkyl group;

$R^7$ represents a hydrogen atom, a $C_1$–$C_6$ alkyl group, or a substituted $C_1$–$C_6$ alkyl group in which the substituent is selected from the group consisting of heterocyclic groups and hydroxy groups; and $R^8$ represents a hydrogen atom or a $C_1$–$C_4$ alkyl group;

said heterocyclic groups have 5 or 6 ring atoms, of which 1 or 2 are nitrogen hetero-atoms and 0 or 1 is an additional hereto-atom selected from the group consisting of sulfur and oxygen hetero-atoms, and being unsubstituted or having at least one substituent selected from the group consisting of substituents (b), defined below;

said aralkyl groups are $C_1$–$C_4$ alkyl groups having a phenyl or naphthyl substituent;

substituents (a):

$C_1$–$C_4$ alkyl groups, halogen atoms, hydroxy groups, trifluoromethyl groups and $C_1$–$C_4$ alkoxy groups;

substituents (b):

double bonded oxygen atoms (i.e. to form an oxo group), $C_1$–$C_4$ alkyl groups, $C_7$–$C_{10}$ aralkyl groups, substituted $C_7$–$C_{10}$ aralkyl groups having at least one substituent selected from the group consisting of substituents (a), defined above, phenyl groups, substituted phenyl groups having at least one substituent selected from the group consisting of substituents (a), defined above, pyridyl groups, formyl groups, $C_2$–$C_5$ alkylcarbonyl groups, $C_2$–$C_5$ alkoxycarbonyl groups and $C_8$–$C_{11}$ aralkyloxycarbonyl groups;

and pharmaceutically acceptable salts thereof.

The invention also provides a method for the treatment or prophylaxis of angiotensin-induced hypertension in an animal, especially a mammal, which may be human or non-human, by the administration thereto of a compound of formula (I) or a pharmaceutically acceptable salt thereof.

The invention also provides a composition for the treatment of angiotensin-induced hypertension in an animal, especially a mammal, which may be human or non-human, which comprises a compound of formula (I) or a pharmaceutically acceptable salt thereof in admixture with a pharmaceutically acceptable carrier or diluent.

The compounds of the invention may be prepared by reacting together two compounds, one having a terminal carboxy group or reactive derivative thereof and the other having a terminal amino group or reactive derivative thereof, under conditions conventional for peptide synthesis, said two compounds corresponding to the fragments derivable by cleavage of any one of the peptide bonds in said compound of formula (I). Preferred methods of preparing the compounds are described in greater detail hereafter.

DETAILED DESCRIPTION OF INVENTION

In the compounds of the present invention, A represents a single carbon-carbon bond or an alkylene group containing from 1 to 3 carbon atoms. The alkylene group may be a straight or branched chain group, and, in the case of the branched chain groups, the two "free" valences may be attached to the same carbon atom or to different carbon atoms. Where these "free" valences are attached to the same carbon atom, the groups are sometimes referred to as "alkylidene" groups. Examples of such groups include the methylene, ethylene, ethylidene and trimethylene groups. Of these, a single carbon-carbon bond, or a methylene group is preferred.

B represents an imino group or an alkylene group, which may be as defined in relation to the alkylene group represented by A, but which contains 1 or 2 carbon atoms such as, for example, a methylene or ethylene group. However, an imino group or a methylene group is preferred.

Where $R^1$, $R^5$, $R^6$, $R^8$, $R^9$, $R^{10}$, or substituent (a) or (b) represents a $C_1$–$C_4$ alkyl group, this may be a straight or branched chain alkyl group containing from 1 to 4 carbon atoms, and examples include the methyl, ethyl, propyl, isopropyl, butyl, isobutyl, sec-butyl and t-butyl groups. In the case of $R^1$, the methyl, ethyl, isopropyl and t-butyl groups are preferred, the t-butyl group being most preferred. In the case of $R^5$ and $R^6$, the methyl and ethyl groups are preferred, the methyl group being most preferred. In the case of $R^8$, the methyl and butyl groups are preferred (where $R^7$ represents a hydrogen atom), but it is more preferred that $R^8$ should be a hydrogen atom (where $R^7$ represents one of the alkyl groups defined above). In the case of $R^9$ and $R^{10}$, the methyl and ethyl groups are preferred, the methyl group being most preferred.

Where $R^1$ or substituent (a) represents a $C_1$–$C_4$ alkoxy group, this may be a straight or branched chain alkoxy group containing from 1 to 4 carbon atoms, and examples include the methoxy, ethoxy, propoxy, isopropoxy, butoxy, isobutoxy, sec-butoxy and t-butoxy groups, of which the t-butoxy group is preferred, in the case of $R^1$.

Where $R^1$ represents a heterocyclic group or the substituent on the alkyl group represented by $R^7$ is a heterocyclic group, this has either 5 or 6 ring atoms, of which 1 or 2 are nitrogen atoms and optionally 1 is a further hetero-atom selected from the group consisting of oxygen and sulfur hereto-atoms, the remainder, of course, being carbon atoms. These heterocyclic groups are preferably non-aromatic groups. Preferred examples of such groups include the piperidyl (especially piperidino), pyrrolidinyl (especially 1-pyrrolidinyl), morpholinyl (especially morpholino), thiomorpholinyl (especially thiomorpholino), oxazolidinyl, isoxazolidinyl, thiazolidinyl, imidazolidinyl and piperazinyl groups. Such groups may be unsubstituted or may have at least one substituent selected from the group consisting of substituents (b), defined above, preferably: an oxo group, for example, to form a 2-oxopyrrolidinyl or 2-oxomorpholinyl group; a $C_1$–$C_4$ alkyl group (e.g. as exemplified below in relation to such groups which may be represented by $R^7$); a phenyl group which may optionally be substituted with a halogen atom, a $C_1$–$C_4$ alkyl or a $C_1$–$C_4$ alkoxy group; a pyridyl group; an aralkyl group, as generally defined herein, such as a benzyl or phenethyl group; a $C_2$–$C_5$ alkoxycarbonyl group; a formyl group; a $C_2$–$C_5$ alkylcarbonyl group; or an aralkyloxycarbonyl group, in which the aralkyl part is as defined generally herein, such as a benzyloxycarbonyl, p-methoxybenzyloxycarbonyl or p-bromobenzyloxycarbonyl group. Of these substituents, we prefer an oxo group, a $C_1$–$C_4$ alkyl group, a phenyl group (which may optionally be substituted) or a pyridyl group. The more preferred heterocyclic groups are the morpholinyl groups (which may optionally be substituted with a methyl group), the thiomorpholinyl groups, the 2-oxopyrrolidinyl groups, and the piperazinyl groups (which may optionally be substituted with a methyl group or an optionally substituted phenyl group, in which the substituent is a methyl or methoxy group, or with a halogen atom).

Where aralkyl groups are referred to herein, these are groups in which the aryl part is a phenyl or naphthyl group; preferably a phenyl group, and the alkyl part is a $C_1$–$C_4$, preferably $C_1$–$C_3$, alkyl group, which may be a straight or branched chain group. The benzyl and phenethyl groups are preferred.

Where $R^5$ and $R^6$, together with the carbon atom to which they are attached, form a cycloalkyl group, this has from 3 to 7, preferably 5 or 6, ring carbon atoms, and examples include the cyclopropyl, cyclobutyl, cyclopentyl, cyclohexyl and cycloheptyl groups, but a cyclopentyl or cyclohexyl group is preferred and a cyclohexyl group is more preferred. Similarly, where $R^9$ and/or $R^{10}$ represents a cycloalkyl group, this may be any one of those exemplified above, the cyclohexyl group again being preferred.

Where $R^7$ represents an alkyl group, this may be a straight or branched chain alkyl group containing from 1 to 6 carbon atoms, and examples include the methyl, ethyl, propyl, isopropyl, butyl, isobutyl, sec-butyl, pentyl, isopentyl, 2-methylbutyl, hexyl, isohexyl and 2-methylpentyl groups.

Where $R^2$, $R^9$, $R^{10}$ or substituent (b) represents a phenyl group, $R^9$, $R^{10}$ or substituent (b) represents an aralkyl group or $R^2$ represents a naphthyl group, this may optionally be substituted. The substituent is selected from the group consisting of substituents (a), defined above, and examples include: the $C_1$–$C_4$ alkyl groups (e.g. the methyl, ethyl, propyl, isopropyl, butyl, isobutyl, sec-butyl and t-butyl groups); halogen atoms (such as the fluorine, chlorine, bromine and iodine atoms); the hydroxy group; the $C_1$–$C_4$ alkoxy groups (e.g. the methoxy, ethoxy, propoxy, isopropoxy, butoxy, isobutoxy, sec-butoxy and t-butoxy groups); and the trifluoromethyl group.

$R^3$ represents a thiazolyl group, an isoxazolyl group or an imidazolyl group, preferably a 4-thiazolyl group, a 5-isoxazolyl group or a 5-imidazolyl group, more preferably a 4-thiazolyl group or a 5-isoxazolyl group.

In preferred compounds of the present invention, A represents a single bond and B represents a methylene (—$CH_2$—) or ethylene (—$CH_2$—$CH_2$—) group; or A represents a methylene, ethylidene [—$CH(CH_3)$—] or trimethylene (—$CH_2$—$CH_2$—$CH_2$—) group and B represents an imino (—NH—) group.

Specific examples of preferred groups which may be represented by $R^1$ include the 1-pyrrolidinyl, piperidino, 2-methylpiperidino, 3-methylpiperidino, 4-methylpiperidino, 2-ethylpiperidino, 3-ethoxycarbonylpiperidino, 4-benzylpiperidino, morpholino, 2,6-dimethylmorpholino, perhydro-1,4-thiazin-4-yl (more commonly known as thiomorpholino), 4-methyl-1-piperazinyl, 4-benzyl-1-piperazinyl, 4-ethoxycarbonyl-1-piperazinyl, 4-phenyl-1-piperazinyl, 4-(1-pyridyl)-1-piperazinyl, 4-(2-pyridyl)-1-piperazinyl, 4-(3-pyridyl)-1-piperazinyl, 4-(4-pyridyl)-1-piperazinyl, 4-(p-fluorophenyl)-1-piperazinyl, 4-(p-chlorophenyl)-1-piperazinyl, 4-(o-chlorophenyl)-1-piperazinyl, 4-(m-chlorophenyl)-1-piperazinyl, 4-(o-methoxyphenyl)-1-piperazinyl, 4-(m-trifluoromethylphenyl)-1-piperazinyl, 2-pyrrolidinyl, 1-(t-butoxycarbonyl)-2-pyrrolidinyl, 1-benzyloxycarbonyl-2-pyrrolidinyl, amino, methylamino, ethylamino, propylamino, isopropylamino, dimethylamino, diethylamino, N-butyl-N-methylamino, dipropylamino, diisopropylamino, butylamino, isobutylamino, dibutylamino, diisobutylamino, benzylamino, phenethylamino, p-chlorophenethylamino, N-cyclohexyl-N-methylamino, N-benzyl-N-methylamino, N-benzyl-N-ethylamino, N-benzyl-N-isopropylamino, N-methyl-N-(p-tolyl)amino, methyl, ethyl, propyl, isopropyl, butyl, t-butyl, methoxy, ethoxy, propoxy, butoxy and t-butoxy groups.

Examples of preferred groups which may be represented by $R^2$ include the phenyl, p-tolyl, p-chlorophenyl, p-trifluoromethylphenyl, o-methoxyphenyl, m-methoxyphenyl, p-methoxyphenyl and 1-naphthyl groups.

Examples of preferred groups which may be represented by $R^5$ and $R^6$ include the methyl, ethyl, propyl, isopropyl, butyl and isobutyl groups. Alternatively, $R^5$ and $R^6$ may together represent a cycloalkane ring, in which case, they are preferably the cyclopentyl or cyclohexyl rings.

Examples of preferred groups which may be represented by $R^7$ include the 2-(1-pyrrolidinyl)ethyl, 2-(1-piperidyl)ethyl, 1-ethyl-3-piperidylmethyl, 4-piperidylmethyl, 1-benzyl-4-piperidylmethyl, 2-morpholinoethyl, 2-(2,6-dimethylmorpholino)ethyl, 2-thiomorpholinoethyl, 2-(1-methyl-2-pyrrolidinyl)ethyl, 1-ethyl-2-pyrrolidinylmethyl, 3-(2-oxo-1-pyrrolidinyl)propyl, 2-(4-methyl-1-piperazinyl)ethyl, 2-(4-ethoxycarbonyl-1-piperazinyl)ethyl, 2-[4-(2-pyridyl)-1-piperazinyl]ethyl, 2-(4-phenyl-1-piperazinyl)ethyl, 2-(4-benzyl-1-piperazinyl)ethyl, 3-morpholinopropyl, 3-(2-methyl-1-piperidyl)propyl, 2-(2-ethoxycarbonyl-1-pyrrolidinyl)ethyl, hydrogen, methyl, ethyl, propyl, isopropyl, butyl, isobutyl, sec-butyl, pentyl, isopentyl, 2-methylbutyl, 2-methylpentyl, hexyl, isohexyl and 1-(hydroxymethyl)-2-methylbutyl groups.

Examples of preferred groups which may be represented by $R^8$ include the hydrogen atom and the methyl, ethyl, propyl, isopropyl, butyl and isobutyl groups.

In the more preferred compounds of the present invention, A represents a single bond and B represents a methylene or imino group; or A represents a methylene or ethylidene group and B represents an imino group.

Examples of the more preferred groups which may be represented by $R^1$ include the 1-pyrrolidinyl, piperidino, morpholino, 2,6-dimethylmorpholino, thiomorpholino, 4-methyl-1-piperazinyl, 4-phenyl-1-piperazinyl, 4-benzylpiperidino, N-cyclohexyl-N-methylamino, N-benzyl-N-methylamino, N-butyl-N-methylamino, dimethylamino, diethylamino, methyl, ethyl, isopropyl, t-butyl and t-butoxy groups.

Examples of the more preferred groups which may be represented by $R^2$ include the phenyl, p-methoxyphenyl and 1-naphthyl groups.

Examples of the more preferred groups which may be represented by $R^5$ and $R^6$ or by $R^5$ and $R^6$, together with the carbon atom to which they are attached, include the methyl, ethyl, propyl, isopropyl, cyclopentyl and cyclohexyl groups.

Examples of the more preferred groups which may be represented by $R^7$ include the 2-(1-pyrrolidinyl)ethyl, 2-(1-piperidyl)ethyl, 3-morpholinopropyl, 2-morpholinoethyl, 3-(2-oxo-1-pyrrolidinyl)propyl, methyl, ethyl, propyl, isopropyl, butyl, isobutyl, pentyl, isopentyl, 2-methylbutyl, hexyl and 1-(hydroxymethyl)-2-methylbutyl groups.

Examples of the more preferred groups which may be represented by $R^8$ include the hydrogen atom and the methyl group.

The compounds of the present invention necessarily contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed, individual isomers may be prepared directly; on the other hand, if a mixture of isomers is prepared, the individual isomers may be obtained by conventional resolution techniques.

Of the various isomers of the compounds of the present invention, we especially prefer those in which:

the carbon atom indicated by an asterisk in the moiety of formula:

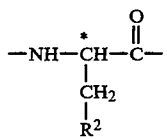

is in the S configuration;
those in which:
the carbon atom indicated by an asterisk in the moiety of formula:

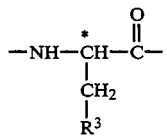

is in the S configuration;
those in which:
the carbon atom indicated by an asterisk in the moiety of formula:

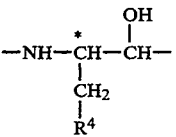

is in the S configuration;
those in which:
the carbon atom indicated by an asterisk in the moiety of formula:

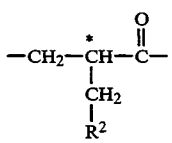

is in the R configuration;
those in which:
the carbon atom indicated by an asterisk in the moiety of formula:

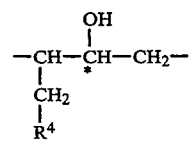

is in the S configuration; and
those in which:
the carbon atom indicated by an asterisk in the moiety of formula:

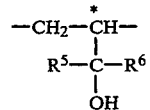

is in the S configuration.
More preferred isomers are those in which:
the carbon atoms indicated by an asterisk in the moiety of formula:

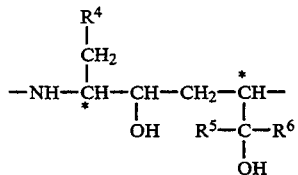

are all in the S configuration.

Still more preferably, all of the carbon atoms indicated by asterisks in formulae above are in the S configuration.

The compounds of the present invention can form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds include several basic nitrogen atoms and can, therefore, form acid addition salts. Examples of such acid addition salts include: salts with a mineral acid, such as hydrochloric acid, sulfuric acid or phosphoric acid; salts with an organic carboxylic acid, such as oxalic acid, maleic acid, succinic acid or citric acid; and salts with a sulfonic acid, such as methanesulfonic acid, benzenesulfonic acid or p-toluenesulfonic acid. Also, the compounds may contain a free carboxylic acid group, and, in such a case, can form salts with bases. Examples of such salts include: salts with an alkali metal or alkaline earth metal, such as sodium, potassium, calcium or magnesium; and organic base salts, such as a salt with dicyclohexylamine.

Preferred compounds of the present invention are those of formula (I) in which:

(1) A represents a single bond, and B represents a methylene group.

(2) A represents a methylene group or an ethylidene group, and B represents an imino group.

(3) $R^1$ represents a $C_1$-$C_4$ alkyl group, a $C_1$-$C_4$ alkoxy group, a non-aromatic heterocyclic group which is linked by a nitrogen atom, or a group of formula (II):

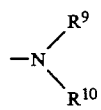

in which:

R⁹ and R¹⁰ are independently selected from the group consisting of $C_1$-$C_4$ alkyl groups, phenyl groups, aralkyl groups, and $C_3$-$C_7$ cycloalkyl groups;

and still more preferably a morpholinyl group, a thiomorpholinyl group, a pyrrolidinyl group, a piperidinyl group, a piperazinyl group having at least one substituent selected from the group consisting of $C_1$-$C_4$ alkyl groups, phenyl groups, substituted phenyl groups having at least one halogen or $C_1$-$C_4$alkoxy substituent and pyridyl groups, a di($C_1$-$C_4$alkyl)amino group, an N-($C_1$-$C_4$alkyl)-N-benzylamino group, an N-($C_1$-$C_4$ alkyl)-N-cyclohexylamino group.

(4) $R^2$ represents a phenyl group, a 4-methoxyphenyl group or a naphthyl group.

(5) $R^5$ and $R^6$ each represents a $C_1$-$C_4$ alkyl group, or, together with the carbon atom to which they are attached, represent a cyclopentyl group or a cyclohexyl group.

(6) $R^7$ represents a $C_1$-$C_6$ alkyl group, or a $C_1$-$C_6$ alkyl group which is substituted with a non-aromatic heterocyclic group having 5 or 6 ring atoms or with a hydroxy group and more preferably a $C_1$-$C_6$ alkyl group, a $C_2$-$C_4$ alkyl group which is substituted with a morpholino or 2-oxo-1-pyrrolidinyl group, or a $C_6$ alkyl group which is substituted with a hydroxy group.

(7) $R^8$ represents a hydrogen atom.

Still more preferred compounds of the present invention are those compounds of formula (I) in which:

A represents a single carbon-carbon bond and B represents a methylene group or A represents a methylene group and B represents an imino group;

$R^1$ represents a $C_1$-$C_4$ alkyl group, a heterocyclic group or a group of formula (IIa):

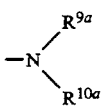

in which:

$R^{9a}$ and $R^{10a}$ are independently selected from the group consisting of $C_1$-$C_4$ alkyl groups, phenyl groups, $C_7$-$C_{10}$ aralkyl groups and $C_3$-$C_7$cycloalkyl groups;

$R^2$ represents a phenyl group, a substituted phenol group having at least one substituent selected from the group consisting of substituents (a), defined above, or a naphthyl group;

$R^3$ represents a thiazolyl group or an isoxazolyl group;

$R^4$ represents an isopropyl group or a cyclohexyl group;

$R^5$ and $R^6$ are independently selected from the group consisting of $C_1$-$C_4$ alkyl groups, or, together with the carbon atom to which they are attached, form a $C_5$ or $C_6$ cycloalkyl group;

$R^7$ represents a $C_1$-$C_6$ alkyl group, or a substituted $C_1$-$C_6$ alkyl group in which the substituent is selected from the group consisting of non-aromatic heterocyclic groups and hydroxy groups; and $R^8$ represents a hydrogen atom;

and pharmaceutically acceptable salts thereof.

The most preferred compounds of the present invention are those compounds of formula (I) in which:

A represents a single carbon-carbon bond and B represents a methylene group or A represents a methylene group and B represents an imino group;

$R^1$ represents a non-aromatic heterocyclic group or a group of formula (IIa), as defined above;

$R^2$ represents a phenyl group, a substituted phenyl group having at least one substituent selected from the group consisting of substituents (a), defined above, or a naphthyl group;

$R^3$ represents a thiazolyl group;

$R^4$ represents an isopropyl group or a cyclohexyl group;

$R^5$ and $R^6$ are independently selected from the group consisting of $C_1$-$C_4$ alkyl groups, or, together with the carbon atom to which they are attached, form a $C_5$ or $C_6$ cycloalkyl group;

$R^7$ represents a $C_1$-$C_6$ alkyl group; and $R^8$ represents a hydrogen atom;

and pharmaceutically acceptable salts thereof.

Examples of specific compounds of the invention are given in the following formulae (I-1) to (I-8), in which the substituents are as defined in the corresponding one of Tables 1 to 8 [i.e. Table 1 relates to formula (I-1), Table 2 relates to formula (I-2) and so on]. In the Tables, the following abbreviations are used:

| | |
|---|---|
| Bu | butyl |
| iBu | isobutyl |
| sBu | sec-butyl |
| tBu | t-butyl |
| Bz | benzyl |
| Et | ethyl |
| Hx | hexyl |
| cHx | cyclohexyl |
| Imid | imidazolyl |
| Isox | isoxazolyl |
| Me | methyl |
| Mor | morpholino |
| Mph | p-methoxyphenyl |
| Np | naphthyl |
| Ph | phenyl |
| Pip | piperidyl |
| Pn | pentyl |
| iPn | isopentyl |
| Pr | propyl |
| iPr | isopropyl |
| Pyrd | pyrrolidinyl |
| Thiz | thiazolyl |
| Thz | perhydro-1,4-thiazin-4-yl (= thiomorpholino) |

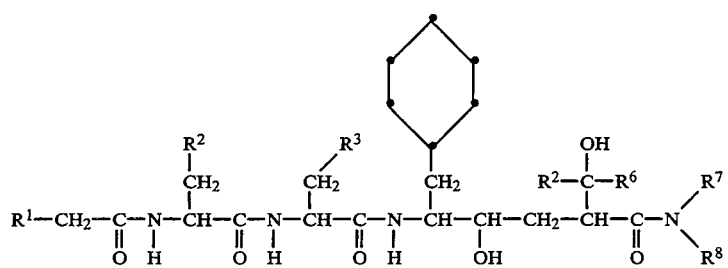
(I-1)
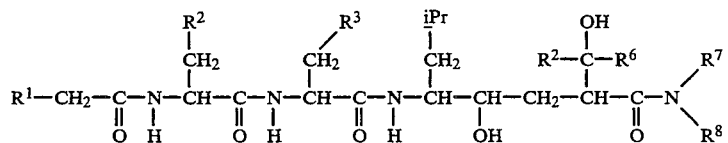
(I-2)
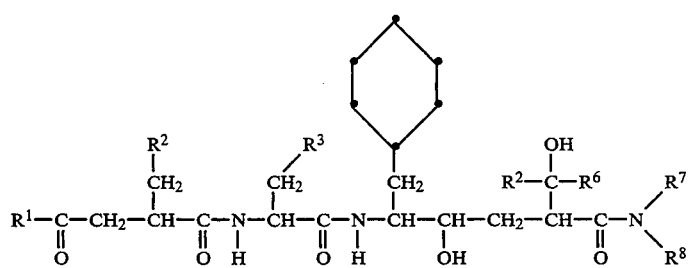
(I-3)
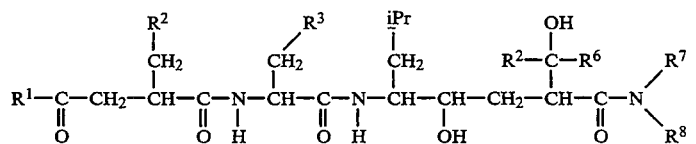
(I-4)
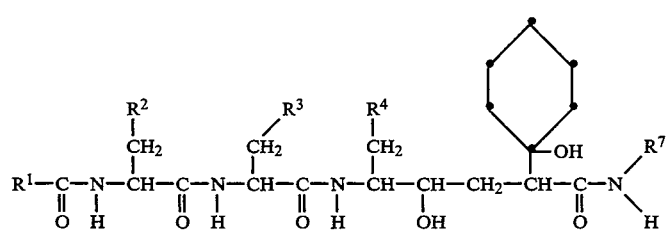
(I-5)
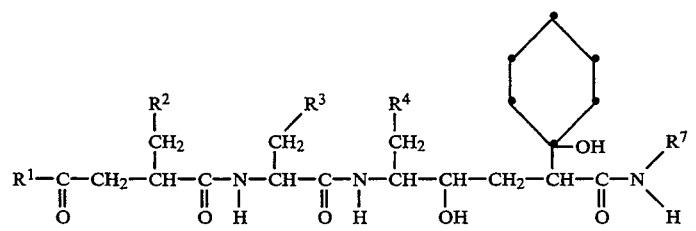
(I-6)
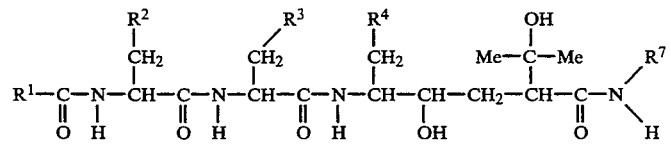
(I-7)

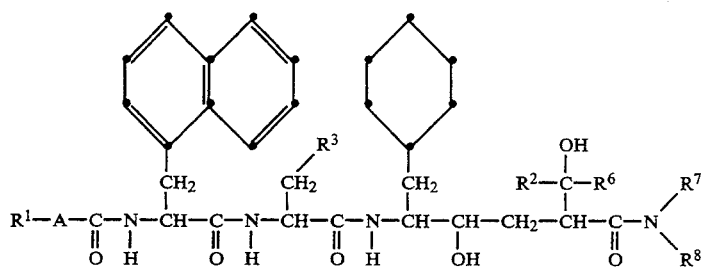

(I-8)

TABLE 1

| Cpd No | R¹ | R² | R³ | R⁵ | R⁶ | R⁷ | R⁸ |
|---|---|---|---|---|---|---|---|
| 1-1 | Mor | 1-Np | 4-Thiz | Me | Me | 2-MorEt | H |
| 1-2 | Mor | 1-Np | 4-Thiz | Me | Me | 3-(2-oxo--1-Pyrd)Pr | H |
| 1-3 | Mor | 1-Np | 4-Thiz | Me | Me | 2-(1-Pip)Et | H |
| 1-4 | Mor | 1-Np | 4-Thiz | Me | Me | Me | H |
| 1-5 | Mor | 1-Np | 4-Thiz | Me | Me | Bu | H |
| 1-6 | Mor | 1-Np | 4-Thiz | Me | Me | Pn | H |
| 1-7 | Mor | 1-Np | 4-Thiz | Me | Me | 2-MeBu | H |
| 1-8 | Mor | 1-Np | 4-Thiz | Me | Me | Hx | H |
| 1-9 | Mor | 1-Np | 4-Thiz | Et | Et | Bu | H |
| 1-10 | Mor | 1-Np | 5-Isox | Me | Me | 2-MorEt | H |
| 1-11 | Mor | 1-Np | 5-Isox | Me | Me | 2-(1-Pyrd)Et | H |
| 1-12 | Thz | 1-Np | 4-Thiz | Me | Me | Me | H |
| 1-13 | Mor | 1-Np | 5-Isox | Me | Me | iBu | H |
| 1-14 | Mor | 1-Np | 5-Isox | Me | Me | Hx | H |
| 1-15 | Mor | 1-Np | 5-Isox | Me | Me | Bu | Bu |
| 1-16 | 1-Pip | 1-Np | 4-Thiz | Me | Me | Me | H |
| 1-17 | Bz(Me)N- | 1-Np | 4-Thiz | Me | Me | Me | H |
| 1-18 | Bz(Me)N- | 1-Np | 4-Thiz | Me | Me | iBu | H |
| 1-19 | Bz(Me)N- | 1-Np | 4-Thiz | Me | Me | 2-MorEt | H |
| 1-20 | Ph(Me)N- | 1-Np | 4-Thiz | Me | Me | Me | H |
| 1-21 | 1-Pyrd | 1-Np | 4-Thiz | Me | Me | Me | H |
| 1-22 | cHx(Me)N- | 1-Np | 4-Thiz | Me | Me | 2-MorEt | H |
| 1-23 | cHx(Me)N- | 1-Np | 5-Isox | Me | Me | 3-(2-oxo--1-Pyrd)Pr | H |
| 1-24 | cHx(Me)N- | 1-Np | 5-Isox | Me | Me | Bu | H |
| 1-25 | Mor | 1-Np | 4-Thiz | Me | Me | 1-(HOMe)--2-MeBu | H |
| 1-26 | Mor | 1-Np | 5-Isox | Me | Me | Me | H |
| 1-27 | Mor | 1-Np | 5-Imid | Me | Me | Me | H |
| 1-28 | cHx(Me)N- | 1-Np | 4-Thiz | Me | Me | Me | H |
| 1-29 | Mor | Ph | 4-Thiz | Me | Me | Bu | H |
| 1-30 | Mor | Ph | 4-Thiz | Me | Me | 2-MorEt | H |
| 1-31 | Mor | Ph | 4-Thiz | Et | Et | Me | H |
| 1-32 | Bz(Me)N- | Ph | 4-Thiz | Me | Me | 2-MorEt | H |
| 1-33 | Bz(Me)N- | Ph | 4-Thiz | Me | Me | Bu | H |
| 1-34 | cHx(Me)N- | Ph | 4-Thiz | Me | Me | 2-MorEt | H |
| 1-35 | cHx(Me)N- | Ph | 4-Thiz | Me | Me | Bu | H |
| 1-36 | cHx(Me)N- | Ph | 5-Isox | Me | Me | Hx | H |
| 1-37 | Mor | Ph | 4-Thiz | Me | Me | Me | H |
| 1-38 | Mor | Ph | 5-Isox | Me | Me | Me | H |
| 1-39 | Mor | Ph | 5-Isox | Me | Me | Et | H |
| 1-40 | cHx(Me)N- | Ph | 4-Thiz | Me | Me | Me | H |
| 1-41 | Bz(Me)N- | Ph | 4-Thiz | Me | Me | Me | H |
| 1-42 | Mor | Mph | 4-Thiz | Me | Me | 2-MorEt | H |
| 1-43 | Mor | Mph | 5-Isox | Me | Me | Hx | H |
| 1-44 | Ph(Me)N- | Mph | 4-Thiz | Me | Me | Bu | H |
| 1-45 | cHx(Me)N- | Mph | 4-Thiz | Me | Me | Hx | H |
| 1-46 | cHx(Me)N- | Mph | 4-Thiz | Me | Me | 2-MorEt | H |
| 1-47 | Mor | Mph | 4-Thiz | Me | Me | Me | H |
| 1-48 | Mor | Ph | 4-Thiz | Me | Me | 2-MeBu | H |

TABLE 2

| Cpd No | R¹ | R² | R³ | R⁵ | R⁶ | R⁷ | R⁸ |
|---|---|---|---|---|---|---|---|
| 2-1 | Mor | 1-Np | 4-Thiz | Me | Me | Bu | H |
| 2-2 | Mor | 1-Np | 4-Thiz | Me | Me | 2-MorEt | H |
| 2-3 | Bz(Me)N- | 1-Np | 4-Thiz | Me | Me | 2-MorEt | H |
| 2-4 | Bz(Me)N- | 1-Np | 4-Thiz | Me | Me | Bu | H |
| 2-5 | cHx(Me)N- | 1-Np | 4-Thiz | Me | Me | 2-MorEt | H |
| 2-6 | cHx(Me)N- | 1-Np | 4-Thiz | Et | Et | Bu | H |
| 2-7 | Mor | 1-Np | 4-Thiz | Me | Me | Me | H |
| 2-8 | Mor | 1-Np | 4-Thiz | Me | Me | Et | H |
| 2-9 | Mor | 1-Np | 5-Isox | Me | Me | Me | H |
| 2-10 | Mor | Ph | 4-Thiz | Me | Me | Bu | H |
| 2-11 | Mor | Ph | 5-Isox | Me | Me | Hx | H |
| 2-12 | Bz(Me)N- | Ph | 4-Thiz | Me | Me | 2-MorEt | H |
| 2-13 | Bz(Me)N- | Ph | 4-Thiz | Me | Me | Bu | H |
| 2-14 | cHx(Me)N- | Ph | 4-Thiz | Me | Me | 2-MorEt | H |
| 2-15 | cHx(Me)N- | Ph | 4-Thiz | Me | Me | Bu | H |
| 2-16 | Mor | Ph | 4-Thiz | Me | Me | Me | H |

TABLE 3

| Cpd No | R¹ | R² | R³ | R⁵ | R⁶ | R⁷ | R⁸ |
|---|---|---|---|---|---|---|---|
| 3-1 | Mor | 1-Np | 4-Thiz | Me | Me | 2-MorEt | H |
| 3-2 | Mor | 1-Np | 4-Thiz | Me | Me | 3-(2-oxo-1-Pyrd)Pr | H |
| 3-3 | Mor | 1-Np | 4-Thiz | Me | Me | 2-(1-Pip)Et | H |
| 3-4 | Mor | 1-Np | 4-Thiz | Me | Me | Me | H |
| 3-5 | Mor | 1-Np | 4-Thiz | Me | Me | Et | H |
| 3-6 | Mor | 1-Np | 4-Thiz | Me | Me | Pr | H |
| 3-7 | Mor | 1-Np | 4-Thiz | Me | Me | Bu | H |
| 3-8 | Mor | 1-Np | 4-Thiz | Me | Me | 2-MeBu | H |
| 3-9 | Mor | 1-Np | 4-Thiz | Me | Me | Hx | H |
| 3-10 | Mor | 1-Np | 4-Thiz | Et | Et | iBu | H |
| 3-11 | Mor | 1-Np | 5-Isox | Me | Me | 2-MorEt | H |
| 3-12 | Mor | 1-Np | 5-Isox | Me | Me | 3-(2-oxo-1-Pyrd)Pr | H |
| 3-13 | Mor | 1-Np | 5-Isox | Me | Me | 2-(1-Pyrd)Et | H |
| 3-14 | Mor | 1-Np | 5-Isox | Me | Me | iBu | H |
| 3-15 | Mor | 1-Np | 5-Isox | Me | Me | 2-MeBu | H |
| 3-16 | Mor | 1-Np | 5-Isox | Me | Me | Hx | H |
| 3-17 | Mor | 1-Np | 5-Imid | Me | Me | iBu | H |
| 3-18 | Mor | 1-Np | 5-Imid | Me | Me | 2-MeBu | H |
| 3-19 | Mor | 1-Np | 5-Imid | Me | Me | Hx | H |
| 3-20 | Bz(Me)N- | 1-Np | 4-Thiz | Me | Me | iBu | H |
| 3-21 | Bz(Me)N- | 1-Np | 4-Thiz | Me | Me | Hx | H |
| 3-22 | Bz(Me)N- | 1-Np | 4-Thiz | Me | Me | 2-MorEt | H |
| 3-23 | cHx(Me)N- | 1-Np | 4-Thiz | Me | Me | iPr | H |
| 3-24 | cHx(Me)N- | 1-Np | 4-Thiz | Me | Me | 2-MorEt | H |
| 3-25 | cHx(Me)N- | 1-Np | 5-Isox | Me | Me | 3-(2-oxo-1-Pyrd)Pr | H |
| 3-26 | cHx(Me)N- | 1-Np | 5-Isox | Me | Me | Bu | H |
| 3-27 | cHx(Me)N- | 1-Np | 5-Imid | Me | Me | 2-MorEt | H |
| 3-28 | 1-Pip | 1-Np | 4-Thiz | Me | Me | Me | H |
| 3-29 | 1-Pyrd | 1-Np | 4-Thiz | Me | Me | Me | H |
| 3-30 | cHx(Me)N- | 1-Np | 4-Thiz | Me | Me | 3-(2-oxo-1-Pyrd)Pr | H |
| 3-31 | Thz | 1-Np | 4-Thiz | Me | Me | Me | H |
| 3-32 | Mor | 1-Np | 4-Thiz | Me | Me | 1-(HOMe)-2-MeBu | H |
| 3-33 | Mor | 1-Np | 4-Thiz | Me | Me | H | H |
| 3-34 | Mor | 1-Np | 4-Thiz | Et | Et | Me | H |
| 3-35 | Mor | 1-Np | 4-Thiz | Et | Et | Et | H |
| 3-36 | Mor | 1-Np | 5-Isox | Me | Me | H | H |
| 3-37 | Mor | 1-Np | 5-Isox | Me | Me | Me | H |
| 3-38 | Mor | 1-Np | 5-Isox | Me | Me | Et | H |
| 3-39 | Mor | 1-Np | 5-Isox | Me | Me | Me | Me |
| 3-40 | Mor | 1-Np | 5-Isox | Et | Et | Me | H |
| 3-41 | Thz | 1-Np | 5-Isox | Me | Me | Me | H |
| 3-42 | 1-Pip | 1-Np | 5-Isox | Me | Me | Me | H |
| 3-43 | Mor | 1-Np | 5-Imid | Me | Me | Me | H |

TABLE 3-continued

| Cpd No | R¹ | R² | R³ | R⁵ | R⁶ | R⁷ | R⁸ |
|---|---|---|---|---|---|---|---|
| 3-44 | Bz(Me)N- | 1-Np | 4-Thiz | Me | Me | Me | H |
| 3-45 | Bz(Me)N- | 1-Np | 5-Isox | Me | Me | Me | H |
| 3-46 | Bz(Me)N- | 1-Np | 5-Imid | Me | Me | Me | H |
| 3-47 | cHx(Me)N- | 1-Np | 4-Thiz | Me | Me | Me | H |
| 3-48 | cHx(Me)N- | 1-Np | 5-Isox | Me | Me | Me | H |
| 3-49 | cHx(Me)N- | 1-Np | 5-Isox | Et | Et | Me | H |
| 3-50 | cHx(Me)N- | 1-Np | 5-Imid | Me | Me | Me | H |
| 3-51 | Me | 1-Np | 4-Thiz | Me | Me | Me | H |
| 3-52 | Me | 1-Np | 5-Isox | Me | Me | Me | H |
| 3-53 | Me | 1-Np | 5-Imid | Me | Me | Me | H |
| 3-54 | Et | 1-Np | 4-Thiz | Me | Me | Me | H |
| 3-55 | Et | 1-Np | 5-Isox | Me | Me | Me | H |
| 3-56 | Et | 1-Np | 5-Imid | Me | Me | Me | H |
| 3-57 | iPr | 1-Np | 4-Thiz | Me | Me | Me | H |
| 3-58 | iPr | 1-Np | 5-Isox | Me | Me | Me | H |
| 3-59 | iPr | 1-Np | 5-Imid | Me | Me | Me | H |
| 3-60 | tBu | 1-Np | 4-Thiz | Me | Me | Me | H |
| 3-61 | tBu | 1-Np | 5-Isox | Me | Me | Me | H |
| 3-62 | tBu | 1-Np | 5-Imid | Me | Me | Me | H |
| 3-63 | Mor | Ph | 4-Thiz | Me | Me | Pr | H |
| 3-64 | Mor | Ph | 4-Thiz | Me | Me | Bu | H |
| 3-65 | Mor | Ph | 4-Thiz | Me | Me | iPn | H |
| 3-66 | Mor | Ph | 4-Thiz | Me | Me | 2-MeBu | H |
| 3-67 | Mor | Ph | 4-Thiz | Me | Me | Hx | H |
| 3-68 | Mor | Ph | 4-Thiz | Me | Me | 2-MorEt | H |
| 3-69 | Mor | Ph | 4-Thiz | Et | Et | Bu | H |
| 3-70 | Mor | Ph | 5-Isox | Me | Me | Me | H |
| 3-71 | Mor | Ph | 5-Isox | Me | Me | Hx | H |
| 3-72 | Mor | Ph | 5-Imid | Me | Me | 3-(2-oxo-1-Pyrd)Pr | H |
| 3-73 | Mor | Ph | 5-Imid | Me | Me | Hx | H |
| 3-74 | Bz(Me)N- | Ph | 4-Thiz | Me | Me | 2-MorEt | H |
| 3-75 | Bz(Me)N- | Ph | 4-Thiz | Me | Me | Bu | H |
| 3-76 | Bz(Me)N- | Ph | 4-Thiz | Me | Me | 2-MeBu | H |
| 3-77 | Bz(Me)N- | Ph | 5-Isox | Me | Me | Hx | H |
| 3-78 | Ph(Me)N- | Ph | 4-Thiz | Me | Me | Hx | H |
| 3-79 | cHx(Me)N- | Ph | 4-Thiz | Me | Me | 2-MorEt | H |
| 3-80 | cHx(Me)N- | Ph | 4-Thiz | Me | Me | Bu | H |
| 3-81 | cHx(Me)N- | Ph | 4-Thiz | Me | Me | Hx | H |
| 3-82 | cHx(Me)N- | Ph | 5-Isox | Me | Me | Hx | H |
| 3-83 | cHx(Me)N- | Ph | 5-Imid | Me | Me | 3-(2-oxo-1-Pyrd)Pr | H |
| 3-84 | Thz | Ph | 4-Thiz | Me | Me | Me | H |
| 3-85 | 1-Pip | Ph | 4-Thiz | Me | Me | Me | H |
| 3-86 | 1-Pyrd | Ph | 4-Thiz | Me | Me | Me | H |
| 3-87 | Mor | Ph | 4-Thiz | Me | Me | 1-(HOMe)-2-MeBu | H |
| 3-88 | Mor | Ph | 5-Isox | Me | Me | 1-(HOMe)-2-MeBu | H |
| 3-89 | Mor | Ph | 4-Thiz | Me | Me | H | H |
| 3-90 | Mor | Ph | 4-Thiz | Me | Me | Me | H |
| 3-91 | Mor | Ph | 4-Thiz | Me | Me | Et | H |
| 3-92 | Mor | Ph | 4-Thiz | Me | Me | iPr | H |
| 3-93 | Mor | Ph | 4-Thiz | Me | Me | iBu | H |
| 3-94 | Mor | Ph | 4-Thiz | Me | Me | sBu | H |
| 3-95 | Mor | Ph | 4-Thiz | Me | Me | Pn | H |
| 3-96 | Mor | Ph | 4-Thiz | Me | Me | Me | Me |
| 3-97 | Mor | Ph | 4-Thiz | Et | Et | Me | H |
| 3-98 | Mor | Ph | 4-Thiz | Et | Et | Et | H |
| 3-99 | Mor | Ph | 4-Thiz | Et | Et | iBu | H |
| 3-100 | Mor | Ph | 4-Thiz | Et | Et | 2-MeBu | H |
| 3-101 | Mor | Ph | 4-Thiz | Et | Et | 3-(2-oxo-1-Pyrd)Pr | H |
| 3-102 | Mor | Ph | 5-Isox | Me | Me | Me | H |
| 3-103 | Mor | Ph | 5-Isox | Me | Me | Et | H |
| 3-104 | Mor | Ph | 5-Isox | Et | Et | Me | H |
| 3-105 | Mor | Ph | 5-Isox | Et | Et | Bu | H |
| 3-106 | Mor | Ph | 5-Isox | Et | Et | 2-MorEt | H |
| 3-107 | Mor | Ph | 5-Imid | Me | Me | Me | H |
| 3-108 | Mor | Ph | 5-Imid | Me | Me | Et | H |
| 3-109 | Mor | Ph | 5-Imid | Me | Me | Bu | H |
| 3-110 | Mor | Ph | 5-Imid | Me | Me | 2-MeBu | H |
| 3-111 | Mor | Ph | 5-Imid | Me | Me | 2-MorEt | H |
| 3-112 | Bz(Me)N- | Ph | 4-Thiz | Me | Me | Me | H |
| 3-113 | Bz(Me)N- | Ph | 4-Thiz | Me | Me | Et | H |
| 3-114 | cHx(Me)N- | Ph | 4-Thiz | Me | Me | Me | H |
| 3-115 | cHx(Me)N- | Ph | 4-Thiz | Me | Me | Et | H |
| 3-116 | cHx(Me)N- | Ph | 4-Thiz | Et | Me | Me | H |
| 3-117 | cHx(Me)N- | Ph | 5-Isox | Me | Me | Me | H |
| 3-118 | Bz(Me)N- | Ph | 5-Imid | Me | Me | Me | H |
| 3-119 | cHx(Me)N- | Ph | 5-Imid | Me | Me | Me | H |
| 3-120 | Me | Ph | 4-Thiz | Me | Me | Me | H |
| 3-121 | Me | Ph | 4-Thiz | Me | Me | Et | H |
| 3-122 | Me | Ph | 4-Thiz | Et | Et | Me | H |
| 3-123 | Me | Ph | 4-Thiz | Me | Me | 2-MorEt | H |
| 3-124 | Me | Ph | 4-Thiz | Et | Et | Et | H |
| 3-125 | Me | Ph | 4-Thiz | Et | Et | 2-MeBu | H |
| 3-126 | Me | Ph | 4-Thiz | Et | Et | 2-MorEt | H |
| 3-127 | Me | Ph | 5-Isox | Me | Me | Me | H |
| 3-128 | Me | Ph | 5-Imid | Me | Me | Me | H |
| 3-129 | Et | Ph | 4-Thiz | Me | Me | Me | H |
| 3-130 | Et | Ph | 5-Isox | Me | Me | Me | H |
| 3-131 | Et | Ph | 5-Isox | Me | Me | Et | H |
| 3-132 | Et | Ph | 5-Imid | Me | Me | Me | H |
| 3-133 | iPr | Ph | 4-Thiz | Me | Me | Me | H |
| 3-134 | iPr | Ph | 5-Isox | Me | Me | Me | H |
| 3-135 | iPr | Ph | 5-Isox | Me | Me | 3-(2-oxo-1-Pyrd)Pr | H |
| 3-136 | tBu | Ph | 4-Thiz | Me | Me | Me | H |
| 3-137 | tBu | Ph | 4-Thiz | Me | Me | Et | H |
| 3-138 | tBu | Ph | 4-Thiz | Me | Me | 2-MorEt | H |
| 3-139 | tBu | Ph | 5-Isox | Me | Me | Me | H |
| 3-140 | tBu | Ph | 5-Isox | Me | Me | Et | H |
| 3-141 | tBu | Ph | 5-Isox | Me | Me | 3-(2-oxo-1-Pyrd)Pr | H |
| 3-142 | tBu | Ph | 5-Isox | Et | Et | Me | H |
| 3-143 | tBu | Ph | 5-Imid | Me | Me | Me | H |
| 3-144 | tBu | Ph | 5-Imid | Me | Me | Et | H |
| 3-45 | tBu | Ph | 5-Imid | Et | Et | Me | H |
| 3-146 | tBu | Ph | 5-Imid | Et | Et | 2-MorEt | H |
| 3-147 | Bu(Me)N- | Ph | 4-Thiz | Me | Me | Me | H |
| 3-148 | Et₂N- | Ph | 4-Thiz | Me | Me | Me | H |
| 3-149 | Mor | Mph | 4-Thiz | Me | Me | 2-MorEt | H |
| 3-150 | cHx(Me)N- | Mph | 4-Thiz | Me | Me | Hx | H |
| 3-151 | cHx(Me)N- | Mph | 5-Isox | Me | Me | Hx | H |
| 3-152 | Mor | Mph | 4-Thiz | Me | Me | Me | H |
| 3-153 | Mor | Mph | 4-Thiz | Me | Me | Et | H |
| 3-154 | Mor | Mph | 4-Thiz | Me | Me | Pr | H |
| 3-155 | Mor | Mph | 4-Thiz | Me | Me | Bu | H |
| 3-156 | Mor | Mph | 4-Thiz | Me | Me | 2-MeBu | H |
| 3-157 | Mor | Mph | 4-Thiz | Me | Me | Pn | H |
| 3-158 | Mor | Mph | 4-Thiz | Me | Me | 3-(2-oxo-1-Pyrd)Pr | H |
| 3-159 | Mor | Mph | 4-Thiz | Et | Et | Me | H |
| 3-160 | Mor | Mph | 4-Thiz | Et | Et | Et | H |
| 3-161 | Mor | Mph | 5-Isox | Me | Me | Me | H |
| 3-162 | Mor | Mph | 5-Isox | Me | Me | Et | H |
| 3-163 | Mor | Mph | 5-Isox | Me | Me | 2-MorEt | H |
| 3-164 | Mor | Mph | 5-Imid | Me | Me | Me | H |
| 3-165 | Mor | Mph | 5-Imid | Me | Me | Et | H |
| 3-166 | Mor | Mph | 5-Imid | Me | Me | 2-MeBu | H |
| 3-167 | Bz(Me)N- | Mph | 4-Thiz | Me | Me | Me | H |
| 3-168 | Bz(Me)N- | Mph | 5-Isox | Me | Me | Me | H |
| 3-169 | Bz(Me)N- | Mph | 5-Imid | Me | Me | Me | H |
| 3-170 | cHx(Me)N- | Mph | 4-Thiz | Me | Me | Me | H |
| 3-171 | cHx(Me)N- | Mph | 4-Thiz | Me | Me | Et | H |
| 3-172 | cHx(Me)N- | Mph | 5-Isox | Me | Me | Me | H |
| 3-173 | Me | Mph | 4-Thiz | Me | Me | Me | H |
| 3-174 | Me | Mph | 4-Thiz | Me | Me | sBu | H |
| 3-175 | Me | Mph | 4-Thiz | Me | Me | 2-MorEt | H |
| 3-176 | Me | Mph | 5-Isox | Me | Me | Me | H |
| 3-177 | Me | Mph | 5-Isox | Me | Me | 2-MorEt | H |
| 3-178 | Me | Mph | 5-Isox | Me | Me | 2-MorEt | H |
| 3-179 | Me | Mph | 5-Imid | Me | Me | Me | H |
| 3-180 | Et | Mph | 4-Thiz | Me | Me | Me | H |
| 3-181 | Et | Mph | 4-Thiz | Et | Et | Me | H |
| 3-182 | Et | Mph | 4-Thiz | Et | Et | 2-MorEt | H |
| 3-183 | Et | Mph | 5-Isox | Me | Me | Me | H |
| 3-184 | Et | Mph | 5-Imid | Me | Me | Me | H |
| 3-185 | iPr | Mph | 4-Thiz | Me | Me | Me | H |
| 3-186 | iPr | Mph | 4-Thiz | Me | Me | 2-MeBu | H |
| 3-187 | iPr | Mph | 4-Thiz | Me | Me | 2-MorEt | H |
| 3-188 | iPr | Mph | 5-Isox | Me | Me | Me | H |
| 3-189 | iPr | Mph | 5-Imid | Me | Me | Me | H |
| 3-190 | iPr | Mph | 5-Imid | Me | Me | 3-(2-oxo-1-Pyrd)Pr | H |
| 3-191 | tBu | Mph | 4-Thiz | Me | Me | Me | H |
| 3-192 | tBu | Mph | 4-Thiz | Me | Me | Et | H |
| 3-193 | tBu | Mph | 4-Thiz | Me | Me | Bu | H |
| 3-194 | tBu | Mph | 4-Thiz | Me | Me | 2-MeBu | H |

TABLE 3-continued

| Cpd No | R¹ | R² | R³ | R⁵ | R⁶ | R⁷ | R⁸ |
|---|---|---|---|---|---|---|---|
| 3-195 | tBu | Mph | 4-Thiz | Et | Et | Me | H |
| 3-196 | tBu | Mph | 4-Thiz | Et | Et | 2-MorEt | H |
| 3-197 | tBu | Mph | 5-Isox | Me | Me | Me | H |
| 3-198 | tBu | Mph | 5-Imid | Me | Me | Me | H |
| 3-199 | tBu | Mph | 5-Imid | Me | Me | 2-MeBu | H |
| 3-200 | tBu | Mph | 5-Imid | Et | Et | Me | H |
| 3-201 | tBu | Mph | 5-Imid | Et | Et | 2-MorEt | H |

TABLE 4

| Cpd No | R¹ | R² | R³ | R⁵ | R⁶ | R⁷ | R⁸ |
|---|---|---|---|---|---|---|---|
| 4-1 | Mor | 1-Np | 4-Thiz | Me | Me | Bu | H |
| 4-2 | Mor | 1-Np | 4-Thiz | Me | Me | 2-MeBu | H |
| 4-3 | Mor | 1-Np | 4-Thiz | Me | Me | 2-MorEt | H |
| 4-4 | Mor | 1-Np | 4-Thiz | Et | Et | Bu | H |
| 4-5 | Mor | 1-Np | 5-Isox | Me | Me | 2-MeBu | H |
| 4-6 | Mor | 1-Np | 5-Imid | Me | Me | 3-(2-oxo-1-Pyrd)Pr | H |
| 4-7 | Mor | 1-Np | 5-Imid | Me | Me | Hx | H |
| 4-8 | Bz(Me)N- | 1-Np | 4-Thiz | Me | Me | 2-MorEt | H |
| 4-9 | Bz(Me)N- | 1-Np | 4-Thiz | Me | Me | Bu | H |
| 4-10 | cHx(Me)N- | 1-Np | 4-Thiz | Me | Me | 2-MorEt | H |
| 4-11 | cHx(Me)N- | 1-Np | 4-Thiz | Me | Me | Bu | H |
| 4-12 | cHx(Me)N- | 1-Np | 5-Isox | Me | Me | Hx | H |
| 4-13 | Mor | 1-Np | 4-Thiz | Me | Me | Me | H |
| 4-14 | Mor | 1-Np | 4-Thiz | Me | Me | Et | H |
| 4-15 | Mor | 1-Np | 5-Isox | Me | Me | Me | H |
| 4-16 | Mor | 1-Np | 5-Isox | Me | Me | Et | H |
| 4-17 | Mor | 1-Np | 5-Isox | Et | Et | Me | H |
| 4-18 | Mor | 1-Np | 5-Imid | Me | Me | Me | H |
| 4-19 | Bz(Me)N- | 1-Np | 4-Thiz | Me | Me | Me | H |
| 4-20 | Bz(Me)N- | 1-Np | 5-Imid | Me | Me | Me | H |
| 4-21 | cHx(Me)N- | 1-Np | 4-Thiz | Me | Me | Me | H |
| 4-22 | cHx(Me)N- | 1-Np | 5-Isox | Me | Me | Me | H |
| 4-23 | cHx(Me)N- | 1-Np | 5-Imid | Me | Me | Me | H |
| 4-24 | Me | 1-Np | 4-Thiz | Me | Me | Me | H |
| 4-25 | Me | 1-Np | 5-Isox | Me | Me | Me | H |
| 4-26 | Et | 1-Np | 4-Thiz | Me | Me | Me | H |
| 4-27 | Et | 1-Np | 5-Isox | Me | Me | Me | H |
| 4-28 | Et | 1-Np | 5-Imid | Me | Me | Me | H |
| 4-29 | iPr | 1-Np | 4-Thiz | Me | Me | Me | H |
| 4-30 | iPr | 1-Np | 5-Isox | Me | Me | Me | H |
| 4-31 | tBu | 1-Np | 4-Thiz | Me | Me | Me | H |
| 4-32 | tBu | 1-Np | 5-Isox | Me | Me | Me | H |
| 4-33 | tBu | 1-Np | 5-Imid | Me | Me | Me | H |
| 4-34 | Mor | Ph | 4-Thiz | Me | Me | Bu | H |
| 4-35 | Mor | Ph | 4-Thiz | Me | Me | Hx | H |
| 4-36 | Mor | Ph | 4-Thiz | Me | Me | 2-MorEt | H |
| 4-37 | Mor | Ph | 4-Thiz | Me | Me | 3-(2-oxo-1-Pyrd)Pr | H |
| 4-38 | Mor | Ph | 4-Thiz | Et | Et | Bu | H |
| 4-39 | Bz(Me)N- | Ph | 4-Thiz | Me | Me | Bu | H |
| 4-40 | Ph(Me)N- | Ph | 4-Thiz | Me | Me | Hx | H |
| 4-41 | cHx(Me)N- | Ph | 4-Thiz | Me | Me | Hx | H |
| 4-42 | cHx(Me)N- | Ph | 5-Isox | Me | Me | Hx | H |
| 4-43 | Mor | Ph | 4-Thiz | Me | Me | Me | H |
| 4-44 | Mor | Ph | 4-Thiz | Me | Me | Et | H |
| 4-45 | Mor | Ph | 4-Thiz | Me | Me | Et | Me |
| 4-46 | Mor | Ph | 4-Thiz | Et | Et | Me | H |
| 4-47 | Mor | Ph | 5-Isox | Me | Me | Me | H |
| 4-48 | Mor | Ph | 5-Isox | Me | Me | Et | H |
| 4-49 | Mor | Ph | 5-Imid | Me | Me | Me | H |
| 4-50 | Mor | Ph | 5-Imid | Me | Me | Et | H |
| 4-51 | Mor | Ph | 5-Imid | Et | Me | Me | H |
| 4-52 | Mor | Ph | 5-Imid | Et | Et | Me | H |
| 4-53 | Bz(Me)N- | Ph | 4-Thiz | Me | Me | Me | H |
| 4-54 | Bz(Me)N- | Ph | 4-Thiz | Me | Me | Et | H |
| 4-55 | Bz(Me)N- | Ph | 5-Isox | Me | Me | Me | H |
| 4-56 | Bz(Me)N- | Ph | 5-Imid | Me | Me | Me | H |
| 4-57 | cHx(Me)N- | Ph | 4-Thiz | Me | Me | Me | H |
| 4-58 | cHx(Me)N- | Ph | 5-Isox | Me | Me | Me | H |
| 4-59 | cHx(Me)N- | Ph | 5-Imid | Me | Me | Me | H |
| 4-60 | Me | Ph | 4-Thiz | Me | Me | Me | H |
| 4-61 | Et | Ph | 4-Thiz | Me | Me | Me | H |
| 4-62 | Et | Ph | 5-Isox | Me | Me | Me | H |
| 4-63 | Et | Ph | 5-Imid | Me | Me | Me | H |
| 4-64 | iPr | Ph | 4-Thiz | Me | Me | Me | H |
| 4-65 | iPr | Ph | 5-Isox | Me | Me | Me | H |
| 4-66 | iPr | Ph | 5-Imid | Me | Me | Me | H |
| 4-67 | tBu | Ph | 4-Thiz | Me | Me | Me | H |
| 4-68 | tBu | Ph | 4-Thiz | Me | Me | Et | H |
| 4-69 | tBu | Ph | 5-Isox | Me | Me | Me | H |
| 4-70 | tBu | Ph | 5-Imid | Me | Me | Me | H |

TABLE 5

| Cpd No | R¹ | R² | R³ | R⁴ | R⁷ |
|---|---|---|---|---|---|
| 5-1 | Mor | 1-Np | 4-Thiz | cHx | 2-MorEt |
| 5-2 | Mor | 1-Np | 4-Thiz | cHx | Hx |
| 5-3 | Bz(Me)N- | 1-Np | 4-Thiz | cHx | Hx |
| 5-4 | cHx(Me)N- | 1-Np | 4-Thiz | cHx | Hx |
| 5-5 | Mor | Ph | 4-Thiz | cHx | Me |
| 5-6 | Mor | 1-Np | 4-Thiz | cHx | Me |

TABLE 6

| Cpd No | R¹ | R² | R³ | R⁴ | R⁷ |
|---|---|---|---|---|---|
| 6-1 | Mor | 1-Np | 4-Thiz | cHx | Hx |
| 6-2 | Bz(Me)N- | 1-Np | 4-Thiz | cHx | Hx |
| 6-3 | Mor | Ph | 4-Thiz | cHx | Me |
| 6-4 | Mor | Ph | 4-Thiz | cHx | iBu |
| 6-5 | Mor | Ph | 4-Thiz | cHx | 2-MeBu |
| 6-6 | Mor | Ph | 4-Thiz | cHx | 2-MorEt |
| 6-7 | Mor | Ph | 4-Thiz | iPr | Me |
| 6-8 | Bz(Me)N- | Ph | 4-Thiz | cHx | Me |
| 6-9 | cHx(Me)N- | Ph | 4-Thiz | cHx | Me |
| 6-10 | Me | Ph | 4-Thiz | cHx | Me |
| 6-11 | Me | Ph | 4-Thiz | cHx | Et |
| 6-12 | Et | Ph | 4-Thiz | cHx | Me |
| 6-13 | iPr | Ph | 4-Thiz | cHx | Me |
| 6-14 | tBu | Ph | 4-Thiz | cHx | Me |
| 6-15 | Mor | Mph | 4-Thiz | cHx | Me |
| 6-16 | cHx(Me)N- | Mph | 4-Thiz | cHx | Me |
| 6-17 | Me | Mph | 4-Thiz | cHx | Me |
| 6-18 | iPr | Mph | 4-Thiz | cHx | Me |
| 6-19 | tBu | Mph | 4-Thiz | cHx | Me |
| 6-20 | Mor | 1-Np | 4-Thiz | cHx | Me |
| 6-21 | Bz(Me)N- | 1-Np | 4-Thiz | cHx | Me |
| 6-22 | Me | 1-Np | 4-Thiz | cHx | Me |
| 6-23 | tBu | 1-Np | 4-Thiz | cHx | Me |
| 6-24 | Bz(Me)N- | Mph | 4-Thiz | cHx | Me |

TABLE 7

| Cpd No | R¹ | R² | R³ | R⁴ | R⁷ |
|---|---|---|---|---|---|
| 7-1 | tBuO | 1-Np | 4-Thiz | cHx | 2-MeBu |
| 7-2 | tBuO | 1-Np | 4-Thiz | cHx | 2-MorEt |
| 7-3 | tBuO | 1-Np | 4-Thiz | cHx | 3-(2-oxo-1-Pyrd)Pr |
| 7-4 | tBuO | 1-Np | 5-Isox | cHx | Hx |
| 7-5 | tBuO | 1-Np | 5-Imid | cHx | Hx |
| 7-6 | tBuO | Ph | 4-Thiz | cHx | Bu |
| 7-7 | tBuO | Ph | 4-Thiz | cHx | 2-MorEt |
| 7-8 | tBuO | Ph | 4-Thiz | cHx | 3-(2-oxo-1-Pyrd)Pr |
| 7-9 | tBuO | Ph | 5-Isox | cHx | Hx |
| 7-10 | tBuO | Ph | 5-Imid | cHx | Hx |
| 7-11 | tBuO | Ph | 4-Thiz | iPr | Hx |
| 7-12 | tBuO | Ph | 4-Thiz | iPr | 2-MorEt |
| 7-13 | tBuO | Ph | 5-Isox | iPr | Hx |
| 7-14 | tBuO | Ph | 4-Thiz | cHx | Me |

TABLE 8

| Cpd No | R¹ | R³ | R⁵ | R⁶ | R⁷ | A |
|---|---|---|---|---|---|---|
| 8-1 | Mor | 4-Thiz | Et | Et | 2-MorEt | —CH₂CH₂— |

TABLE 8-continued

| Cpd No | R$^1$ | R$^3$ | R$^5$ | R$^6$ | R$^7$ | A |
|---|---|---|---|---|---|---|
| 8-2 | Mor | 4-Thiz | Me | Me | Me | —CH(Me)— |

Of the compounds listed above, the preferred compounds are Compounds No. 1-7, 1-37, 1-48, 2-1, 3-4, 3-8, 3-34, 3-64, 3-66, 3-90, 3-91, 3-97, 3-112, 3-114, 3-120, 3-152, 4-34, 6-3, 6-20 and 7-1. The most preferred compounds are Compounds No.:

1-7. 5-{N-[N-Morpholinoacetyl-3-(1-naphthyl)alanyl]-3-(4-thiazolyl)alanyl}amino-6-cyclohexyl-4-hydroxy-2-(1-hydroxy-1-methylethyl)-N-(2-methylbutyl)hexanamide, especially the (2S, 4S, 5S)-5-{N-[N-morpholinoacetyl-3-(1-naphthyl)-L-alanyl]-3-(4-thiazolyl)-L-alanyl}amino-6-cyclohexyl-4-hydroxy-2-(1-hydroxy-1-methylethyl)-N-[2(S)-methylbutyl]hexanamide isomer;

3-4. 5-{N-[2-(1-Naphthylmethyl)-3-(morpholinocarbonyl)propionyl]-3-(4-thiazolyl)alanyl}amino-6-cyclohexyl-4-hydroxy-2-(1-hydroxy-1-methylethyl)-N-methylhexanamide, especially the (2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-methylhexanamide isomer;

3-8. 5-{N-[2-(1-Naphthylmethyl)-3-(morpholinocarbonyl)propionyl]-3-(4-thiazolyl)alanyl}amino-6-cyclohexyl-4-hydroxy-2-(1-hydroxy-1-methylethyl)-N-(2-methylbutyl)hexanamide, especially the (2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide isomer;

3-34. 5-{N-[2-(1-Naphthylmethyl)-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide, especially the (2S, 4S, 5S)-5-{N-[ 2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-ethylpropyl)-N-methylhexanamide isomer;

3-64. 5-{N-[2-Benzyl-3-(morpholinocarbonyl)propionyl]-3-(4-thiazolyl)alanyl}amino-6-cyclohexyl-4-hydroxy-2-(1-hydroxy-1-methylethyl)-N-butylhexanamide, especially the (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxyl-1-methylethyl)-N-butylhexanamide isomer;

3-66. 5-{N-[2-Benzyl-3-(morpholinocarbonyl)propionyl]-3-(4-thiazolyl)alanyl}amino-6-cyclohexyl-4-hydroxy-2-(1-hydroxy-1-methylethyl)-N-(2-methylbutyl)hexanamide, especially the (2S, 4S, 5S)-5-{N-[2(R)-benzyl-3-morpholinocarbonyl)propionyl]-3-(4-thiazolyl)-L--alanyl}amino-6-cyclohexyl-4-hydroxy-2-(1-hydroxy-1-methylethyl)-N-[2(S)-methylbutyl]hexanamide isomer;

3-90. 5-{N-[2-Benzyl-3-(morpholinocarbonyl)propionyl]-3-(4-thiazolyl)alanyl}amino-6-cyclohexyl-4-hydroxy-2-(1-hydroxy-1-methylethyl)-N-methylhexanamide, especially the (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide isomer;

3-91. 5-{N-[2-Benzyl-3-(morpholinocarbonyl)propionyl]-3-(4-thiazolyl)alanyl}amino-6-cyclohexyl-4-hydroxy-2-(1-hydroxy-1-methylethyl)-N-ethylhexanamide, especially the (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxyl-1-methylethyl)-N-ethylhexanamide isomer;

3-97. 5-{N-[2-Benzyl-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide, especially the (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-ethylpropyl)-N-methylhexanamide isomer;

3-112. 5-{N-[2-Benzyl-3-(N-benzyl-N-methylcarbamoyl)propionyl]-3-(4-thiazolyl)alanyl}amino-6-cyclohexyl-4-hydroxy-2-(1-hydroxy-1-methylethyl)-N-methylhexanamide, especially the (2S, 4S, 5S)-5-{N-[2(R)-benzyl-3-(N-benzyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide isomer;

3-114. 5-{N-[2-Benzyl-3-(N-cyclohexyl-N-methylcarbamoyl)propionyl]-3-(4-thiazolyl)alanyl}amino-6-cyclohexyl-4-hydroxy-2-(1-hydroxy-1-methylethyl)-N-methylhexanamide, especially the (2S, 4S, 5S)-5-{N-[2(R)-benzyl-3-(N-cyclohexyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide isomer;

3-152. 5-{N-[2-(p-Methoxybenzyl)-3-(morpholinocarbonyl)propionyl]-3-(4-thiazolyl)alanyl}amino-6-cyclohexyl-4-hydroxy-2-(1-hydroxy-1-methylethyl)-N-methylhexanamide, especially the (2S, 4S, 5S)-5-{N-[2(R)-(p-methoxybenzyl)-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide isomer; and 6-20. 5-{N-[2-(1-Naphthylmethyl)-3-(morpholinocarbonyl)propionyl]-3-(4-thiazolyl)alanyl}amino-6-cyclohexyl-4-hydroxy-2-(1-hydroxycyclohexyl)-N-methylhexanamide, especially the (2S, 4S, 5S)-5-{N-[2(R-)-(1-naphthylmethyl)-3-(morpholinocarbonyl)propionyl]-3-(4-thiazolyl)-L-alanyl}amino-6-cyclohexyl-4-hydroxy-2-(1-hydroxycyclohexyl)-N-methylhexanamide isomer;

and the pharmaceutically acceptable salts of the above compounds, especially the hydrochlorides.

The compounds of the present invention are oligopeptides and may, therefore, be prepared, as is well known in the art by reacting together the component amino acids in any appropriate order, by reacting together two or more lower oligopeptides (again, if necessary, in an appropriate order) or by reacting one or more component amino acids with one or more lower oligopeptides (again, if necessary, in an appropriate order). However, provided that the correct sequence of amino acid residues in the oligopeptide of formula (I) is achieved, there is no particular restriction upon the order in which these reactions are carried out. In general terms, the compounds of the invention may be prepared by reacting together compounds of formulae:

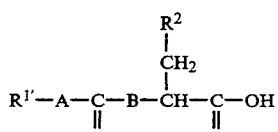

(III)

or a reactive derivative thereof,

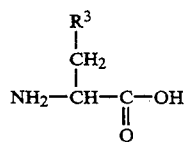

(IV)

or a reactive derivative thereof,

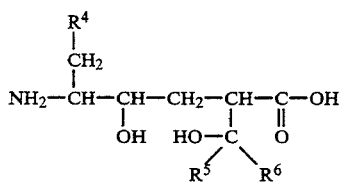

(V)

or a reactive derivative thereof, and

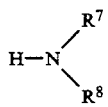

(VI)

or a reactive derivative thereof (in the above formulae $R^2$-$R^8$ and A and B are as defined above and $R^{1'}$ represents any of the groups represented by $R^1$ or an active group), and, where $R^{1'}$ represents said active group, converting it to any one of the groups represented by $R^1$;

or by reacting a peptide compound derivable by reaction of some of said compounds of formulae (III), (IV), (V) or (VI) or said reactive derivatives with the remainder of said compounds or said reactive derivative(s) or with a peptide compound or compounds derivable by reaction of said remainder or reactive derivative(s) thereof, the reaction(s) being in an order corresponding to the order of the residues derived from said compounds of formulae (III), (IV), (V) and (VI) in said compound of formula (I). Also, where B represents an imino group of formula —NH—, the compound of formula (III) may, if desired, be replaced by the two compounds of formulae (IIIa) and (IIIb):

(IIIa)

and

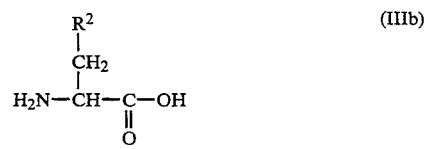

(IIIb)

(in which $R^{1'}$ and $R^2$ are as defined above).

If required, the resulting compound of formula (I) may be subjected to any one or more of various optional reactions, for example salification.

In specific embodiments of the process of the present invention, the compounds of the invention may be prepared by any of the following Reaction Schemes A, B and C.

Reaction Scheme A:

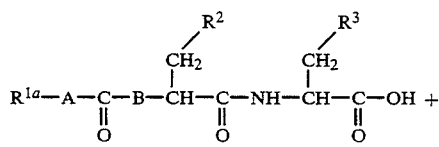

(VII)

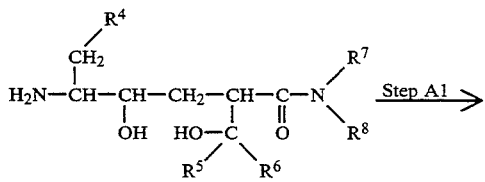

(VIII)

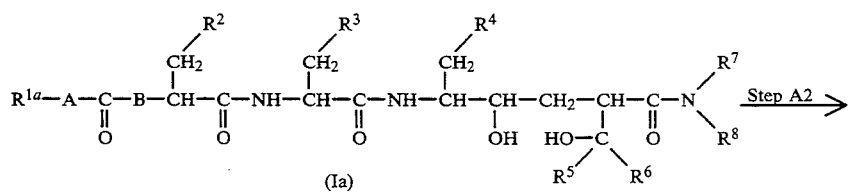

(Ia)

-continued

Reaction Scheme A:

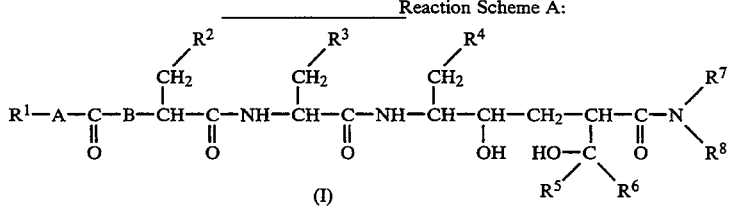

Reaction Scheme B:

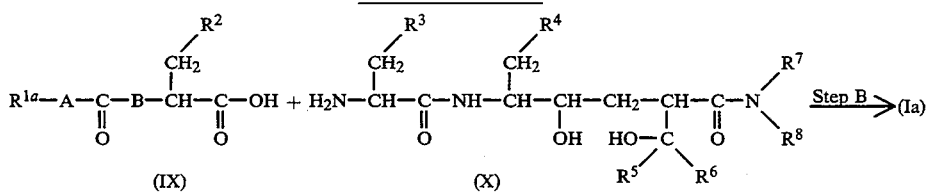

Reaction Scheme C:

In which A represents a $C_1$—$C_3$ alkylene group and B represents an amino group:

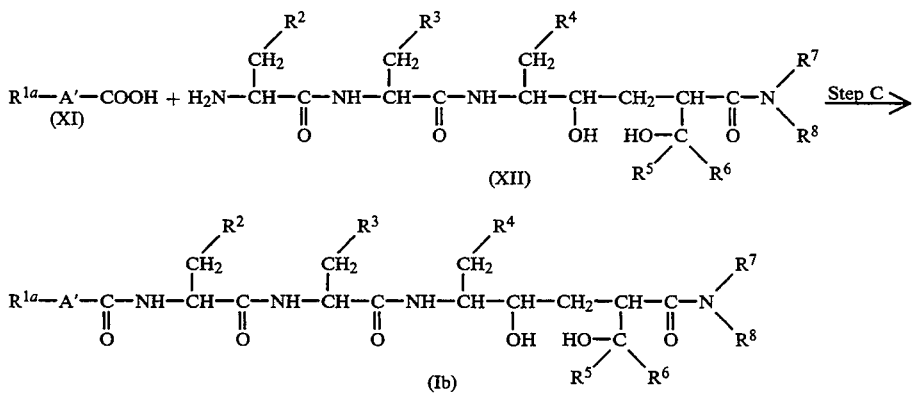

In the above formulae: A, B, $R^1$, $R^2$, $R^3$, $R^4$, $R^5$, $R^6$, $R^7$ and $R^8$ are as defined above;

A' represents a $C_1$-$C_3$ alkylene group; and $R^{1a}$ represents any one of the groups defined above for $R^1$ except that, where $R^1$ represents an imino (—NH—) or amino group, this is protected.

Where $R^{1a}$ represents a protecting group, this may be any such group conventionally employed in the field of amino acid chemistry. Examples include: an aralkyloxycarbonyl group, such as a benzyloxycarbonyl or p-methoxybenzyloxycarbonyl group; or a carbonate residue such as a t-butoxycarbonyl group or a 9-fluorenylmethoxycarbonyl group, but these are given purely by way of exemplification and it will be understood that any other protecting group may equally be used in these reactions, provided that it can protect the amino or imino group and that it has no adverse effect on the reaction.

In Step A1 of Reaction Scheme A, a compound of formula (Ia) is prepared by reacting the compound of formula (VII) or a reactive derivative thereof with the compound of formula (VIII).

This reaction, like the other principal reactions in Reaction Schemes A, B and C, is a standard condensation reaction of the type conventionally used in peptide synthesis and it and they may be carried out according to any of the well known techniques conventionally employed in peptide synthesis, for example by the azide method, the active ester method, the mixed acid anhydride method, the carbodiimide method or the condensation method. The reactive derivatives employed in these reactions are those reactive derivatives conventionally employed in such methods. Certain of these methods are described in more detail below.

Azide Method

First, the carboxylic acid of formula (VII) (Reaction Scheme A) as such, or, more usually, in the form of its corresponding alkyl ester, is treated with hydrazine in an inert solvent, to give the corresponding acid hydrazide. The nature of the solvent employed in this reaction is not critical and any solvent commonly employed in this type of reaction may equally be employed here; however, we generally find it convenient to use a polar solvent, especially a fatty acid amide, such as dimethylformamide. Also, the reaction temperature is not critical and the reaction will take place over a wide range of temperatures; we generally find it convenient to carry out the reaction at a temperature of from −50° C. to 10° C.

The resulting hydrazide is then reacted with a nitrite, to convert it into an azide, after which the azide is reacted with the amine of formula (VIII) (Reaction Scheme A).

Examples of nitrites which may be employed include: alkali metal nitrites, such as sodium nitrite; and alkyl nitrites, such as isoamyl nitrite.

The reaction of the acid hydrazide with the nitrite and the subsequent reaction of the resulting azide with the amine of formula (VIII) are commonly carried out in the same reaction solution, without intermediate isolation of the azide. Both reactions are preferably carried out in the presence of an inert solvent. The nature of the solvent is not critical, provided that it does not interfere with the reaction. Suitable solvents include, for example: amides, such as dimethylformamide or dimethylacetamide; sulfoxides, such as dimethyl sulfoxide; and pyrrolidones, such as N-methylpyrrolidone. Although there is no criticality as to the reaction temperature, the reaction with the nitrite is preferably effected at a relatively low temperature, e.g. from $-50°$ C. to $0°$ C., whilst the reaction of the azide with the amine is preferably effected at a temperature of from $-10°$ C. to $+10°$ C. The time required for each of these reactions will vary, depending upon the nature of the reagents and the reaction temperature, but a period of from 5 minutes to 1 hour and a period of from 10 hours to 5 days will normally suffice for the reaction with the nitrite and the reaction of the azide with the amine, respectively.

Active Ester Method

In this method, the carboxylic acid of formula (VII) (Reaction Scheme A) is first converted to an active ester by reacting it with a suitable reagent for producing active esters, after which this active ester is reacted with the amine of formula (VIII).

Formation of the active ester is preferably effected by reacting the carboxylic acid of formula (VII) with, for example, an N-hydroxyimide compound, such as N-hydroxysuccinimide, 1-hydroxybenzotriazole or N-hydroxy-5-norbornene-2,3-dicarboximide. The reaction to form the active ester is preferably effected in the presence of a condensing agent, such as dicyclohexylcarbodiimide or carbonyldiimidazole.

The reaction to form the active ester is also preferably effected in the presence of an inert solvent, the nature of which is not critical, provided that it has no adverse effect upon the reaction. Suitable solvents include, for example: halogenated hydrocarbons, preferably halogenated aliphatic hydrocarbons, such as methylene chloride or chloroform; ethers, such as diethyl ether or tetrahydrofuran; and amides, such as dimethylformamide or dimethylacetamide.

The reaction temperature may vary over a wide range, for example from $-10°$ C. to $25°$ C. The time required for the reaction may also vary widely, depending upon the nature of the reagents and upon the reaction temperature, but a period of from 30 minutes to 10 hours will normally suffice.

Reaction of this active ester with the amine of formula (VIII) may be carried out with or without intermediate isolation of the active ester. Reaction of the active ester with the amine is preferably effected in the presence of an inert solvent, examples of which are as given for the preparation of the active ester itself. The temperature required for the reaction is not particularly critical and, for this reason, we normally prefer to carry out the reaction at about ambient temperature, although other reaction temperatures may also be employed with equal success. The time required for the reaction will vary widely, but a period of from 30 minutes to 10 hours will normally suffice.

Mixed Acid Anhydride Method

In this method, the carboxylic acid of formula (VII) (Reaction Scheme A) is first converted to a mixed acid anhydride, and this is then reacted with the amine of formula (VIII).

Preparation of the mixed acid anhydride is effected by reacting the acid of formula (VII) with a suitable reagent, preferably in the presence of an inert solvent. Suitable reagents include: lower alkyl haloformates, such as ethyl chloroformate or isobutyl chloroformate; and di(lower alkyl) cyanophosphonates, such as diethyl cyanophosphonate. Examples of suitable inert solvents include the amides and ethers referred to in relation to the active ester method.

This reaction is preferably effected in the presence of an organic amine, such as triethylamine or N-methylmorpholine. The reaction temperature may vary over a wide range, for example from $-10°$ C. to $25°$ C. The period required for the reaction may also vary widely, depending upon such factors as the nature of the reagents and the reaction temperature, but a period of from 30 minutes to 5 hours will normally suffice.

Reaction of the resulting mixed acid anhydride with the amine of formula (VIII) is preferably effected in the presence of an inert solvent, the nature of which is not critical, provided that it does not interfere with the reaction. Suitable solvents include the amides and ethers hereinbefore exemplified in relation to the active ester method. The reaction will take place over a wide range of temperatures, but we generally find it convenient to carry out the reaction at a temperature of from $0°$ C. to about ambient temperature. The time required for the reaction will vary, depending upon many factors, such as the nature of the reagents and the reaction temperature, but a period of from 1 hour to 24 hours will normally suffice.

Condensation Method

In this method, the carboxylic acid of formula (VII) (Reaction Scheme A) is directly reacted with the amine of formula (VIII). Such a reaction is preferably effected in the presence of a condensing agent, such as dicyclohexylcarbodiimide or carbonyldiimidazole. Otherwise, the reaction conditions and solvents are similar to those already described in relation to the active ester method.

In Step A2, if required, the protecting group is removed from the group represented by $R^{1a}$, to convert it to one of the groups defined for $R^1$, and produce the compound of formula (I).

The removal of the protecting group may be effected by conventional means and the precise removal reaction chosen will depend upon the nature of the protecting group.

For example, where the amino-protecting group is a t-butoxycarbonyl group, this group may be removed by treatment with an acid (e.g. hydrochloric acid, hydrofluoric acid, trifluoroacetic acid or boron trifluoride, preferably in the form of a complex, e.g. the diethyl etherate), optionally in the presence of a cation scavenger (e.g. anisole or thioanisole). Such a reaction is preferably effected in an inert solvent. The nature of the solvent is not critical, provided that it has no adverse effect on the reaction, and examples of suitable solvents include: ethers, such as dioxane; lower alcohols, such as methanol; and amides, such as dimethylformamide. The reaction will take place over a wide range of temperatures, and the precise temperature chosen is not critical; we generally find it convenient to carry out the reaction at, for example, a temperature of from 0° C. to 30° C. The time required for the reaction may vary widely, depending upon many factors, notably the nature of the reagents and the reaction temperature; however, a period of from 20 minutes to 1 hour will normally suffice.

When the amino or imino group is protected by an aralkyloxycarbonyl group or other carbonate residue, the protecting group can be removed by catalytic reduction of the protected compound in the presence of hydrogen (for example under a hydrogen pressure of from atmospheric to 10 atmospheres) and in the presence of a suitable hydrogenation catalyst, for example palladium-on-carbon or palladium black. The reaction is preferably effected in the presence of an inert solvent, the nature of which is not critical, provided that it has no adverse effect on the reaction, and examples of suitable solvents include: lower alcohols, such as methanol or ethanol; and ethers, such as tetrahydrofuran. We generally find it convenient to carry out the reaction at about ambient temperature, although this is not critical. The time required for the reaction may vary widely, but a period of from 1 to 8 hours will normally suffice.

Reaction Scheme B shows an alternative method of preparing the compound of formula (Ia). In the reaction shown here, a compound of formula (IX) is reacted with a compound of formula (X). This is an amino acid condensation reaction, and it may be effected using any of the reactions exemplified for the similar reaction of Step A1 in Reaction Scheme A.

In Reaction Scheme C, there is shown an alternative method of preparing the compound of formula (Ib), in which A represents a $C_1$-$C_3$ alkylene group and B represents an imino group, by reacting the compound of formula (XI) with the compound of formula (XII). This is an amino acid condensation reaction, and it may be effected using any of the reactions exemplified for the similar reaction of Step A1 in Reaction Scheme A.

If desired, certain groups in the compound of formula (I) prepared as described above may be converted to certain other groups by appropriate reactions well-known in the field of peptide synthesis. For example, if desired, any acyl group within the resulting compound of formula (I) may be converted to any other acyl group; the reactions and reaction conditions involved in such conversions are well known in the art.

After completion of any of the above reactions or of the final such reaction, the desired compound may be isolated from the reaction mixture by conventional means. For example, one suitable recovery procedure comprises: if necessary, neutralizing the reaction mixture; removing the insoluble residue, if any, by filtration; and then distilling off the solvent to give the desired compound. If necessary, this compound may be further purified by such conventional means as recrystallization, reprecipitation or the various chromatography techniques, such as column chromatography or preparative thin layer chromatography.

Preparation of Starting Materials

The compound of formula (VII) used as a starting material in Reaction Scheme A of the present invention can be prepared by reacting a compound of formula (IXa), prepared as described in Reaction Scheme F, shown hereafter, or an acylamino acid of formula (XIII):

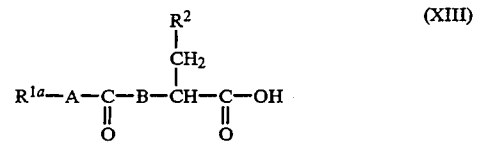

(in which $R^{1a}$, $R^2$ and A are as defined above) with an ester of an amino acid of formula (XIV):

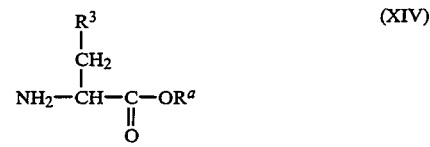

(in which $R^3$ is as defined above and $R^a$ represents an ester group). This is an amino acid condensation reaction, and it may be effected using any of the reactions exemplified for the similar reaction of Step A1 in Reaction Scheme A. The product is an ester of a compound of formula (VII), and it may be converted to the free compound of formula (VII) by hydrolyzing the ester compound by conventional means.

The compounds of formulae (X) and (XII) used as starting materials in the reactions of Reaction Schemes B and C, respectively, can be prepared from the compound of formula (XV), shown in Reaction Scheme D below, by a conventional peptide synthesis reaction. The compound of formula (VIII) can be prepared predominantly as the isomer having the desired S-configuration by the sequence of reactions shown in the following Reaction Scheme D.

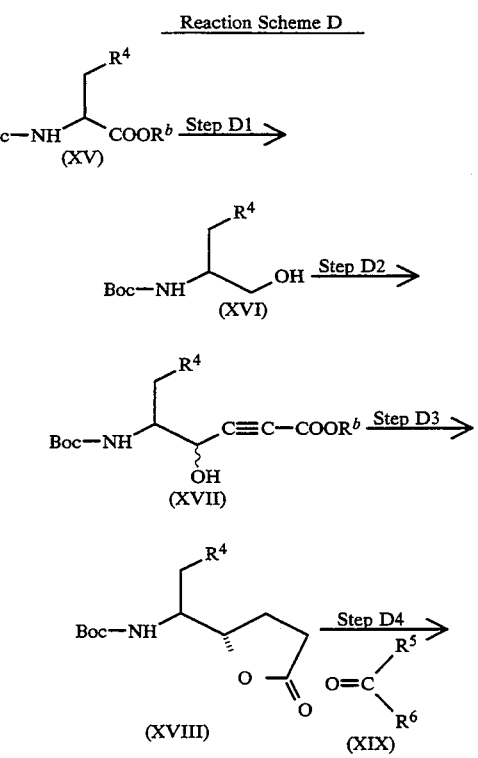

-continued
Reaction Scheme D

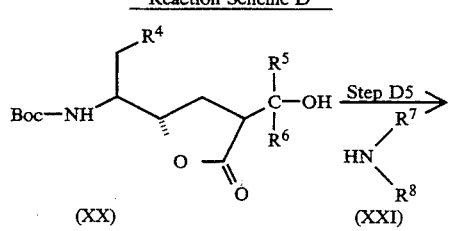

(XX)  (XXI)

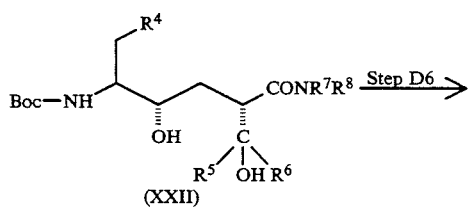

(XXII)

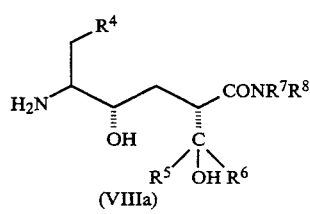

(VIIIa)

In the above formulae:

$R^4$, $R^5$, $R^6$, $R^7$ and $R^8$ are as defined above;

Boc represents a t-butoxycarbonyl group; and $R^b$ represents a lower, e.g. $C_1$-$C_4$, alkyl group.

Thus, in Step D1 of this reaction scheme, the compound of formula (XV) is treated with a reducing agent, such as sodium borohydride, to give the compound of formula (XVI). This compound of formula (XVI) is then oxidized in Step D2 with an oxidizing agent, such as a sulfur trioxide-pyridine complex, and the resulting compound is then reacted with an alkali metal salt (for example lithium salt) of a lower alkyl (e.g. $C_1$-$C_4$ alkyl) acetylenemonocarbonate, at a temperature ranging from 0° C. to −78° C., to give the compound of formula (XVII). After catalytic reduction of the compound of formula (XVII) in the presence of a catalyst such as palladium-barium sulfate, the product is heated in the presence of a catalytic amount of an acid, such as acetic acid, (in Step D3), to afford the compound of formula (XVIII). In Step D4, this compound of formula (XVIII) is treated with a ketone of formula (XIX) in the presence of a base, such as lithium diisopropylamide, to give the compound of formula (XX). This is subsequently reacted, in Step D5, with an amine of formula (XXI), to give the compound of formula (XXII). The starting material of formula (VIIIa) can then be prepared, in Step D6, from the compound of formula (XXII) by removing the protecting group by conventional means.

The starting material of formula (X) used in Reaction Scheme B can be prepared by the same sequence of reactions as described above in Reaction Scheme D, but replacing the compound of formula (XVI) with the compound of formula (XVIa):

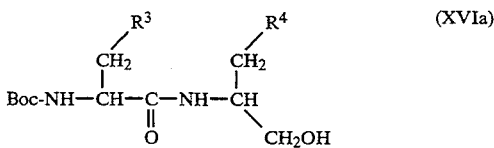

(in which $R^3$, $R^4$ and Boc are as defined above)

This compound of formula (XVIa) may be prepared by reacting the compound obtained by removing the t-butoxycarbonyl group from the compound of formula (XVI) with a compound of formula (XXIII):

(in which $R^3$ is as defined above). This is an amino acid condensation reaction, and it may be effected using any of the reactions exemplified for the similar reaction of Step A1 in Reaction Scheme A.

An alternative method of preparing the compound of formula (XXII) is shown in Reaction Scheme E:

Reaction Scheme E

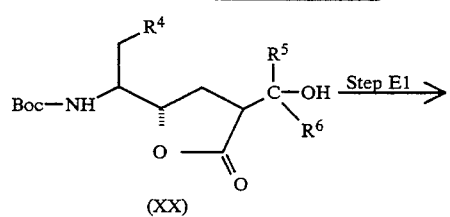

(XX)

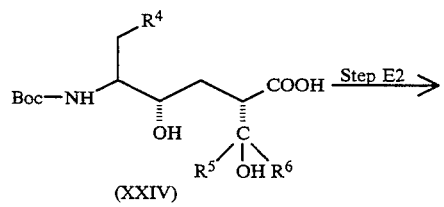

(XXIV)

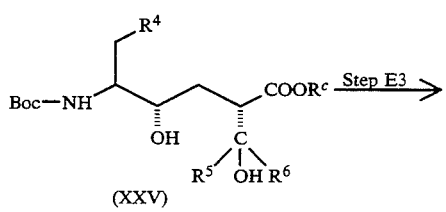

(XXV)

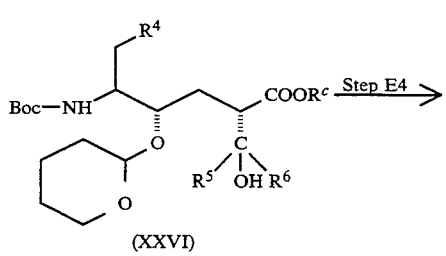

(XXVI)

-continued
Reaction Scheme E

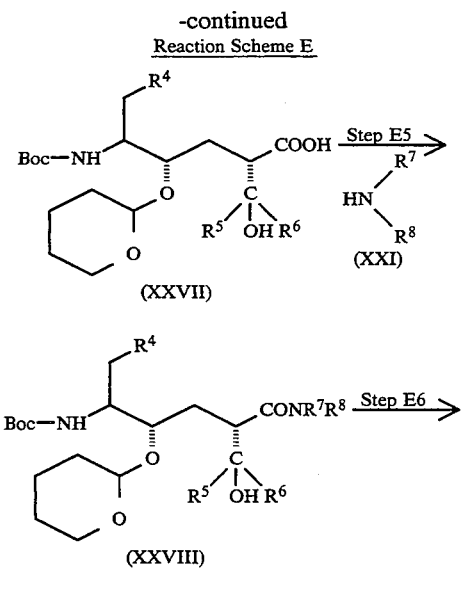

In the above formulae:

$R^4$, $R^5$, $R^6$, $R^7$, $R^8$ and Boc are as defined above; and $R^c$ represents an aralkyl group.

Thus, in Step E1, the lactone ring of the compound of formula (XX) (prepared as described in Step D4 of Reaction Scheme D) is opened to form the carboxylic acid of formula (XXIV) by treatment with an alkali, such as sodium hydroxide, in an aqueous solvent. Then, in Step E2, the resulting acid of formula (XXIV) is converted into an aralkyl ester of formula (XXV) by treatment with an aralkyl halide in a solvent, such as dimethylformamide, in the presence of a base, such as potassium carbonate. In Step E3, this ester of formula (XXV) is converted into the compound of formula (XXVI) by reacting it with a hydroxy-protecting agent such as 3,4-dihydro-2-H-pyran. The aralkyl group is then removed by catalytic reduction, in Step E4, to afford the compound of formula (XXVII), which is then converted, in Step E5, by reaction with an amine of formula (XXI) to the compound of formula (XXVIII). Finally, the desired compound of formula (XXII) is obtained, in Step E6, by removing the hydroxy-protecting group from the compound of formula (XXVIII).

The starting material of formula (IX), where A represents a single bond, and B represents a $C_1$–$C_2$alkylene group, used in Reaction Scheme B, i.e. the compound of formula (IXa), can be prepared stereoselectively as the stereoisomer with the desired S-configuration by the method illustrated in Reaction Scheme F:

Reaction Scheme F

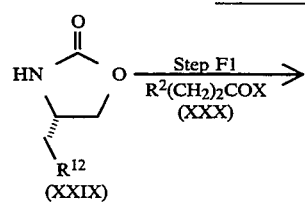

-continued
Reaction Scheme F

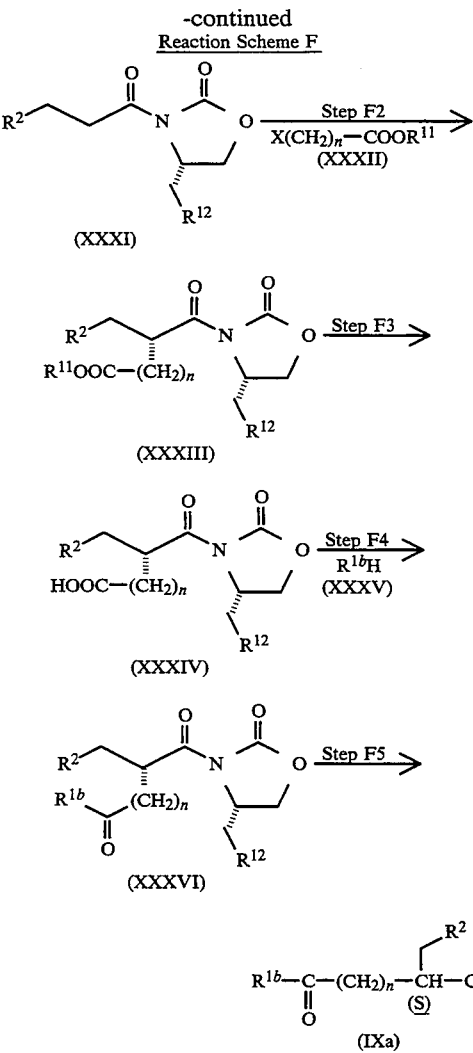

In the above formulae:

$R^2$ is as defined above;

$R^{1b}$ represents any one of the groups defined for $R^{1a}$ other than a lower alkyl group or a lower alkoxy group, i.e. it represents a heterocyclic group or said group of formula (II);

n is the integer 1 or 2;

$R^{11}$ represents a lower, e.g. $C_1$–$C_4$, alkyl group or an aralkyl group;

$R^{12}$ represents a phenyl group or a lower, e.g. $C_1$–$C_4$, alkyl group; and X represents a halogen atom.

Thus, in Step F1, the compound of formula (XXIX) is converted into its corresponding alkali metal salt by treating it with a base (for example butyllithium); it is then reacted with an acid halide of formula (XXX) to give the compound of formula (XXXI). In Step F2, after treating the resulting compound of formula (XXXI) with a base (for example, lithium diisopropylamide) the product is reacted stereoselectively with the halide compound of formula (XXXII) to give a compound of formula (XXXIII). In Step F3, this compound of formula (XXXIII) is then subjected to catalytic reduction (for example, by reaction in an atmosphere of hydrogen in the presence of palladium-on-charcoal) or to hydrolysis, to give the compound of formula (XXXIV), which is then reacted, in Step F4, with an amine compound of formula (XXXV) in the presence of a condensing agent (for example, diethyl cyanophosphate and triethylamine), to afford the compound of formula (XXXVI). The compound thus obtained is finally hydrolyzed in Step F5, to give the compound of formula (IXa).

The amino acid of formula (XXXVII):

(in which $R^3$ is as defined above), which is used to prepare certain of the starting materials used in the above reaction schemes, can be prepared without difficulty by the method shown in Reaction Scheme G, or it can be purchased commercially.

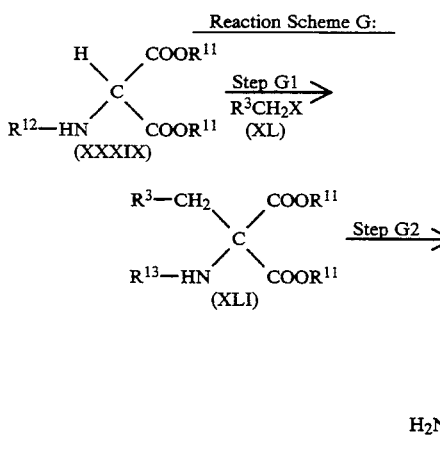

In the above formulae:

$R^3$, $R^{11}$ and X are as defined above; and $R^{13}$ represents an aliphatic acyl group, such as an acetyl, propionyl or butyryl group.

Thus, in Step G1, the compound of formula (XLI) can be prepared by treating the compound of formula (XXXIX) with a base (for example an alkali metal hydride, such as sodium hydride) and then reacting the product with the compound of formula (XL). The resulting compound of formula (XLI) is then treated with an acid (for example a mineral acid, such as hydrochloric acid), to give the desired compound of formula (XXXVIII).

INHIBITION OF RENIN ACTIVITY

The ability of various compounds of the invention to inhibit the activity of renin was determined according to the following method, which follows essentially the procedure of Kokubu et al. [Hypertension, 5, 191–197 (1983)].

Specifically, each test compound was dissolved in 60% v/v aqueous ethanol. Human renin activity in the presence and absence of each compound was measured using sheep angiotensinogen. The total volume of 1 ml of assay mixture contained 0.1 mole/liter phosphate buffer (pH 7.3), human renin (equivalent to 0.5 ng angiotensin I per ml per minute), sheep angiotensinogen (equivalent to 200 ng angiotensin I), $1 \times 10^{-6}$M of the test compound, 6% v/v ethanol and angiotensinase inhibitors (10 mmole/liter sodium ethylenediaminetetraacetate and 3.4 mmole/liter 8-hydroxyquinoline). The mixture was allowed to react for 10 minutes at 37° C., and then the reaction was stopped by placing the reaction tube in a boiling water bath for 5 minutes. The mixture was then centrifuged and the supernatant (0.05–0.1 ml) was used to assay remaining angiotensin I.

An identical experiment was carried out, as a control, except that the test compound was omitted. From the values obtained were calculated the % inhibition of renin activity achieved by each test compound. The results are shown in the following Table 9, in which the compounds of the invention are identified by the numbers of the Examples given hereafter in which are described their preparation. The values given are the mean of 3 or 4 experiments.

TABLE 9

| Test Compound | Inhibitory Activity (%) Against Human Renin ($1 \times 10^{-7}$) |
|---|---|
| Compound of Example 2 | 96.3 |
| Compound of Example 3 | 96.7 |
| Compound of Example 4 | 96.8 |
| Compound of Example 5 | 92.2 |
| Compound of Example 7 | 98.2 |
| Compound of Example 8 | 97.4 |
| Compound of Example 9 | 90.9 |

As can be seen from the results in the Table above, the compounds of the present invention have a substantial inhibitory effect on the activity of human renin and are thus useful for the diagnosis and therapy of renin-/angiotensin-induced hypertension in humans and other animals. Furthermore, we have found from biliary excretion and blood plasma experiments that the compounds are well absorbed from the digestive tract upon oral administration and this has been supported by tests in marmosets. Moreover, the compounds of the invention are readily soluble in water. Furthermore, in animal tests using mice and rats, the compounds of the present invention have demonstrated a lower toxicity than do the prior art compounds. All of these results indicate that the compounds of the invention will be of considerable therapeutic value and that, unlike related compounds proposed previously, they may be administered, in practice, by the oral route, as well as by the more conventional parenteral route.

The compounds of the invention may be formulated in conventional dosage forms, normally in admixture with a pharmaceutical carrier or diluent. For oral administration, the compounds can be formulated, for example, as tablets, capsules, granules, powders or syrups. For parenteral administration, they may be formulated as injections in a suitable liquid or as suppositories. The dosage will vary, depending upon the age, symptoms and body weight of the patient, as well as upon the desired end result; however, we would normally anticipate administering a dose of from 0.01 mg to 100 mg/kg body weight per day, which may be administered as a single dose or in divided doses.

The invention is further illustrated by the following Examples, which illustrate the preparation of certain of the compounds of the present invention, and the subsequent Preparations, which illustrate the preparation of some of the starting materials used in the preparation of the compounds of the present invention.

EXAMPLE 1

(2S, 4S, 5S)-5-{N-[N-(t-Butoxycarbonyl)-3-(4-thiazolyl)-L-alanyl]amino}-6-cyclohexyl-4-hydroxy-2-(1-hydroxy-1-methylethyl)-N-[2(S)-methylbutyl]hexanamide A mixture of 530 mg (1.16 mmoles) of (2S, 4S, 5S)-5-(t-butoxycarbonylamino)-6-cyclohexyl-4-hydroxy-2-(1-hydroxy-1-methylethyl)-N-[2(S)-methylbutyl]hexanamide (prepared as described in Preparation 7) in 10 ml of a 4N solution of hydrogen chloride in dioxane was stirred at room temperature for 30 minutes. At the end of this time, the solvent was removed by distillation under reduced pressure. Diethyl ether was added to the residue, and the solvent was again removed by distillation under reduced pressure. This operation was repeated in total three times, and then the residue was dried under vacuum for 8 hours. The dried material was suspended in 10 ml of anhydrous tetrahydrofuran, and then 350 mg (1.29 mmoles) of N-(t-butoxycarbonyl)-3-(4-thiazolyl)-L-alanine were added to the resulting suspension. Subsequently, 0.21 ml (1.38 mmoles) of 95% diethyl cyanophosphate (i.e. diethyl cyanophosphate of purity about 95%) and 0.36 ml (2.58 mmoles) of triethylamine were added to the resulting mixture, whilst ice-cooling, and under an atmosphere of nitrogen. The mixture was stirred for 6 hours, after which the solvent was removed by distillation under reduced pressure, and the residue was purified by medium pressure silica gel column chromatography (using a 20:1 by volume mixture of methylene chloride and methanol as eluent), to give 650 mg (yield 92%) of the title compound as white crystals, melting at 190°–193° C.

Elemental analysis: Calculated for $C_{31}H_{54}N_4O_6S$; C, 60.95%; H, 8.91%; N, 9.17%; 5, 5.25%. Found: C, 60.70%; H, 9.08%; N, 9.18%; S, 5.40%.

Mass spectrum (m/e): 610 (M+), 381, 212, 172, 127.

EXAMPLE 2

(2S, 4S, 5S)-5-{N-[N-Morpholinoacetyl-3-(1-naphthyl)-L-alanyl]-3-(4-thiazolyl)-L-alanyl}amino-6-cyclohexyl-4-hydroxy-2-(1-hydroxy-1-methylethyl)-N-[2(S)-methylbutyl]hexanamide A mixture of 150 mg (0.25 mmoles) of (2S, 4S, 5S)-5-{N-[N-(t-butoxycarbonyl)-3-(4-thiazolyl)-L-alanyl]amino}-6-cyclohexyl-4-hydroxy-2-(1-hydroxy-1-methylethyl)-N-[2(S)-methylbutyl]hexanamide (prepared as described in Example 1) in 5 ml of a 4N solution of hydrogen chloride in dioxane was stirred at room temperature for 30 minutes. At the end of this time, the solvent was removed by distillation under reduced pressure, and diethyl ether was added to the residue. The solvent was then again removed by distillation under reduced pressure. This operation was repeated in total three times, and then the final residue was dried under vacuum for 8 hours. The dried material was suspended in 10 ml of anhydrous tetrahydrofuran, and then 100 mg (0.29 mmoles) of N-morpholinoacetyl-3-(1-naphthyl)-L-alanine were added to the resulting suspension, followed by 0.04 ml (0.26 mmoles) of 95% diethyl cyanophosphate and 0.11 ml (0.79 mmoles) of triethylamine, all whilst ice-cooling and under an atmosphere of nitrogen. The mixture was then stirred for 8 hours, after which the solvent was removed by distillation under reduced pressure, and the residue was purified by silica gel thin layer chromatography (using a 10:1 by volume mixture of methylene chloride and methanol as eluent), to give 150 mg (yield 73%) of the title compound as white crystals, melting at 141°–143° C.

Elemental analysis: Calculated for $C_{45}H_{66}N_6O_7S \cdot 0.5 H_2O$: C, 64.03%; H, 8.00%; N, 9.96%; S, 3.80%. Found: C, 63.98%; H, 8.15%; N, 9.76%; S, 3.61%.

Mass spectrum (m/e): 798 (M+ $-2H_2O$).

EXAMPLE 3

(2S, 4S, 5S)-5-{N-[N-Morpholinoacetyl-L-phenylalanyl]-3-(4-thiazolyl)-L-alanyl}amino-6-cyclohexyl-4-hydroxy-2-(1-hydroxy-1-methylethyl)-N-[2(S)-methylbutyl]hexanamide Following a procedure similar to that described in Example 2, 156 mg (yield 81%) of the title compound, melting at 98°–101° C., were obtained as white crystals, using 86 mg (0.29 mmoles) of M-morpholinoacetyl-L-phenylalanine instead of the N-morpholinoacetyl-3-(1-naphthyl)-L-alanine.

Elemental analysis: Calculated for $C_{41}H_{64}N_6O_7S \cdot 0.5 H_2O$: C, 62.02%; H, 8.25%; N, 10.58%; S, 4.04%. Found: C, 62.07%; H, 8.41%; N, 10.38%; S, 3.95%.

Mass spectrum (m/e): 748 (M+ $-2H_2O$).

EXAMPLE 4

(2S, 4S, 5S)-5-{N-[2(R)-(1-Naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide Following a procedure similar to that described in Example 2, 131 mg (yield 65%) of the title compound were obtained as white crystals, melting at 102°–105° C., using 97 mg (0.30 mmoles) of 2(R)-(1-naphthylmethyl)-3-(morpholinocarbonyl)propionic acid instead of the N-morpholinoacetyl-3-(1-naphthyl)-L-alanine Elemental analysis: Calculated for $C_{45}H_{65}N_5O_7S \cdot H_2O$: C, 64.49%; H, 8.06%; N, 8.36%; 5, 3.83%. Found: C, 64.78%; H, 8.06%; N, 8.15%; S, 3.63%.

Mass spectrum (m/e): 801 (M+ $-H_2O$), 783 (M+ $-2H_2O$).

EXAMPLE 5

(2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide Following a procedure similar to that described in Example 2, 108 mg (yield 57%) of the title compound were obtained as white crystals, melting at 80°–82° C., using 82 mg (0.30 mmoles) of 2(R)-benzyl-3-(morpholinocarbonyl)propionic acid instead of the N-morpholinoacetyl-3-(1-naphthyl)-L-alanine.

Elemental analysis: Calculated for $C_{41}H_{63}N_5O_7S \cdot H_2O$: C, 62.49%; H, 8.31%; N, 8.89%; S, 4.07%. Found: C, 62.29%; H, 8.03%; N, 8.55%;

EXAMPLE 6

(2S, 4S, 5S)-5-{N-[N-(t-Butoxycarbonyl)-3-(4-thiazolyl)-L-alanyl]amino}-4-hydroxy-2-(1-hydroxy-1-methylethyl)-7-methyl-N-[2(RS)-methylbutyl]octanamide Following a procedure similar to that described in Example 1, a mixture of 260 mg (0.62 mmoles) of (3S, 5S)-5-[(1S)-1-(N-t-butoxycarbonylamino)-3-methylbutyl]-3-(1-hydroxy-1-methylethyl)dihydrofuran-2(3H)-one (prepared as described in Preparation 9) in 5 ml of a 4N solution of hydrogen chloride in dioxane was stirred at room temperature for 30 minutes. At the end of this time, the solvent was removed by distillation under reduced pressure, and diethyl ether was added to the residue. The solvent was then again removed by distillation under reduced pressure. This operation was repeated in total three times, after which the residue was dried under vacuum for 8 hours. At the end of this time, the dried material was suspended in 5 ml of anhydrous tetrahydrofuran, and 187 mg (0.69 mmoles) of N-(t-butoxycarbonyl)-3-(4-thiazolyl)-L-alanine were added to the resulting suspension, followed by 0.11 ml (0.73 mmoles) of 95% diethyl cyanophosphate and 0.19 ml (1.36 mmoles) of triethylamine, all whilst ice-cooling and under an atmosphere of nitrogen. The mixture was then stirred for 6 hours, after which the solvent was removed by distillation under reduced pressure, and the residue was purified by medium pressure silica gel column chromatography (using a 20:1 by volume mixture of methylene chloride and methanol as eluent), to give 303 mg (yield 85%) of the title compound as an amorphous substance.

Elemental analysis: Calculated for $C_{28}H_{50}N_4O_6S.0.5-H_2O$: C, 58.00%; H, 8.86%; N, 9.66%; S, 5.53%. Found: C, 57.82%; H, 8.71%; N, 9.54%; S, 5.69%.

Mass spectrum (m/e): 570 (M+).

EXAMPLE 7

(2S, 4S, 5S)-5-{N-[N-(t-Butoxycarbonyl)-3-(1-naphthyl)-L-alanyl]-3-(4-thiazolyl)-L-alanyl}amino-4-hydroxy-2-(1-hydroxy-1-methylethyl)-7-methyl-N-[2(RS)-methylbutyl]octanamide A mixture of 142 mg (0.25 mmoles) of (2S, 4S, 5S)-5-{N-[N-(t-butoxycarbonyl)-3-(4-thiazolyl)-L-alanyl]-}amino-4-hydroxy-2-(1-hydroxy-1-methylethyl)-7-methyl-N-[2(RS)-methylbutyl]octanamide (prepared as described in Example 6) in 5 ml of a 4N solution of hydrogen chloride in dioxane was stirred at room temperature for 30 minutes. At the end of this time, the solvent was removed by distillation under reduced pressure. Diethyl ether was then added to the residue, and the solvent was removed again by distillation under reduced pressure. This operation was repeated in total three times, after which the residue was dried under vacuum for 8 hours. At the end of this time, the dried material was suspended in 10 ml of anhydrous tetrahydrofuran, and 99.9 mg (0.32 mmoles) of N-t-butoxycarbonyl-3-(1 naphthyl)-L-alanine were added to the resulting suspension, followed by 0.05 ml (0.33 mmoles) of 95% diethyl cyanophosphate and 0.12 ml (0.86 mmoles) of triethylamine, all whilst ice-cooling and under an atmosphere of nitrogen, The mixture was then stirred for 8 hours, after which the solvent was removed by distillation under reduced pressure, and the residue was purified by silica gel thin layer chromatography (using a 10:1 by volume mixture of methylene chloride and methanol as developing solvent), to give 181 mg (yield 95%) of the title compound as white crystals, melting at 90°–92° C.

Elemental analysis: Calculated for $C_{41}H_{61}N_5O_7S.H_2O$: C, 62.65%; H, 8.08%; N, 8.91%; S, 4.08%. Found: C, 62.25%; H, 8.03%; N, 8.67%; S, 4.27%.

EXAMPLE 8

(2S, 4S, 5S)-5-{N-[2(R)-(1-Naphthylmethyl)-3-(N-cyclohexyl-N-methylaminocarbonyl)propionyl]-3-(4-thiazolyl)-L-alanyl}amino-4-hydroxy-2-(1-hydroxy-1-methylethyl)-7-methyl-N-[2-(RS)-methylbutyl]octanamide Following a procedure similar to that described in Example 7, 155 mg (yield 85%) of the title compound were obtained as white crystals, melting at 187°–190° C., using 122 mg (0.23 mmoles) of (2S, 4S, 5S)-5-{N-[N-(t-butoxycarbonyl)-3-(4-thiazolyl)-L-alanyl]amino}-4-hydroxy-2-(1-hydroxy-1-methylethyl)-7-methyl-N-[2(RS)-methylbutyl]octanamide (prepared as described in Example 6) and 89 mg (0.25 mmoles) of 2(R)-(1-naphthylmethyl)-3-(N-cyclohexyl-N-methylaminocarbonyl)propionic acid instead of the N-t-butoxycarbonyl-3-(1-naphthyl)-L-alanine used in Example 7.

Elemental analysis: Calculated for $C_{45}H_{67}N_5O_6S.H_2O$: C, 65.58%; H, 8.44%; N, 8.50%; S, 3.89%. Found: C, 65.70%; H, 8.67%; N, 8.23%; S, 3.93%.

EXAMPLE 9

(2S, 4S, 5S)-5-{N-[2(R)-Benzyl-3-(morpholinocarbonyl)propionyl)]-3-(4-thiazolyl)-L-alanyl}amino-6-cyclohexyl-4-hydroxy-2-(1-hydroxy-1-methylethyl)-N-methylhexanamide

9(a) (2S, 4S, 5S)-5-[N-(t-Butoxycarbonyl)-3-(4-thiazolyl)-L-alanyl-]amino-6-cyclohexyl-4-hydroxy-2-(1-hydroxy-1-methylethyl)-N-methylhexanamide A mixture of 1.20 g (3.00 mmoles) of (2S, 4S, 5S)-5-(t-butoxycarbonylamino)-6-cyclohexyl-4-hydroxy-2-(1-hydroxy-1-methylethyl)-N-methylhexanamide (prepared as described in Preparation 23) in 20 ml of a 4N solution of hydrogen chloride in dioxane was stirred at room temperature for 30 minutes under an atmosphere of nitrogen. At the end of this time, the reaction mixture was concentrated by evaporation under reduced pressure, and then diethyl ether was added to the residue. The solvent was then removed by distillation under reduced pressure from the resulting solution. The same operation was repeated in total three times, and the residue was then dried under reduced pressure for 8 hours. At the end of this time, 900 mg (3.30 mmoles) of N-(t-butoxycarbonyl)-3-(4-thiazolyl)-L-alanine were added to a suspension of the dried material in 20 ml of anhydrous tetrahydrofuran, and then 0.50 ml (3.30 mmoles) of diethyl cyanophosphate and 0.92 ml (6.60 mmoles) of triethylamine were added to the resulting mixture, whilst ice-cooling and under an atmosphere of nitrogen. The mixture was then stirred for 5 hours, after which the solvent was removed by distillation under reduced pressure, and the residue was purified by medium pressure silica gel column chromatography (using a 20:1 by volume mixture of methylene chloride and methanol as eluent), followed by recrystallization from diisopropyl ether, to give 1.51 g (yield 91%) of the title compound as white crystals, melting at 203°–205° C.

$[\alpha]_D^{20} = -40.9°$ (C=1, methanol).

Elemental analysis: Calculated for $C_{27}H_{46}N_4O_6S$; C, 58.46%; H, 8.36%; N, 10.10%; S, 5.78%. Found: C, 58.12%; H, 8.21%; N, 9.84%; S, 5.79%.

Mass spectrum (m/e): 555 (M++1), 307, 224, 181, 127.

9(b) (2S, 4S, 5S)-5-{N-[2(R)-Benzyl-3-(morpholinocarbonyl)propionyl]-3-[4-thiazolyl]-L-alanyl}amino-6-cyclohexyl-4-hydroxy-2-(1-hydroxy-1-methylethyl)-N-methylhexanamide A mixture of 500 mg (0.90 mmoles) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-methylhexanamide [prepared as described in Example 9(a)] in 10 ml of a 4N solution of hydrogen chloride in dioxane was stirred at room temperature and under an atmosphere of nitrogen for 30 minutes, and then the reaction mixture was concentrated by evaporation under reduced pressure. Diethyl ether was added to the residue, and then the solvent was removed by distillation under reduced pressure. The same operation was repeated in total three times. The resulting residue was dried by evaporation under reduced pressure for 8 hours, and then the residue was suspended in 10 ml of anhydrous tetrahydrofuran. 275 mg (0.92 mmoles) of 2(R)-benzyl-3-(morpholinocarbonyl)propionic acid were added to the suspension, and then 0.15 ml (0.99 mmoles) of diethyl cyanophosphate and 0.42 ml (3.01 mmoles) of triethylamine were added to the resulting mixture, whilst ice-cooling and under an atmosphere of nitrogen. The mixture was then stirred for 8 hours, after which the solvent was removed by distillation under reduced pressure and the residue was purified by silica gel thin layer chromatography (using an 8:1 by volume mixture of methylene chloride and methanol as the developing solvent) and then recrystallization of the product from ethyl acetate, to give 500 mg (yield 78%) of the title compound as white crystals, melting at 150°-152° C.

$[\alpha]_D^{20} = -35.9°$ (C=1, methanol).

Elemental analysis: Calculated for $C_{37}H_{55}N_5O_7S \cdot 0.5\text{-}H_2O$: C, 61.47%; H, 7.81%; N, 9.69%; S, 4.43%. Found: C, 61.49%; H, 7.80%; N, 9.60%; S, 4.55%.

EXAMPLE 10

(2S, 4S, 5S)-5-{N-[2(R)-(4-Methoxybenzyl)-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide A mixture of 400 mg (0.72 mmoles) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-methylhexanamide [prepared as described in Example 9(a)] in 8 ml of a 4N solution of hydrogen chloride in dioxane was stirred at room temperature and under an atmosphere of nitrogen for 30 minutes, after which the reaction mixture was concentrated by evaporation under reduced pressure. Diethyl ether was added to the residue, and then the solvent was again removed by distillation under reduced pressure. The same operation was repeated in total three times. The resulting residue was dried by evaporation under reduced pressure for 8 hours, and then the resulting residue was suspended in 10 ml of anhydrous tetrahydrofuran. 244 mg (yl) 0.79 mmoles) of 2(R)-(4-methoxybenzyl)-3-(morpholinocarbonyl)propionic acid (prepared as described in Preparation 15) were added to the suspension, and then 0.12 ml (0.79 mmoles) of diethyl cyanophosphate and 0.33 ml (2.37 mmoles) of triethylamine were added to the resulting mixture, whilst ice-cooling and under an atmosphere of nitrogen. The mixture was then stirred for 8 hours, after which the solvent was removed by distillation under reduced pressure, and the residue was purified by silica gel thin layer chromatography (using an 8:1 by volume mixture of methylene chloride and methanol as the developing solvent), to give 440 mg (yield 82%) of the title compound as an amorphous substance.

$[\alpha]_D^{20} = -33.8°$ (C=1, methanol).

Elemental analysis: Calculated for $C_{38}H_{57}N_5O_8S \cdot H_2O$: C, 59.90%; H, 7.80%; N, 9.19%: S, 4.21%. Found: C, 59.86%; H, 7.76%; N, 8.88%; S, 4.14%.

EXAMPLE 11

(2S, 4B, 5S)-5-{N-[2(R)-Benzyl-4-oxopentanoyl]-3-(4-thiazolyl)-L-alanyl}amino-6-cyclohexyl-4-hydroxy-2-(1-hydroxy-1-methylethyl)-N-methylhexanamide A mixture or 192 mg (0.35 mmoles) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-methylhexanamide [prepared as described in Example 9(a)] in 2 ml of a 4N solution of hydrogen chloride in dioxane was stirred at room temperature under an atmosphere of nitrogen for 30 minutes. At the end of this time, the reaction mixture was concentrated by evaporation under reduced pressure. Diethyl ether was added to the residue, and the solvent was again removed by distillation under reduced pressure. The same operation was repeated, in total, three times. The resulting residue was dried by evaporation under reduced pressure for 8 hours, and was then suspended in 5 ml of anhydrous tetrahydrofuran. 86 mg (0.42 mmoles) of 2(R)-benzyl-4-oxopentanoic acid (prepared as described in Preparation 20) were then added to the suspension, after which 0.06 ml (0.40 mmoles) of diethyl cyanophosphate and 0.16 ml (1.15 mmoles) of triethylamine were added to the mixture, whilst ice-cooling and under an atmosphere of nitrogen. The mixture was then stirred for 3 hours, after which the solvent was removed by distillation under reduced pressure, and the resulting residue was purified by silica gel thin layer chromatography (using an 8:1 by volume mixture of methylene chloride and methanol as the developing solvent), to give 164 mg (yield 74%) of the title compound as an amorphous substance.

$[\alpha]_D^{20} = -40.0°$ (C=1, methanol).

Elemental analysis: Calculated for $C_{34}H_{50}N_4O_6S \cdot H_2O$: C, 61.79%; H, 7.93%; N, 8.48%; S, 4.85%. Found: C, 62.26%: H, 7.84%; N, 8.08%; S, 4.48%.

EXAMPLE 12

(2S, 4S, 5S)-5-{N-[2(R)-(1-Naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-methylhexanamide A procedure similar to that described in Example 2 was repeated, except that 100 mg (0.17 mmoles) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-methylhexanamide [prepared as described in Example 9(a)], 71 mg (0.22 mmoles) of 2(R)-(1-naphthylmethyl)-3-(morpholinocarbonyl)propionic acid, 0.03 ml (0.20 mmoles) of diethyl cyanophosphate, and 0.08 ml (0.57 mmoles) of triethylamine were used, obtain 104 mg (yield 75%) of the title compound as an amorphous substance.

$[\alpha]_D^{20} = -23.0°$ (C=0.2, methanol).

Elemental analysis: Calculated for $C_{41}H_{57}N_5O_7S \cdot 3H_2O$: C, 60.19%; H, 7.76%; N, 8.56%; 3.92%. Found: C, 60.53; H, 7.45; N, 8.35; S, 3.56%.

EXAMPLE 13

(2S, 4S, 5S)-5-{N-[N-Morpholinoacetyl-L-phenylalanyl]-3-(4-thiazolyl)-L-alanyl}amino-6-cyclohexyl-4-hydroxy-2-(1-hydroxy-1-methylethyl)-N-methylhexanamide A procedure similar to that described in Example 2 was repeated, except that 100 mg (0.18 mmoles) of (2S, 4S, 5S)-5-[N-(t-butoxycarbonyl) 3-(4-thiazolyl)-L-alanyl]amino-6-cyclohexyl-4-hydroxy-2-(1-hydroxy-1-methylethyl)-N-methylhexanamide [prepared as described in Example 9(a)], 58 mg (0.20 mmoles) of N-morpholinoacetyl-L-phenylalanine, 0.03 ml (0.20 mmoles) of diethyl cyanophosphate, and 0.08 ml (0.57 mmoles) of triethylamine were used, to obtain 101 mg (yield 77%) of the title compound as a white amorphous substance.

$[\alpha]_D^{20} = -22.2°$ (C=0.5, methanol).

Elemental analysis: Calculated for $C_{37}H_{56}N_6O_7S \cdot H_2O$: C, 59.49%; H, 7.83%; N, 11.25%; 4.29%. Found: C, 59.70%; H, 7.74%; N, 11.31%; 4.39%.

EXAMPLE 14

(2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N-ethylhexanamide 14(a) (2S, 4S, 5S)-5-[N-(t-Butoxycarbonyl)-3-(4-thiazolyl)-L-alanyl-]amino-6-cyclohexyl-4-hydroxy-2-(1-hydroxy-1-methylethyl)-N-ethylhexanamide A procedure similar to that described in Example 9(a) was repeated, except that 280 mg (0.675 mmoles) of (2S, 4S, 5S)-5-(t-butoxycarbonylamino)-6-cyclohexyl-4-hydroxy-2-(1-hydroxy-1-methylethyl)-N-ethylhexanamide (prepared as described in Preparation 24) were used instead of the (2S, 4S, 5S)-5-(t-butoxycarbonylamino)-6-cyclohexyl-4-hydroxy-2-(1-hydroxy-1-methylethyl)-N-methylhexanamide, and 190 mg (0.7 mmoles) of N-(t-butoxycarbonyl)-3-(4-thiazolyl)-L-alanine, 0.4 ml (2.88 mmoles) of triethylamine, and 0.11 ml (0.688 mmoles) of diethyl cyanophosphate were also used, to give a powdery substance, which was then recrystallized from a mixture of diisopropyl ether and methylene chloride, to afford 309 mg of the title compound, melting at 189°-191° C.

14(b) (2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N-ethylhexanamide A procedure similar to that described in Example 2 was repeated, except that 100 mg (0.176 mmoles) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-ethylhexanamide [prepared as described in Example 14(a)], 50 mg (0.18 mmoles) of 2(R)-benzyl-3-(morpholinocarbonyl)propionic acid, 0.28 ml (2 mmoles) of triethylamine, and 0.029 ml (0.18 mmoles) of diethyl cyanophosphate were used, to obtain 41 mg of the title compound.

Elemental analysis: Calculated for $C_{38}H_{57}N_5O_7S \cdot H_2O$: C, 61.18%; H, 7.97%; N, 9.38%; 4.30%. Found: C, 61.05%; H, 7.89%; N, 9.11%; 4.41%.

EXAMPLE 15

(2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N,N-dimethylhexanamide 15(a) (2S, 4S, 5S)-5-[N-(t-Butoxycarbonyl)-3-(4-thiazolyl)-L-alanyl-]amino-6-cyclohexyl-4-hydroxy-2-(1-hydroxy-1-methylethyl)-N,N-dimethylhexanamide A procedure similar to that described in Example 9(a) was repeated, except that 152 mg of (2S, 4S, 5S)- 5-(t-butoxycarbonylamino)-6-cyclohexyl-4-hydroxy-2-(1-hydroxy-1-methylethyl)-N,N-dimethylhexanamide (prepared as described in Preparation 25) were used instead of the (2S, 4S, 5S)-5-(t-butoxycarbonylamino)-6-cyclohexyl-4-hydroxy-2-(1-hydroxy-1-methylethyl)-N-methylhexanamide, and that 109 mg (0.4 mmoles) of N-(t-butoxycarbonyl)-3-(4-thiazolyl)-L-alanine, 0.23 ml (1.66 mmoles) of triethylamine, and 0.064 ml (0.4 mmoles) of diethyl cyanophosphate were also used, to obtain 150 mg of the title compound as a white amorphous substance.

15(b) (2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N,N-dimethylhexanamide A procedure similar to that described in Example 2 was repeated, except that 100 mg (0.176 mmoles) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N,N-dimethylhexanamide [prepared as described in Example 15(a)], 50 mg (0.18 mmoles) of 2(R)-benzyl-3-(morpholinocarbonyl)propionic acid, 0.28 ml (2 mmoles) of triethylamine, and 0.029 ml (0.18 mmoles) of diethyl cyanophosphate were used, to obtain 45 mg of the title compound as a white powder.

Elemental analysis: Calculated for $C_{38}H_{57}N_5O_7S \cdot H_2O$: C, 61.18%; H, 7.97%; N, 9.38%; 4.30%. Found: C, 61.29%; H, 7.91%; N, 8.27%; 3.77%.

EXAMPLE 16

(2S, 4S, 5S)-5-{N-[2(R)-(1-Naphthylmethyl)-3-(morpholinocarbonyl)propionyl]-3-(4-thiazolyl)-L-alanyl}amino-4-hydroxy-2-(1-hydroxy-1-methylethyl)-7-methyl-N-methyloctanamide 16(a) (2S, 4S, 5S)-5-[N-(t-Butoxycarbonyl)-3-(4-thiazolyl)-L-alanyl-]amino-4-hydroxy-2-(1-hydroxy-1-methylethyl)-7-methyl-N-methyloctanamide A mixture of 274 mg (0.76 mmoles) of (2S, 4S, 5S)-5-(t-butoxycarbonylamino)-4-hydroxy-2-(1-hydroxy-1-methylethyl)-7-methyl-N-methyloctanamide (prepared as described in Preparation 28) in 5 ml of a 4N solution of hydrogen chloride in dioxane was stirred at room temperature and under an atmosphere of nitrogen for 30 minutes. At the end of this time, the reaction mixture was concentrated by evaporation under reduced pressure. Diethyl ether was added to the residue, and the solvent was again removed by distillation under reduced pressure. The same operation was repeated, in total, three times. The resulting residue was then dried by evaporation under reduced pressure for 8 hours, after which it was suspended in 5 ml of anhydrous tetrahydrofuran. 248 mg (0.91 mmoles) of N-(t-butoxycarbonyl)-3-(4-thiazolyl)-L-alanine were then added to the suspension, after which 0.14 ml (0.92 mmoles) of diethyl cyanophosphate and 0.23 ml (1.65 mmoles) of triethylamine were added to the mixture, whilst ice-cooling and under an atmosphere of nitrogen. The mixture was then stirred for 5 hours, after which the solvent was removed by distillation under reduced pressure, and the resulting residue was purified by medium pressure silica gel column chromatography (using a 20:1 by volume mixture of methylene chloride and methanol as eluent), followed by recrystallization from hexane to give 356 mg (yield 91%) of the title compound as a white amorphous substance.

$[\alpha]_D^{20} = -33.5°$ (C=1, methanol).

Elemental analysis: Calculated for $C_{24}H_{42}N_4O_6S$: C, 56.01%; H, 8.23%; N, 10.89%; S, 6.23%. Found: C, 55.67%; H, 8.54%; N, 10.61%; S, 6.15%.

Mass spectrum (m/e): 515 (M$^+$+1), 341, 285, 199, 127.

16(b) (2S, 4S, 5S)-5-{N-[2(R)-(1-Naphthylmethyl)-3-(morpholinocarbonyl)propionyl]-3-(4-thiazolyl)-L-alanyl}amino-4-hydroxy-2-(1-hydroxy-1-methylethyl)-7-methyl-N-methyloctanamide A procedure similar to that described in Example 2 was repeated, except that 156 mg (0.30 mmoles) of 4S, 5S)-5-[N-(t-butoxycarbonyl)-3-(4-thiazolyl)-L-alanyl]amino-4-hydroxy-2-(1-hydroxy-1-methylethyl)-7-methyl-N-methyl octanamide [prepared as described in Example 16(a)], 119 mg (0.36 mmoles) of 2(R)-(1-naphthylmethyl)-3-(morpholinocarbonyl)propionic acid, 0.06 ml (0.40 mmoles) of diethyl cyanophosphate, and 0.14 ml (1.00 mmoles) of triethylamine were used, to obtain 205 mg (yield 94%) of the title compound as a white amorphous substance.

$[\alpha]_D^{20} = -23.6°$ (C=0.5, methanol).

Elemental analysis: Calculated for $C_{38}H_{55}N_5O_7S$.3-$H_2O$: C, 58.67%; H, 7.64%; N, 9.00%; S, 4.15%. Found: C, 58.44%; H, 7.21%; N, 8.82%; S, 3.89%.

EXAMPLE 17

(2S, 4S, 5S)-5-[N-(N-Morpholinoacetyl-L-phenylalanyl)-3-(4-thiazolyl)-L-alanyl]amino-4-hydroxy-2-(1-hydroxy-1-methylethyl)-7-methyl-N-methyloctanamide A procedure similar to that described in Example 2 was repeated, except that 100 mg (0.19 mmoles) of (2S, 4S, 5S)-5-[N-(t-butoxycarbonyl)-3-(4-thiazolyl)-L-alanyl]amino-4-hydroxy-2-(1-hydroxy-1-methylethyl)-7-methyl-N-methyloctanamide [prepared as described in Example 16(a)], 62 mg (0.21 mmoles) of N-morpholinoacetyl-L-phenylalanine, 0.03 ml (0.20 mmoles) of diethyl cyanophosphate, and 0.08 ml (0.57 mmoles) of triethylamine were used, to obtain 104 mg (yield 78%) of the title compound as a white amorphous substance.

$[\alpha]_D^{20} = -18.6°$ (C=0.5, methanol).

Elemental analysis: Calculated for $C_{34}H_{52}N_6O_7S$.$H_2O$: C, 57.77%; H, 7.70%; N, 11.89%; S, 4.54%. Found: C, 57.30%; H, 7.75%; N, 11.65%; S, 4.32%.

EXAMPLE 18

(2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-ethyl-1-hydroxypropyl)-N-methylhexanamide

18(a) (2S, 4S, 5S)-5-[N-(t-Butoxycarbonyl)-3-(4-thiazolyl)-L-alanyl]amino,6-cyclohexyl-4-hydroxy-2-(1-ethyl-1-hydroxypropyl)-N-methylhexanamide A mixture of 338 mg (0.79 mmoles) of (2S, 4S, 5S)-5-(t-butoxycarbonylamino)-6-cyclohexyl-2-(1-ethyl-1-hydroxypropyl)-N-methylhexanamide (prepared as described in Preparation 26) in 8 ml of a 4N solution of hydrogen chloride in dioxane was stirred at room temperature and under an atmosphere of nitrogen for 30 minutes. At the end of this time, the reaction mixture was concentrated by evaporation under reduced pressure. Diethyl ether was added to the residue, and the solvent was again removed by distillation under reduced pressure. The same operation was repeated, in total, three times. The residue was then dried by evaporation under reduced pressure for 8 hours, after which it was suspended in 10 ml of anhydrous tetrahydrofuran. 258 mg (0.95 mmoles) of N-(t-butoxycarbonyl)-3-(4-thiazolyl)-L-alanine were added to the suspension, and then 0.14 ml (0.92 mmoles) of diethyl cyanophosphate and 0.24 ml (1.72 mmoles) of triethylamine were added to the resulting mixture, whilst ice-cooling and under an atmosphere of nitrogen. The mixture was then stirred for 5 hours, after which the solvent was removed by distillation under reduced pressure, and the residue was purified by medium pressure silica gel column chromatography (using a 20:1 by volume mixture of methylene chloride and methanol as eluent), followed by recrystallization from hexane, to give 430 mg (yield 94%) of the title compound as white crystals, melting at 165°-168° C.

$[\alpha]_D^{20} = -32.3°$ (C=1, methanol).

Elemental analysis: Calculated for $C_{29}H_{50}N_4O_6S$: C, 59.77%: H, 8.65%; N, 9.61%: S, 5.50%. Found: C, 59.48%: H, 8.72%; N, 9.44%; S, 5.58%.

Mass spectrum (m/e): 583 (M$^+$+1), 381, 127.

18(2S, 4S, 5S)-S-{N-[2(R)-Benzyl-3-(morpholinocarbonyl)propionyl]-3-(4-thiazolyl)-L-alanyl}amino-6-cyclohexyl-4-hydroxy-2-(1-ethyl-1-hydroxypropyl)-N-methylhexanamide A mixture of 120 mg (0.21 mmoles) of (2S, 4S, 5S)-5-[N-(t-butoxycarbonyl)-3-(4-thiazolyl)-L-alanyl]amino-6-cyclohexyl-4-hydroxy-2-(1-ethyl-1-hydroxypropyl)-N-methylhexanamide [prepared as described in Example 18(a)] in 4 ml of a 4N solution of hydrogen chloride in dioxane was stirred at room temperature and under an atmosphere of nitrogen for 30 minutes. At the end of this time, the reaction mixture was concentrated by evaporation under reduced pressure. Diethyl ether was added to the residue, and the solvent was again removed by distillation under reduced pressure. The same operation was repeated, in total, three times, after which the residue was dried by evaporation under reduced pressure for 8 hours. At the end of this time, the dried material was suspended in 5 ml of anhydrous tetrahydrofuran, and 69 mg (0.25 mmoles) of 2(R)-benzyl-3-(morpholinocarbonyl)propionic acid were added to the suspension. 0.04 ml (0.26 mmoles) of diethyl cyanophosphate and 0.09 ml (0.65 mmoles) of triethylamine were then added to the solution, whilst ice-cooling and under art atmosphere of nitrogen. The mixture was then stirred for 8 hours, after which the solvent was removed by distillation under reduced pressure, and the residue was purified by silica gel thin layer chromatography (using an 8:1 by volume mixture of methylene chloride and methanol as the developing solvent), to give 117 mg (yield 77%) of the title compound as a white amorphous substance.

$[\alpha]_D^{20} = -30.6°$ (C=0.5 methanol).

Elemental analysis: Calculated for $C_{39}H_{59}N_5O_7S \cdot 2H_2O$: C, 60.21%; H, 8.16%; N, 9.00%; 4.12%. Found: C, 60.20%; H, 8.00%; N, 8.80%; 3.89%.

EXAMPLE 19

(2S, 4S, 5S)-5-{N-[2(R)-(1-Naphthylmethyl)-3-(morpholinocarbonyl)propionyl]-3-(4-thiazolyl)-L-alanyl}amino-6-cyclohexyl-4-hydroxy-2-(1-ethyl-1-hydroxypropyl)-N-methylhexanamide A procedure similar to that described in Example 2 was repeated, except that 120 mg (0.21 mmoles) of (2S, 4S, 5S)-5-[N-(t-butoxycarbonyl)-3-(4-thiazolyl)-L-alanyl]amino-6-cyclohexyl-4-hydroxy-2-(1-ethyl-1-hydroxypropyl)-N-methylhexanamide [prepared as described in Example 18(a)], 81 mg (0.25 mmoles) of 2(R)-(1-naphthylmethyl)-3-(morpholinocarbonyl)propionic acid, 0.04 ml (0.26 mmoles) of diethyl cyanophosphate, and 0.09 ml (0.65 mmoles) of triethylamine were used, to obtain 144 mg (yield 88%) of the title compound as a white amorphous substance.

$[\alpha]_D^{20} = -25.4°$ (C=0.5, methanol).

Elemental analysis: Calculated for $C_{43}H_{61}N_5O_7S \cdot 3H_2O$: C, 61.04%; H, 7.98%; N, 8.28%; 3.79%. Found: C, 61.19%; H, 7.68%; N, 8.15%; 3.60%.

EXAMPLE 20

(2S, 4S, 5S)-5-[N-(N-Morpholinoacetyl-L-phenylalanyl)-3-(4-thiazolyl)-L-alanyl]amino-6-cyclohexyl-4-hydroxy-2-(1-ethyl-1-hydroxypropyl)-N-methylhexanamide A procedure similar to that described in Example 2 was repeated, except that 100 mg (0.17 mmoles) of (2S, 4S, 5S)-5-[N-(t-butoxycarbonyl)-3-(4-thiazolyl)-L-alanyl]amino-6-cyclohexyl-4-hydroxy-2-(1-ethyl-1-hydroxypropyl)-N-methylhexanamide [prepared as described in Example 18(a)], 55 mg (0.19 mmoles) of N-morpholinoacetyl-L-phenylalanine, 0.03 ml (0.20 mmoles) of diethyl cyanophosphate, and 0.08 ml (0.57 mmoles) of triethylamine were used, to obtain 103 mg (yield 79%) of the title compound as a white amorphous substance.

$[\alpha]_D^{20} = -20.0°$ (C=0.5, methanol).

Elemental analysis: Calculated for $C_{39}H_{60}N_6O_7S \cdot H_2O$: C, 60.44%; H, 8.06%; N, 10.84%; 4.14%. Found: C, 60.41%: H, 8.08%; N, 10.63%;

EXAMPLE 21

(2S, 4S, 5S)-5-{N-[2(R)-(1-Naphthylmethyl)-3-(morpholinocarbonyl)propionyl]-3-(4-thiazolyl)-L-alanyl}amino-6-cyclohexyl-4-hydroxy-2-(1-hydroxycyclohexyl)-N-methylhexanamide

21(a) (2S, 4S, 5S)-[N-(t-Butoxycarbonyl)-3-(4-thiazolyl)-L-alanyl]amino-6-cyclohexyl-4-hydroxy-2-(1-hydroxycyclohexyl)-N-methylhexanamide A mixture of 265 mg (0.60 mmoles) of (2S, 4S, 5S)-5-(t-butoxycarbonylamino)-6-cyclohexyl-4-hydroxy-2-(1-hydroxycyclohexyl)-N-methylhexanamide (prepared as described in Preparation 27) in 8 ml of a 4N solution of hydrogen chloride in dioxane was stirred at room temperature and under an atmosphere of nitrogen for 30 minutes. At the end of this time, the reaction mixture was concentrated by evaporation under reduced pressure. Diethyl ether was added to the residue, and the solvent was removed again by distillation under reduced pressure, The same operation was repeated, in total, three times, after which the residue was dried by evaporation under reduced pressure for 8 hours. At the end of this time, the dried material was suspended in 10 ml of anhydrous tetrahydrofuran, and 197 mg (0.72 mmoles) of N-(t-butoxycarbonyl)-3-(4-thiazolyl)-L-alanine were added to the resulting suspension, followed by 0.11 ml (0.73 mmoles) of diethyl cyanophosphate and 0.18 ml {1.29 mmoles) of triethylamine, all whilst ice-cooling and under an atmosphere of nitrogen. The mixture was then stirred for 5 hours, after which the solvent was removed by evaporation under reduced pressure, and the residue was purified by medium pressure silica gel column chromatography (using a 20:1 by volume mixture of methylene chloride and methanol as eluent), followed by recrystallization from hexane, to give 300 mg (yield 84%) of the title compound as white crystals, melting at 203°-205° C.

$[\alpha]_D^{20} = -38.1°$ (C=1, methanol).

Elemental analysis: Calculated for $C_{30}H_{50}N_4O_6S$: C, 60.58%; H, 8.47%; N, 9.42%; S, 5.39%. Found: C, 60.27%; H, 8.70%; N, 9.40%; B, 5.32%.

Mass spectrum (m/e): 595 (M++1), 381, 127.

21(b) (2S, 4S, 5S)-5-{N-[2(R)-(1-Naphthylmethyl)-3-(morpholinocarbonyl)propionyl]-3-(4-thiazolyl)-L-alanyl}amino-6-cyclohexyl-4-hydroxy-2-(1-hydroxycyclohexyl)-N-methylhexanamide A procedure similar to that described in Example 2 was repeated, except that 147 mg (0.25 mmoles) of (2S, 4S, 5S)-[N-(t-butoxycarbonyl)-3-(4-thiazolyl)-L-alanyl]amino-6-cyclohexyl-4-hydroxy-2-(1-hydroxycyclohexyl)-N-methylhexanamide [prepared as described in Example 21(a)], 97 mg (0.30 mmoles) of 2(R)-(1-naphthylmethyl)-3-(morpholinocarbonyl)propionic acid, 0.04 ml (0.26 mmoles) of diethyl cyanophosphate, and 0.11 ml (0.79 mmoles) of triethylamine were used, to obtain 170 mg (yield 85%) of the title compound as a white amorphous substance.

$[\alpha]_D^{20} = -23.4°$ (C=0.5, methanol).

Elemental analysis: Calculated for $C_{44}H_{61}N_5O_7S \cdot 2.5H_2O$: C, 62.24%; H, 7.83%; N, 8.25%; .78%. Found: C, 62.05%; H, 7.48%; N, 7.90%; .64%.

EXAMPLE 22

(2S, 4S, 5S)-5-[N-(N-Morpholinoacetyl-L-phenylalanyl)-3-(4-thiazolyl)-L-alanyl]amino-6-cyclohexyl-4-hydroxy-2-(1-hydroxycyclohexyl)-N-methylhexanamide A procedure similar to that described in Example 2 was repeated, except that 100 mg (0.17 mmoles) of (2S, 4S, 5S)-[N-(t-butoxycarbonyl)-3-(4-thiazolyl)-L-alanyl-]amino-6-cyclohexyl-4-hydroxy-2-(1-hydroxycyclohexyl)-N-methylhexanamide [prepared as described in Example 21(a)], 5.0 mg (0.17 mmoles) of N-morpholinoacetyl-L-phenylalanine, 0.03 ml (0.20 mmoles) of diethyl cyanophosphate, and 0.08 ml (0.57 mmoles) of triethylamine were used, to obtain 98 mg (yield 76%) of the title compound as a white amorphous substance.

$[\alpha]_D^{20} = -26.4°$ (C=0.5, methanol).

Elemental analysis: Calculated for $C_{40}H_{60}N_6O_7S \cdot H_2O$: C, 61.04%; H, 7.94%; N, 10.68%; 4.07%. Found: C, 61.02%; H, 8.03%; N, 10.53%; 4.00%.

EXAMPLE 23

(2S, 4S, 5S)-5-{N-[2(R)-Benzyl-3-(N-cyclohexyl-N-methylaminocarbonyl)propionyl]-3-(4-thiazolyl)-L-alanyl}amino-6-cyclohexyl-4-hydroxy-2-(1-hydroxy-1-methylethyl)-N-methylhexanamide Following a procedure similar to that described in Example 9(b), 65.mg of the title compound were obtained, as white crystals, from 100 mg (0.18 mmole) of (2S, 4S, 5S)-5-[N-(t-butoxycarbonyl)-3-(4-thiazolyl)-L-alanyl]amino -6-cyclohexyl-4-hydroxy-2-(1-hydroxy-1-methylethyl) -N-methylhexanamide [prepared as described in Example 9(a )] and 60 mg (0.198 mmole) of 2(R)-benzyl-3-(N-cyclohexyl-N-methylaminocarbonyl)propionic acid, instead of the 2(R)-benzyl-3-(morpholinocarbonyl)propionic acid used in Example 9(b).

Elemental Analysis: Calculated for $C_{40}H_{61}N_5O_6S \cdot 0.5H_2O$: C, 64.14%; H, 8.34%; N, 9.35%; S, 4.28%. Found: C, 64.22%; H, 8.27%; N, 9.31%; S, 4.17%.

EXAMPLE 24

(2S, 4S, 5S)-5-{N-[2(R)-Benzyl-3-(N-benzyl-N-methylaminocarbonyl)propionyl]-3-(4-thiazolyl)-L-alanyl}amino-6-cyclohexyl-4-hydroxy-2-(1-hydroxy-1-methylethyl)-N-methylhexanamide Following a procedure similar to that described in Example 9(b), 74 mg of the title compound were obtained as a white powder, from 100 mg (0.18 mmole) of (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-methylhexanamide [prepared as described in Example 9(a)] and 61.7 mg (0.198 mmole) of 2(R)-benzyl-3-(N-benzyl-N-methylaminocarbonyl)propionic acid, instead of the 2(R)-benzyl-3-(morpholinocarbonyl)propionic acid used in Example 9(b).

Elemental Analysis: Calculated for $C_{41}H_{57}N_5O_6S \cdot H_2O$: C, 64.29%; H, 7.76%; N, 9.14%: S, 4.19%. Found: C, 64.48%: H, 7.67%: N, 8.43%: S, 3.70%.

EXAMPLE 25

(2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N-butylhexanamide

25(a) (2S, 4S, 5S)-5-[N-(t-butoxycarbonyl)-3-(4-thiazolyl)-L-alanyl]amino-6-cyclohexyl-4-hydroxy-2-(1-hydroxy-1-methylethyl)-N-butylhexanamide A mixture of 309 mg (0.698 mmole) of (2S, 4S, 5S)-5-(t-butoxycarbonylamino)-6-cyclohexyl-4-hydroxy-2-(1-hydroxy-1-methylethyl)-N-butylhexanamide (prepared as described in Preparation 29) in 6 ml of a 4N solution of hydrogen chloride in dioxane was stirred at room temperature for 30 minutes under an atmosphere of nitrogen. At the end of this time, the reaction mixture was concentrated by evaporation under reduced pressure, and then benzene was added to the residue. The solvent was removed by distillation under reduced pressure from the resulting solution. The same operation was repeated, in total, three times, and the resulting residue was then dried by evaporation under reduced pressure for 8 hours. At the end of this time, 200.6 mg (0.737 mmole) of N-(t-butoxycarbonyl)-3-(4-thiazolyl)-L-alanine were added to a suspension of the dried material in 15 ml of anhydrous tetrahydrofuran, and then 0.13 ml (0.858 mmole) of 95% diethyl cyanophosphate and 0.3 ml of triethylamine were added to the resulting mixture, whilst ice-cooling and under an atmosphere of nitrogen. The mixture was then stirred for 5 hours, after which the solvent was removed by distillation under reduced pressure and the residue was purified by medium pressure silica gel column chromatography (using a 20:1 by volume mixture of methylene chloride and methanol as eluent), followed by recrystallization from a mixture of methylene chloride and diisopropyl ether, to give 457.8 mg or the title compound as white crystals.

25(b) (2S, 4S, 5S)-5-{N-[2(R)-Benzyl-3-(morpholinocarbonyl)propionyl]-3-(4-thiazolyl)-L-alanyl}amino-6-cyclohexyl-4-hydroxy-2-(1-hydroxy-1-methylethyl)-N-butylhexanamide A mixture of 200.7 mg (0.336 mmole) of (2S, 4S, 5S)-5-[N-(t-butylcarbonyl)-3-(4-thiazolyl)-L-alanyl]amino-6-cyclohexyl-4-hydroxy-2-(1-hydroxy-1-methylethyl)-N-butylhexanamide in 6 ml of a 4N solution of hydrogen chloride in dioxane was stirred at room temperature for 30 minutes under an atmosphere of nitrogen. At the end of this time, the reaction mixture was concentrated by evaporation under reduced pressure, and then benzene was added to the residue. The solvent was removed by distillation under reduced pressure from the resulting solution. The same operation was repeated, in total, three times, and the residue was then dried by evaporation under reduced pressure for 8 hours. The dried material was then suspended in 10 ml of anhydrous tetrahydrofuran, and 98.2 mg (0.354 mmole) of 2(R)-benzyl-3-(morpholinocarbonyl)propionic acid were added to the suspension. 0.06 ml (0.396 mmole) of 95% diethyl cyanophosphate and 0.2 ml (0.143 mmole) of triethylamine were then added to the resulting mixture, whilst ice-cooling and under an atmosphere of nitrogen. The mixture was then stirred for 8 hours, after which the solvent was removed by distillation under reduced pressure, and the residue was purified by silica gel column chromatography (using a 20:1 by volume mixture of methylene chloride and methanol as eluent), followed by recrystallization from a mixture of ethyl acetate and diisopropyl ether, to give 229.8 mg of the title compound as white crystals, melting at 92°–95° C.

Elemental Analysis: Calculated for $C_{40}H_{61}N_5O_7S \cdot 0.5H_2O$: C, 62.80%; H, 8.17%; N, 9.16%; B, 4.19%. Found: C, 62.51%; H, 8.21%; N, 8.79%: B, 3.85%.

PREPARATION 1

L-Cyclohexylalanine hydrochloride

A solution of 10.4 g (61.7 mmoles) of L-phenylalanine in 150 ml of 2N aqueous hydrochloric acid was subjected to a medium pressure catalytic hydrogenation reaction in the presence of 1 g of platinum black using a Paar's apparatus under about 4 atmospheres of hydrogen at room temperature for 24 hours. At the end of this time, the precipitated crystalline substance was dissolved by adding 250 ml of water, and the catalyst was removed by filtration. The filtrate was then concentrated to about 150 ml by evaporation under reduced pressure and allowed to stand overnight. The crystalline substance which deposited was collected by filtration and dried to give 12.8 g (yield 91%) of the title compound as white crystals, melting at 232°–234° C.

Elemental analysis: Calculated for $C_9H_{18}NO_2Cl$: C, 52.05%; H, 8.73%: N, 6.74%; Cl, 17.04%. Found: C, 51.97%; H, 8.75%; N, 6.69%; Cl, 17.21%.

PREPARATION 2

Methyl N-(t-butoxycarbonyl)-L-cyclohexylalanate 10.00 g (48.1 mmoles) of L-cyclohexylalanine hydrochloride (prepared as described in Preparation 1) were added to a mixture of 13.48 ml (96.6 mmoles) of triethylamine and 50 ml of a 1:1 by volume mixture of dioxane and water. 11.56 g (53.0 mmoles) of di-t-butyl dicarbonate were then added to the resulting mixture, whilst ice-cooling, and the mixture was stirred at room temperature overnight. At the end of this time, 50 ml of water were added to the reaction mixture, and the mixture was washed with 100 ml of ethyl acetate. The aqueous layer was separated and then adjusted to a pH value of 2.0 by adding a 10% w/v aqueous solution of citric acid, whilst ice-cooling. It was then extracted with ethyl acetate. The extract was washed with a saturated aqueous solution of sodium chloride and dried over anhydrous magnesium sulfate. The solvent was then removed by distillation under reduced pressure to give 10.02 g of N-(t-butoxycarbonyl)-L-cyclohexylalanine.

The whole of the N-(t-butoxycarbonyl)-L-cyclohexylalanine thus obtained was dissolved in 30 ml of anhydrous dimethylformamide, and 9.30 g (0.11 mole) of sodium bicarbonate and 2.53 ml (40.6 mmoles) of methyl iodide were then added to the resulting solution. The mixture was then stirred under an atmosphere of nitrogen at room temperature for 3 days. At the end of this time, the reaction mixture was filtered and the precipitate thus obtained was washed with methylene chloride. Water was added to the combined filtrate and washings, and the mixture was extracted with ethyl acetate. The organic extract was washed with a 5% w/v aqueous solution of sodium thiosulfate, a 5% w/v aqueous solution of sodium bicarbonate, a saturated aqueous solution of sodium chloride, a 10% w/v aqueous solution of citric acid, and water, in that order, and dried over anhydrous magnesium sulfate. The solvent was then removed by distillation under reduced pressure, to give 9.93 g (yield 72%) of the title compound as an oily substance.

Elemental analysis: Calculated for $C_{15}H_{27}NO_4$: C, 63.13%; H, 9.54%; N, 4.91%. Found: C. 62.66%; H, 9.29%: N, 4.74%.

Mass spectrum (m/e): 286 ($M^+ +1$), 170, 126.

PREPARATION 3

N-(t-Butoxycarbonyl)-L-cyclohexylalaninol 4.10 g (96.7 mmoles) of lithium chloride and 3.65 g (96.5 mmoles) of sodium borohydride were added to 150 ml of a 3:2 by volume mixture of ethanol and tetrahydrofuran, and the mixture was stirred for 30 minutes. At the end of this time, a solution of 9.64 g (33.8 mmoles) of methyl N-(t-butoxycarbonyl)-L-cyclohexylalanate (prepared as described in Preparation 2) in 100 ml of a 3:2 by volume mixture of ethanol and tetrahydrofuran was added dropwise to the mixture, whilst ice-cooling, and the mixture was stirred at room temperature overnight. The excess reagent was then decomposed by adding acetone, and then the solvent was removed by distillation under reduced pressure. Ethyl acetate was added to the residue, and the mixture was washed with water and dried over anhydrous magnesium sulfate. The solvent was then removed by distillation under reduced pressure to give 8.66 g (yield 99.7%) of the title compound as an oily substance.

Elemental analysis: Calculated for $C_{14}H_{27}NO_3$: C, 65.33%; H, 10.57%; N, 5.44%. Found: C. 65.31%: H, 10.40%; N, 5.42%.

Mass spectrum (m/e): 257 ($M^+$), 226, 170, 126.

PREPARATION 4

Ethyl (4RS, 5S)-6-cyclohexyl-5-(t-butoxycarbonylamino)-4-hydroxy-2-hexynate

4(a) 14.09 ml (0.10 mole) of triethylamine were added to a solution of 8.66 g (33.6 mmoles) of N-(t-butoxycarbonyl)-L-cyclohexylalaninol (prepared as described in Preparation 3) in 100 ml of anhydrous dimethyl sulfoxide, and then a solution of 16.07 g (0.10 mole) of sulfuric anhydride/pyridine complex in 100 ml of anhydrous dimethyl sulfoxide were added to the resulting mixture and under an atmosphere of nitrogen; the mixture was then stirred at room temperature for 10 minutes. At the end of this time, the reaction mixture was poured into 1000 ml of ice-water and extracted three times, each time with 500 ml of diethyl ether. The organic extract was washed with a 10% w/v aqueous solution of citric acid, with water and with a saturated aqueous solution of sodium chloride, in that order, and dried over anhydrous magnesium sulfate. The solvent was then removed by distillation under reduced pressure to give 8.58 g of N-(t-butoxycarbonyl)-L-cyclohexylalaninal.

4(b) 31.51 ml (50.4 mmoles) of a 1.6M solution of butyllithium in hexane were added, at −78° C. under an atmosphere of nitrogen, to a solution of 8.48 ml (60.5 mmoles) of diisopropylamine in 35 ml of anhydrous tetrahydrofuran, and the mixture was stirred for 30 minutes, after which 5.11 ml (50.4 mmoles) of ethyl propiolate were added. The mixture was stirred for an additional 30 minutes, and then a solution of N-(t-butoxycarbonyl)-L-cyclohexylalaninal [prepared as described in step 4(a) above] in 35 ml of anhydrous tetrahydrofuran was added to it. The resulting mixture was stirred for 3 hours, and then a saturated aqueous solution of ammonium chloride was added. The mixture was then extracted with ethyl acetate. The extract was washed with a 10% w/v aqueous solution of citric acid, with water and with a saturated aqueous solution of sodium chloride, in that order, and dried over anhydrous magnesium sulfate. The solvent was then removed by distillation under reduced pressure, and the residue was purified by silica gel column chromatography (using a 1:5 by volume mixture of ethyl acetate and hexane as eluent), to give 9.25 g of the title compound as a yellow oily substance.

PREPARATION 5

(5S)-5-[(1S)-1-(N-t-Butoxycarbonylamino)-2-cyclohexylethyl]dihydrofuran-2(3H)-one A solution of 9.25 g of the oily ethyl (4RS, 5S)-6-cyclohexyl-5-(t-butoxycarbonylamino)-4-hydroxy-2-hexynate (prepared as described in Preparation 4) in 100 ml of ethyl acetate was subjected to a catalytic hydrogenation reaction using a Paar's apparatus in the presence of 5 g of 5% w/w palladium-onbarium sulfate at about 4 atmospheres pressure for 4 hours. At the end of this time, the catalyst was removed by filtration, and the filtrate was condensed by evaporation under reduced pressure. The residue was then dissolved in 120 ml of toluene, 3 ml of acetic acid was added to the resulting solution, and the mixture was heated under reflux for 3 hours. The solvent was then removed by distillation under reduced pressure, and the residue was purified by medium pressure silica gel column chromatography (using a 2:1 by volume mixture of hexane and diethyl ether as eluent), to give 3.71 g [yield 35% from N-(t-butoxycarbonyl)-L-cyclohexylalaninol] of the title compound as the product of lesser polarity.

Elemental analysis: Calculated for $C_{17}H_{29}NO_4$: C, 65.57%; H, 9.39%; N, 4.50%. Found: C. 65.37%; H, 9.31%; N, 4.49%.

Mass spectrum (m/e): 311 (M+), 226, 170.

In addition, 640 mg [yield 6% from N-(t-butoxycarbonyl)-L-alaninol] of the (5R) diastereomer of the title compound were obtained as the product of greater polarity, in the form of crystals, melting at 97°-98° C.

Elemental analysis: Calculated for $C_{17}H_{29}NO_4$: C, 65.57%; H, 9.39%; N, 4.50%. Found: C, 65.51%; H, 9.40%; N, 4.61%.

Mass spectrum (m/e): 311 (M+), 226, 170.

PREPARATION 6

(3S, 5S)-5-[(1S)-1-(N-t-Butoxycarbonylamino)-2-cyclohexylethyl]-3-(1-hydroxy-1-methylethyl)dihydrofuran-2(3H)-one 15.81 ml (25.3 mmoles) of a 1.6M hexane solution of butyllithium were added, at −78° C. and under an atmosphere of nitrogen, to a solution of 3.55 ml (25.3 mmoles) of diisopropylamine in 30 ml of anhydrous tetrahydrofuran. The mixture was then stirred for 30 minutes, after which a solution of 3.58 g (11.5 mmoles) of (5S)-5-[(1S)-1-(N-t-butoxycarbonylamino)-2-cyclohexylethyl]dihydrofuran-2(3H)-one (prepared as described in Preparation 5) in 10 ml of anhydrous tetrahydrofuran was added to the mixture. It was then stirred at −78° C. for 1 hour, after which 1.86 ml (25.3 mmoles) of distilled acetone was added, and the mixture was stirred for a further 2 hours. At the end of this time, a saturated aqueous solution of ammonium chloride was added to the reaction mixture, and the mixture was extracted with ethyl acetate. The extract was washed with a 10% w/v aqueous solution of citric acid, with water, and with a saturated aqueous solution of sodium chloride, in that order, and dried over anhydrous magnesium sulfate. The solvent was then removed by distillation under reduced pressure, and the resulting residue was purified by medium pressure silica gel column chromatography (using a 1:1 by volume mixture of hexane and diethyl ether as eluent), to give 3.65 g (yield 86%) of the title compound as the product of lesser polarity, in the form of white crystals, melting at 123°-125° C.

Elemental analysis: Calculated for $C_{20}H_{35}NO_5$: C, 65.01%; H, 9.55%; N, 3.79%. Found: C, 65.01%; H, 9.62%; N, 3.91%.

Mass spectrum (m/e): 369 (M+), 226, 170, 126.

In addition, 290 mg (yield 7%) of the diastereomer (3R) of the title compound were obtained as the product of greater polarity, in the form of white crystals, melting at 141°-143° C.

Elemental analysis: Calculated for $C_{20}H_{35}NO_5$: C, 65.01%; H, 9.55%; N, 3.79%. Found: C, 64.99%; H, 9.66%; N, 3.91%.

Mass spectrum (m/e): 369 (M+), 226, 170, 126.

PREPARATION 7

(2S, 4S, 5S)-5-(t-Butoxycarbonylamino)-6-cyclohexyl-4-hydroxy-2-(1-hydroxy-1-methylethyl)-N-[2(S)-methylbutyl]-hexanamide A solution of 500 mg (1.35 mmoles) of (3S, 5S)-5-[(1S)-1-(N-t-butoxycarbonylamino)-2-cyclohexylethyl]-3-(1-hydroxy-1-methylethyl)dihydrofuran-2(3H)-one (prepared as described in Preparation 6) in 1.00 g (11.5 mmoles) of 2(S)-methylbutylamine was stirred at 100° C. for 4 hours. At the end of this time, the reaction mixture was concentrated by evaporation under reduced pressure, and the residue was purified by medium pressure silica gel column chromatography (using a 20:1 by volume mixture of methylene chloride and methanol as eluent), to give 570 mg (yield 92%) of the title compound as white crystals, melting at 64°-67° C.

Elemental analysis: Calculated for $C_{25}H_{48}N_2O_5 \cdot 0.5 \cdot H_2O$: C, 64.48%; H, 10.61%: N, 6.02%. Found: C, 64.98%; H, 10.74%; N, 6.13%.

Mass spectrum (m/e): 456 (M+), 212, 170, 126.

PREPARATION 8

(5S) -5-[(1S)-1-(N-t-Butoxycarbonylamino)-3-methylbutyl]-dihydrofuran-2(3H)-one

A procedure similar to that described in Preparations 4 and 5 was repeated, except that N-(t-butoxycarbonyl)-L-leucinol was used, to give 1.86 g of the title compound as white crystals, melting at 75°-77° C.

Elemental analysis: Calculated for $C_{14}H_{25}NO_4$: C, 61.97%: H, 9.29%: N, 5.16%. Found: C, 61.62%; H, 9.12%; N, 5.15%.

Mass spectrum (m/e): 271 (M+), 186, 130.

PREPARATION 9

(3S, 5S)-5-[(1S)-1-(N-t-Butoxycarbonylamino)-3-methylbutyl)-3-[(1-hydroxy-1-methylethyl)]dihydrofuran-2(3H)-one Following a procedure similar to that described in Preparation 6, 14.19 ml (22.7 mmoles) of a 1.6M hexane solution of butyllithium were added to a solution of 3.18 ml (22.7 mmoles) of diisopropylamine in 30 ml of anhydrous tetrahydrofuran at −78° C. under an atmosphere of nitrogen, and, after stirring the mixture for 30 minutes, a solution of 2.81 g (10.3 mmoles) of (5S)-5-[(1S)-1-(N-t-butoxycarbonylamino-3-methylbutyl]dihydrofuran-2(3M)-one (prepared as described in Preparation 8) in 10 ml of anhydrous tetrahydrofuran was added thereto, and the mixture was stirred at −78° C. for 1 hour. At the end of this time, 0.98 ml (13.3 mmoles) of distilled acetone was added to the mixture and stirring was continued for a further 2 hours. A saturated aqueous solution of ammonium chloride was then added to the reaction mixture, which was then extracted with ethyl acetate. The extract was washed with a 10% w/v aqueous solution of citric acid, with water and with a saturated aqueous solution of sodium chloride, in that order, and dried over anhydrous magnesium sulfate. The solvent was then removed by distillation under reduced pressure, and the resulting residue was purified by medium pressure silica gel column chromatography (using a 1:1 by volume mixture of hexane and diethyl ether as eluent), to give 2.47 g (yield 73%) of the title compound as the product of lesser polarity, in the form of a white amorphous substance.

Mass spectrum (m/e): 329 (M+), 186, 130, 86.

In addition, 170 mg (5%) of the diastereomer (2R) of the title compound was also obtained as the product of greater polarity, in the form of a white amorphous substance.

Mass spectrum (m/e): 329 (M+), 186, 130, 86.

PREPARATION 10

(2S, 4S, 5S)-5-(t-Butoxycarbonylamino)-4-hydroxy-2-(1-hydroxy-1-methylethyl)-7-methyl-N-[2(RS)-methylbutyl]octanamide Following a procedure similar to that described in Preparation 7, 250 mg (0.76 mmoles) of (3S, 5S)-5-[(1S)-1-(N-t-butoxycarbonylamino)-3-methylbutyl]-3-(1-hydroxy-1-methylethyl)dihydrofuran-2(3H)-one (prepared as described in Preparation 9) were dissolved in 500 mg (5.75 mmoles) of 2(RS)-methylbutylamine, and the solution was stirred at 100° C. for 3 hours. The reaction mixture was then concentrated by evaporation under reduced pressure, and the residue was purified by medium pressure silica gel column chromatography (using a 20:1 by volume mixture of methylene chloride and methanol as eluent). to give 270 mg (yield 85%) of the title compound as an amorphous substance.

Elemental analysis: Calculated for $C_{22}H_{44}N_2O_5$: C, 63.43%; H, 10.65%; N, 6.72%. Found: C, 62.80%; H, 10.52%; N, 6.65%.

Mass spectrum (m/e): 416 (M+), 212.

PREPARATION 11

4(S)-Isopropyl-3-[3-(4-methoxyphenyl)-1-oxobutyl]-2-oxazolidinone 18.19 ml (29.1 mmoles) of butyllithium (as a 1.6M hexane solution) were added dropwise at −78° C. and under an atmosphere of nitrogen to a solution of 3.13 g (24.2 mmoles) of 4(S)-isopropyl-2-oxazolidinone in 50 ml of anhydrous tetrahydrofuran, and then the mixture was stirred for 30 minutes. At the end of this time, a solution of 5.43 g (29.1 mmoles) of 3-(4-methoxyphenyl)propionyl chloride in 20 ml of anhydrous tetrahydrofuran was added dropwise to the resulting mixture over the course of 10 minutes. The mixture was then stirred for a further 1 hour, after which a saturated aqueous solution of ammonium chloride was added to the reaction mixture, which was then extracted with ethyl acetate. The extract was dried over anhydrous magnesium sulfate, and the solvent was removed by distillation under reduced pressure. The resulting residue was purified by medium pressure silica gel column chromatography (using a 1:3 by volume mixture of ethyl acetate and hexane as eluent), followed by recrystallization from diisopropyl ether, to give 5.63 g (yield 80%) of the title compound as white crystals, melting at 62.0°–63.5° C.

$[\alpha]_D^{20} = +60.4°$ (C=1, chloroform).

Elemental analysis: Calculated for $C_{16}H_{21}NO_4$: C, 65.96%; H, 7.27%; N, 4.81%. Found: C, 65.98%; H, 7.25%; N, 4.75%.

Mass spectrum (m/e): 291 (M+), 162, 134, 121.

Infrared Absorption Spectrum (KBr) $\nu_{max}$ cm$^{-1}$: 1777, 1698.

PREPARATION 12

3-[2(R)-(4-Methoxybenzyl)-3-(benzyloxycarbonyl)-propionyl]-4(S)-isopropyl-2-oxazolidione 14.31 ml (22.9 mmoles) of butyllithium (as a 1.6M hexane solution) were added dropwise at −78° C. and under an atmosphere of nitrogen to a solution of 3.21 ml (22.9 mmoles) of diisopropylamine in 100 ml of anhydrous tetrahydrofuran, and the mixture was stirred for 30 minutes. At the end of this time, a solution of 5.56 g (19.1 mmoles) of 4(S)-isopropyl-3-[3-(4-methoxyphenyl)-1-oxobutyl]-2-oxazolidinone (prepared as described in Preparation 11) in 20 ml of anhydrous tetrahydrofuran was added to the mixture. The mixture was then stirred for a further 1 hour, after which 9.08 ml (57.3 mmoles) of benzyl 2-bromoacetate were added, and the mixture was stirred for 12 hours, whilst allowing it gradually to return to room temperature. A saturated aqueous solution of ammonium chloride was then added to the reaction mixture, which was then extracted with ethyl acetate. The extract was dried over anhydrous magnesium sulfate, the solvent was removed by distillation under reduced pressure, and the residue was purified by medium pressure silica gel column chromatography (using a 1:3 by volume mixture of ethyl acetate and hexane as eluent), followed by recrystallization from diisopropyl ether, to give 6.03 g (yield 71%) of the title compound as white crystals, melting at 101°–103° C.

$[\alpha]_D^{20} = +82.4°$ (C=1, chloroform).

Elemental analysis: Calculated for $C_{25}H_{29}NO_6$: C. 68.32%: H, 6.65%; N, 3.19%. Found: C, 67.94%: H, 6.59%; N, 3.38%.

Mass spectrum (m/e): 439 (M+), 219, 191, 130, 121, 91.

Infrared Absorption Spectrum (KBr) $\nu_{max}$ cm$^{-}$: 1767, 1731, 1699.

PREPARATION 13

4-(S)-Isopropyl-3-[4-oxo-2(R)-(4-methoxybenzyl)-4-(morpholinobutyryl)]-2-oxazolidinone A solution of 5.75 g (13.1 mmoles) of 3-[2(R)-(4-methoxybenzyl)-3-(benzyloxycarbonyl)propionyl]-4(S)-isopropyl-2-oxazolidione (prepared as described in Preparation 12) in 200 ml of ethanol was stirred at room temperature for 4 hours in the presence of 500 mg of 10% w/w palladium-on-charcoal and under about 4 atmospheres of hydrogen. At the end of this time, the catalyst was removed by filtration, and the filtrate was concentrated by evaporation under reduced pressure. The residue was dissolved in 100 ml of anhydrous tetrahydrofuran, and 1.74 ml (14.4 mmoles) of morpholine, 2.19 ml of diethyl cyanophosphate and 2.01 ml of triethylamine were added to the resulting solution, whilst ice-cooling and under an atmosphere of nitrogen. The mixture was then stirred for 6 hours. At the end of this time, the solvent was removed by distillation under reduced pressure, and the residue was purified by medium pressure silica gel column chromatography (using a 1:1 by volume mixture of ethyl acetate and hexane as eluent), followed by recrystallization from diisopropyl ether, to give 5.11 g (yield 93%) of the title compound as white crystals, melting at 119°-121° C.

$[\alpha]_D^{20} + 91.1°$ (C=1, chloroform).

Elemental analysis: Calculated for $C_{22}H_{30}N_2O_6$: C, 63.14%; H, 7.23%; N, 6.69%. Found: C, 63.07%; H, 7.27%; N, 6.90%.

Mass spectrum (m/e): 418 (M+), 290, 161, 121.

Infrared Absorption Spectrum (KBr) $\nu_{max}$ cm$^{-1}$: 1762, 1697, 1645.

PREPARATION 14

Benzyl 2(R)-(4-methoxybenzyl)-3-(morpholinocarbonyl)-propionate 7.84 ml (12.5 mmoles) of butyllithium (as a 1.6M hexane solution) were added, whilst ice-cooling and under an atmosphere of nitrogen, to a solution of 1.73 ml (16.7 mmoles) of benzyl alcohol in 50 ml of anhydrous tetrahydrofuran. The mixture was stirred for 10 minutes, and then a solution of 3.50 g (8.36 mmoles) of 4(S)-isopropyl-3-[4-oxo-2(R)-(4-methoxybenzyl)-4-morpholinobutyryl]-2-oxazolidinone (prepared as described in Preparation 13) in 10 ml of anhydrous tetrahydrofuran was added dropwise thereto. The mixture was then stirred for 30 minutes, after which a saturated aqueous solution of ammonium chloride was added to the reaction mixture, which was then extracted with ethyl acetate. The extract was dried over anhydrous magnesium sulfate, the solvent was removed by distillation under reduced pressure, and the residue was purified by medium pressure silica gel column chromatography (using a 4:1 by volume mixture of benzene and ethyl acetate as eluent), followed by recrystallization from diisopropyl ether, to give 3.09 g (yield 93%) of the title compound as white crystals, melting at 77°-79° C.

$[\alpha]_D^{20} = +2.2°$ (C=1, chloroform).

Elemental analysis: Calculated for $C_{23}H_{27}NO_5$: C, 69.50%; H, 6.85%; N, 3.52%. Found: C, 69.29%; H, 6.90%; N, 3.66%.

Mass spectrum (m/e): 397 (M+), 130, 105.

Infrared Absorption Spectrum (KBr) $\nu_{max}$ cm$^{-1}$: 1737, 1625.

PREPARATION 15

2(R)-(4-Methoxybenzyl)-3-(morpholinocarbonyl)propionic acid

A solution of 1.62 g (4.08 mmoles) of benzyl 2(R)-(4-methoxybenzyl)-3-(morpholinocarbonyl)propionate (prepared as described in Preparation 14) in 50 ml of ethanol was stirred at room temperature for 4 hours in the presence of 160 mg of 10% w/w palladium-on-charcoal and under an atmosphere of hydrogen. At the end of this time, the catalyst was removed by filtration, and the filtrate was concentrated by evaporation under reduced pressure, to give the title compound as a colorless oily substance.

Mass spectrum (m/e): 307 (M+).

PREPARATION 16

4(R)-Isopropyl-3-(3-phenylpropionyl)-2-oxazolidinone 68.3 ml of butyllithium (as a 1.6M hexane solution) were added dropwise, at −78° C. and under an atmosphere of nitrogen, to a solution of 11.75 g (91.0 mmoles) of 4(S)-isopropyl-2-oxazolidinone in 200 ml of anhydrous tetrahydrofuran. The mixture was stirred for 30 minutes, and then a solution of 18.41 g (0.11 mmoles) of dihydrocinnamoyl chloride in 100 ml of anhydrous tetrahydrofuran was added dropwise over a period of 10 minutes. The mixture was then stirred for a further 1 hour, after which 100 ml of 1N aqueous hydrochloric acid and 100 ml of a saturated aqueous solution of sodium chloride were added to the reaction mixture, which was then extracted with ethyl acetate. The extract was dried over anhydrous magnesium sulfate, the solvent was removed by distillation under reduced pressure, and the residue was purified by medium pressure silica gel column chromatography (using a 1:4 by volume mixture of ethyl acetate and hexane as eluent), followed by recrystallization from diisopropyl ether, to give 20.12 g (yield 85%) of the title compound as white crystals, melting at 62°-63° C.

$[\alpha]_D^{20} = +71.4°$ (C=1, chloroform).

Elemental analysis: Calculated for $C_{15}H_{19}NO_3$: C, 68.94%; H, 7.33%; N, 5.36%. Found: C, 68.89%; H, 7.12%; N, 5.43%.

Mass spectrum (m/e): 261 (M+), 130, 104, 91.

Infrared Absorption Spectrum (Nujol—trade mark) $\nu_{max}$ cm$^{-1}$: 1785, 1700.

PREPARATION 17

3-[2(S)-Benzyl-4-pentenoyl]-4(S)-isopropyl-2-oxazolidinone 8.61 ml (13.8 mmoles) of butyllithium (as a 1.6M hexane solution) were added dropwise, at −78° C. and under an atmosphere of nitrogen, to a solution of 1.93 ml (13.8 mmoles) of diisopropylamine in 20 ml of anhydrous tetrahydrofuran. The mixture was stirred for 30 minutes, and then a solution of 3.00 mg (11.5 mmoles) of 4(S)-isopropyl-3-(3-phenylpropionyl)-2-oxazolidinone (prepared as described in Preparation 16) in 10 ml of anhydrous tetrahydrofuran was added dropwise thereto, and the mixture was stirred for 1 hour. At the end of this time, 2.99 ml (34.6 mmoles) of allyl bromide were added to the mixture, and the mixture was stirred for 12 hours, whilst allowing it to return gradually to room temperature. A saturated aqueous solution of ammonium chloride was added to the reaction mixture, which was then extracted with ethyl acetate. The extract was dried over anhydrous magnesium sulfate, the solvent was removed by distillation under reduced pressure, and the residue was purified by medium pressure silica gel column chromatography (using a 5:1 by volume mixture of hexane and ethyl acetate as eluent), to give 2.14 g (yield 62%) of the title compound as a colorless oily substance.

$[\alpha]_D^{20} = +125.0°$ (C=1.53, chloroform).

Elemental analysis: Calculated for $C_{18}H_{23}NO_3$: C, 71.73%; H, 7.69%; N, 4.65%. Found: C, 72.21%; H, 7.65%; N, 4.68%.

Mass spectrum (m/e): 301 (M+), 260, 210, 131, 91.

Infrared Absorption Spectrum (CHCl3) $\nu_{max}$ cm$^{-1}$: 1695, 1775.

PREPARATION 18

Benzyl 2(S)-benzyl-4-pentenoate 5.63 ml (9.01 mmoles) of butyllithium (as a 1.6M hexane solution) were added, whilst ice-cooling and under an atmosphere of nitrogen, to a solution of 1.24 ml (12.0 mmoles) of benzyl alcohol in 20 ml of anhydrous tetrahydrofuran. The mixture was stirred for 10 minutes, and then a solution of 1.81 g (6.01 mmoles) of 3-[2(R)-benzyl-4-pentenoyl]-4(S)-isopropyl-2-oxazolidinone (prepared by a procedure similar to that described in Preparation 17) in 10 ml of anhydrous tetrahydrofuran was added dropwise thereto. The mixture was then stirred for 30 minutes, after which a saturated aqueous solution of ammonium chloride was added to the reaction mixture, which was then extracted with ethyl acetate. The extract was dried over anhydrous magnesium sulfate, the solvent was removed by distillation under reduced pressure, and the residue was purified by medium pressure silica gel column chromatography (using a 10:1 by volume mixture of hexane and ethyl acetate as eluent), to give 1.58 g (yield 94%) of the title compound as a colorless oily substance.

$[\alpha]_D^{20} = +22.5°$ (C=1.09, chloroform).

Elemental analysis: Calculated for $C_{19}H_{20}O_2$: C, 81.40%; H, 7.19%. Found: C, 81.40%; H, 7.32%.

Mass spectrum (m/e): 281 (M++1), 180, 143, 91.

Infrared Absorption Spectrum (CHCl3) $\nu_{max}$ cm$^{-1}$: 1725.

PREPARATION 19

Benzyl 2(R)-benzyl-4-oxopentanoate

A suspension of 500 mg (5 mmoles) of cuprous chloride and 180 mg (1 mmole) of palladium chloride in a mixture of 5 ml of dimethylformamide and 0.6 ml of water was stirred for 1 hour under an atmosphere of oxygen. At the end of this time, 1.41 g(5.03 mmoles) of benzyl 2(S)-benzyl-4-pentenoate (prepared as described in Preparation 18) was added to the mixture. The mixture was then stirred for an additional 5 hours at room temperature and under an atmosphere of oxygen, after which the reaction mixture was poured into 100 ml of 1N aqueous hydrochloric acid, and the mixture was extracted with methylene chloride. The extract was dried over anhydrous magnesium sulfate, the solvent was removed by distillation under reduced pressure, and the residue was purified by medium pressure silica gel column chromatography (using a 5:1 by volume mixture of hexane and ethyl acetate as eluent), to give 1.28 g (yield 86%) of the title compound as a colorless oily substance.

$[\alpha]_D^{20} = +13.5°$ (C=1.93, chloroform).

Elemental analysis: Calculated for $C_{19}H_2O_3$: C, 77.00%: H, 6.80%. Found: C, 76.56%; H, 6.87%.

Mass spectrum (m/e): 296 (M+), 205, 187, 91.

Infrared Absorption Spectrum (CHCl3) $\nu_{max}$ cm$^{-1}$: 1720.

PREPARATION 20

2(R)-Benzyl-4-oxopentanoic acid

A solution or 1.00 g (3.37 mmoles) of benzyl 2(R)-benzyl-4-oxopentanoate (prepared as described in Preparation 19) in 10 ml of ethanol was stirred at room temperature for 3 hours in the presence of 100 mg of 10% w/w palladium-on-charcoal and under about 4 atmospheres of hydrogen. At the end of this time, the catalyst was removed by filtration, and then the solvent was removed by distillation under reduced pressure. The residue was recrystallized from a mixture of hexane and diisopropyl ether, to give 610 mg (yield 88%) of the title compound as white crystals, melting at 71°-73° C.

$[\alpha]_D^{20} = +17.0°$ (C=1.04, chloroform).

Elemental analysis: Calculated for $C_{12}H_{14}O_3$: C, 69.89%; H, 6.84%. Found: C, 69.56%: H, 6.69%.

Mass spectrum (m/e): 207 (M++1), 149, 131, 91.

Infrared Absorption Spectrum (KBr) $\nu_{max}$ cm$^{-1}$: 1741, 1691.

PREPARATION 21

(3S, 5S)-5-[(1S)-1-(N-t-Butoxycarbonylamino)-2-cyclohexylethyl]-3-[1-ethyl-1-hydroxypropyl]dihydrofuran-2(3H)-one 1.43 ml (3.58 mmoles) of butyllithium (as a 2.5M hexane solution) was added dropwise, at −78° C. and under an atmosphere of nitrogen, to a solution of 0.50 ml (3.57 mmoles) of diisopropylamine in 10 ml of anhydrous tetrahydrofuran. The mixture was then stirred for 30 minutes, after which a solution of 500 mg (1.61 mmoles) of (5S)-5-[(1S)-1-(N-t-butoxycarbonylamino)-2-cyclohexylethyl]dihydrofuran-2(3H)-one (prepared as described in Preparation 5) in 5 ml of anhydrous tetrahydrofuran was added thereto. The mixture was then stirred for a further 1 hour, and then 0.38 ml (3.59 mmoles) of distilled 3-pentanone was added to the mixture and stirred for a further 2 hours. At the end of this time, a saturated aqueous solution of ammonium chloride was added to the reaction mixture, which was then extracted with ethyl acetate. The extract was washed with a 10% w/v aqueous solution of citric acid, with water and with a saturated aqueous solution of sodium chloride, in that order. It was then dried over anhydrous magnesium sulfate, and the solvent was removed by distillation under reduced pressure. The residue was purified by medium pressure silica gel column chromatography (using a 1:1 by volume mixture of hexane and diethyl ethyl as eluent), followed by recrystallization from hexane, to give 425 mg (yield 67%) of the title compound as white crystals, melting at 118°-120° C.

$[\alpha]_D^{20} = -19.2°$ (C=1, methanol).

Elemental analysis: Calculated for $C_{22}H_{39}NO_5$: C, 66.47%; H, 9.89%; N, 3.52%. Found: C, 66.69%; H, 9.97%; N, 3.66%.

PREPARATION 22

(3S, 5S)-5-[(1S)-1-(N-t-Butoxycarbonylamino)-2-cyclohexylethyl]-3-(1-hydroxycyclohexyl)dihydrofuran-2(3H)-one 1.43 ml (3.58 mmoles) of butyllithium (as a 2.5M hexane solution) was added dropwise, at −78° C. and under an atmosphere of nitrogen, to a solution of 0.50 ml (3.57 mmoles) of diisopropylamine in 10 ml of anhydrous tetrahydrofuran. The mixture was then stirred for 30 minutes, after which a solution of 500 mg (1.61 mmoles) of (5S)-5-[(1S)-1-(N-t-butoxycarbonylamino)-2-cyclohexylethyl]dihydrofuran-2(3H)-one (prepared as described in Preparation 5) in 5 ml of anhydrous tetrahydrofuran was added thereto. The mixture was then stirred for a further 1 hour, and then 0.24 ml (3.55 mmoles) of distilled cyclohexanone was added to the mixture and stirred for 2 hours. A saturated aqueous solution of ammonium chloride was added to the reaction mixture, which was then extracted with ethyl acetate. The extract was washed with a 10% w/v aqueous solution of citric acid, with water and with a saturated aqueous solution of sodium chloride, in that order. It was then dried over anhydrous magnesium sulfate, and the solvent was removed by distillation under reduced pressure. The residue was purified by medium pressure silica gel column chromatography (using a 1:1 by volume mixture of hexane and diethyl ether as eluent), followed by recrystallization from hexane, to give 410 mg (yield 62%) of the title compound as white crystals, melting at 133°–134° C.

$[\alpha]_D^{20} = -17.4°$ (C=1, methanol).

Elemental analysis: Calculated for $C_{23}H_{39}NO_5$: C, 67.45%; H, Found: C, 67.49%; H, 9.60%; N, 3.48%.

PREPARATION 23

(2S, 4S, 5S)-5-(t-Butoxycarbonylamino)-6-cyclohexyl-4-hydroxy-2-(1-hydroxy-1-methylethyl)-N-methylhexanamide A solution of 1.93 g (5.22 mmoles) of (3S, 5S)-5-[(1S)-1-(N-t-butoxycarbonylamino)-2-cyclohexylethyl]-3-(1-hydroxy-1-methylethyl)dihydrofuran-2(3H)-one (prepared as described in Preparation 6) in 50 ml of methanol was saturated with gaseous methylamine by passing the gas through the solution whilst ice-cooling, and then the flask containing the reaction mixture was stoppered tightly and allowed to stand at room temperature overnight. The reaction mixture was then concentrated by evaporation under reduced pressure, and the residue was purified by medium pressure silica gel column chromatography (using a 20:1 by volume mixture of methylene chloride and methanol as eluent), followed by recrystallization from hexane, to give 1.98 g (yield 95%) of the title compound as white crystals, melting at 174°–175° C.

$[\alpha]_D^{20} = -35.0°$ (C=1, methanol).

Elemental analysis: Calculated for $C_{21}H_{40}N_2O_5$: C, 62.97%; H, 10.07%; N, 6.99%. Found: C, 62.85%; H, 10.16%; N, 7.08%.

Mass spectrum (m/e): 401 (M++1), 174, 156, 126, 57.

PREPARATION 24

(2S, 4S, 5S)-5-(t-Butoxycarbonylamino)-6-cyclohexyl-4-hydroxy-2-(1-hydroxy-1-methylethyl)-N-ethylhexanamide A solution of 400 mg (1.08 mmoles) of (5S)-5-[(1S)-1-(N-t-butoxycarbonylamino)-2-cyclohexylethyl]dihydrofuran-2(3H)-one (prepared as described in Preparation 5) in 20 ml of methanol was saturated with ethylamine. After it had been allowed to stand at room temperature overnight, the reaction mixture was concentrated by evaporation under reduced pressure, and the residue obtained, as an oily substance was dissolved in warm diethyl ether. The solution was then allowed to stand, and the needle-like crystals which deposited were collected by filtration, to give 317 mg of the title compound, melting at 155°–157° C.

PREPARATION 25

(2S, 4S, 5S)-5-(t-Butoxycarbonylamino)-6-cyclohexyl-4-hydroxy-2-(1-hydroxy-1-methylethyl)-N-dimethylhexanamide A solution of 628 mg (1.7 mmoles) of (5S)-5-[(1S)-1-(N-t-butoxycarbonylamino)-2-cyclohexylethyl]dihydrofuran-2(3H)-one (prepared as described in Preparation 5) in 5 ml of methanol was saturated with dimethylamine. After it had been allowed to stand at room temperature for 22.5 hours, the solution was heated under reflux for 7.5 hours using a dry ice-acetone condenser, and the solvent was removed by distillation under reduced pressure. The pale yellow oily residue was purified by silica gel column chromatography (using a 10:1 by volume mixture of methylene chloride and methanol as eluent), followed by recrystallization from diisopropyl ether, to give 182 mg of the title compound, melting at 136°–137° C.

PREPARATION 26

(2S, 4S, 5S)-5-(t-Butoxycarbonylamino)-6-cyclohexyl-4-hydroxy-2-(1-ethyl-1-hydroxypropyl)-N-methylhexanamide A solution of 361 mg (0.91 mmoles) of (3S, 5S)-5-[(1S)-1-(N-t-butoxycarbonylamino)-2-cyclohexylethyl]-3-(1-ethyl-1-hydroxypropyl)dihydrofuran-2(3H)-one (prepared as described in Preparation 21) in 10 ml of methanol was saturated with gaseous methylamine by passing the gas through the solution whilst ice-cooling, and then the flask containing the reaction mixture was stoppered tightly and allowed to stand at room temperature overnight. The reaction mixture was then concentrated by evaporation under reduced pressure, and the residue was purified by medium pressure silica gel column chromatography (using a 20:1 by volume mixture of methylene chloride and methanol as eluent), followed by recrystallization from hexane, to give 372 mg (yield 96%) of the title compound as white crystals, melting at 152°–155° C.

$[\alpha]_D^{20} = -30.8°$ (C=0.8, methanol).

Elemental analysis: Calculated for $C_{23}H_{44}N_2O_5$: C, 64.45%; H, 10.35%; N, 6.54%. Found: C, 63.85%; H, 10.45%; N, 6.45%.

Mass spectrum (m/e): 429 (M++1), 184, 126.

PREPARATION 27

(2S, 4S, 5S)-5-(t-Butoxycarbonylamino)-6-cyclohexyl-4-hydroxy-2-(1-hydroxycyclohexyl)-N-methylhexanamide A solution of 274 mg (0.67 mmoles) of (3S, 5S)-5-[(1S)-1-(N-t-butoxycarbonylamino)-2-cyclohexylethyl]-3-(1-hydroxycyclohexyl)dihydrofuran-2(3H)-one (prepared as described in Preparation 22) in 10 ml of methanol was saturated with gaseous methylamine by passing the gas through the solution whilst ice-cooling, and then the flask containing the reaction mixture was stoppered tightly, and allowed to stand at room temperature overnight. The reaction mixture was then concentrated by evaporation under reduced pressure, and the residue was purified by medium pressure silica gel column chromatography (using a 20:1 by volume mixture of methylene chloride and methanol as eluent), followed by recrystallization from hexane, to give 286 mg (yield 97%) of the title compound as white crystals, melting at 175°-177° C.

$[\alpha]_D^{20} = -29.2°$ (C=0.9, methanol).

Elemental analysis: Calculated for $C_{24}H_{44}N_2O_5$: C, 65.42%: H, 10.07%: N, 6.36%. Found: C, 64.95%; H, 10.10%: N, 6.49%.

Mass spectrum (m/e): 441 (M++1), 196, 126.

PREPARATION 28

(2S, 4S, 5S)-5-(t-Butoxycarbonylamino)-4-hydroxy-2-(1-hydroxy-1-methylethyl)-7-methyl-N-methyloctanamide A solution of 285 mg (0.86 mmoles) of (3S, 5S)-5-[(1S)-1-(M-t-butoxycarbonylamino)-3-methylbutyl]-3-(1-hydroxy-1-methylethyl)dihydrofuran-2(3H)-one in 5 ml of methanol was saturated with gaseous methylamine by passing the gas through the solution whilst ice-cooling, and then the flask containing the reaction mixture was stoppered tightly, and allowed to stand at room temperature overnight. The reaction mixture was then concentrated by evaporation under reduced pressure, and the residue was purified by medium pressure silica gel column chromatography (using a 20:1 by volume mixture of methylene chloride and methanol as eluent), followed by recrystallization from hexane, to give 286 mg (yield 92%) of the title compound as white crystals, melting at 121°-123° C.

$[\alpha]_D^{20} = -38.1°$ (C=0.7, methanol).

PREPARATION 29

(2S, 4S, 5S)-5-(t-Butoxycarbonylamino)-6-cyclohexyl-4-hydroxy-2-(1-hydroxy-1-methylethyl)-N-butylhexanamide A solution of 500 mg (1.35 mmole) of (3S, 5S)-5-[1(S)-(N-t-butoxycarbonylamino)-2-cyclohexylethyl]-3-(1-hydroxy-1-methylethyl)dihydrofuran-2(3H)-one (prepared as described in Preparation 6) in 841.1 mg (11.5 mmole) of butylamine was stirred at 100° C. for 4 hours. At the end of this time, the reaction mixture was concentrated by evaporation under reduced pressure, and the residue was purified by medium pressure silica gel column chromatography (using a 20:1 by volume mixture of methylene chloride and methanol as eluent), to give 341 mg (yield 57.2%) of the title compound as white crystals, melting at 91°-93° C.

We claim:

1. A compound of formula (I):

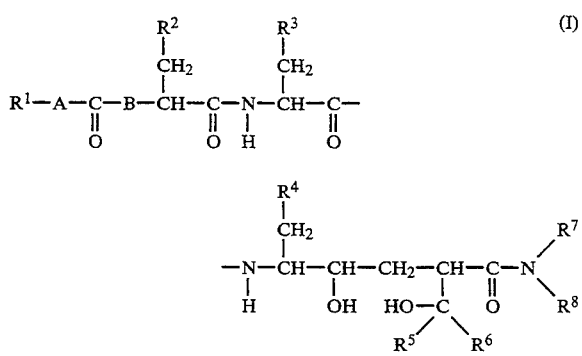

in which

A represents a single carbon-carbon bond and B represents a methylene group or A represents a methylene group and B represents an imino group;

$R^1$ represents a $C_{1-4}$ alkyl group, an unsubstituted morpholinyl group; substituted morpholinyl group having methyl substituents; a thiomorpholinyl group; a 2-oxopyrrolidinyl group; a piperazinyl group; or a substituted piperazinyl group substituted by methyl, unsubstituted phenyl or phenyl substituted with methyl, methoxy or halogen atoms, or a group of formula (II):

in which $R^9$ and $R^{10}$ are independently selected from the group consisting of $C_1$-$C_4$ alkyl groups, $C_7$-$C_{10}$ aralkyl and $C_3$-$C_7$ cycloalkyl groups;

$R^2$ represents a naphthyl group, an unsubstituted phenyl group or a substituted phenyl group having at least one substituent selected from the group consisting of a $C_1$-$C_4$ alkyl group, a halogen atom, a hydroxy group, a trifluoromethyl group and a $C_1$-$C_4$ alkoxy group;

$R^3$ represents a thiazolyl group;

$R^4$ represents an isopropyl group or a cyclohexyl group;

$R^5$ and $R^6$ are independently selected from the group consisting of $C_1$-$C_4$ alkyl groups, or, together with the carbon atom to which they are attached, form a $C_5$ or $C_6$ cycloalkyl group;

$R^7$ represents a $C_1$-$C_6$ alkyl group; and $R^8$ represents a hydrogen atom.

2. The compound of claim 1, wherein the carbon atom indicated by an asterisk in the moiety of formula:

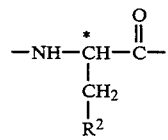

is in the S configuration.

3. The compound of claim 1, wherein the carbon atom indicated by an asterisk in the moiety of formula:

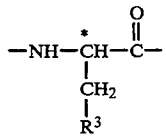

is in the S configuration.

4. The compound of claim 1, wherein the carbon atom indicated by an asterisk in the moiety of formula:

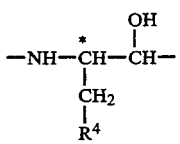

is in the S configuration.

5. The compound of claim 1, wherein the carbon atom indicated by an asterisk in the moiety of formula:

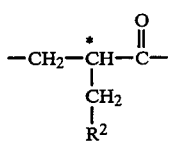

is in the R configuration.

6. The compound of claim 1, wherein the carbon atom indicated by an asterisk in the moiety of formula:

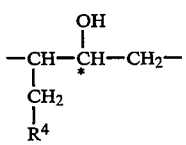

is in the S configuration.

7. The compound of claim 1, wherein the carbon atom indicated by an asterisk in the moiety of formula:

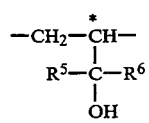

is in the S configuration.

8. The compound of claim 1, wherein the carbon atom indicated by an asterisk in the moiety of formula:

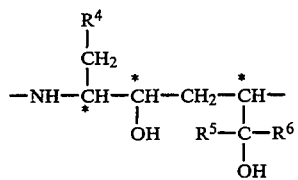

are all in the S configuration.

9. The compound of claim 1, wherein A represents a single bond, and B represents a methylene group.

10. The compound of claim 1, wherein A represents a methylene group, and B represents an imino group.

11. The compound of claim 1, wherein $R^2$ represents a phenyl group, a 4-methoxyphenyl group or a naphthyl group.

12. The compound of claim 1, wherein $R^5$ and $R^6$ each represents a $C_1$-$C_4$ alkyl group, or, together with the carbon atom to which they are attached, represent a cyclopentyl group or a cyclohexyl group.

13. The compound of claim 1, selected from the group consisting of 5-{N-[N-morpholinoacetyl-3-(1-naphthyl)alanyl]-3-(4-thiazolyl)alanyl}amino-6-cyclohexyl-4-hydroxy-2-(1-hydroxy-1-methylethyl)-N-methylbutyl)hexanamide and pharmaceutically acceptable salts thereof.

14. The compound of claim 1, selected from the group consisting of (2S, 4S, 5S)-5-{N-[N-morpholinoacetyl-3-(1-naphthyl)-L-alanyl]-3-(4-thiazolyl)-L-alanyl-}amino-6-cyclohexyl-4-hydroxy-2-(1-hydroxy-1-methylethyl)-N-[2(S)-methylbutyl]hexanamide and pharmaceutically acceptable salts thereof.

15. The compound of claim 1, selected from the group consisting of 5-{N-[2-(1-naphthylmethyl)-3-(morpholinocarbonyl)propionyl]-3-(4-thiazolyl)alanyl-}amino-6-cyclohexyl-4-hydroxy-2-(1-hydroxy-1-methylethyl)-N-methylhexanamide and pharmaceutically acceptable salts thereof.

16. The compound of claim 1, selected from the group consisting of (2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-methylhexanamide and pharmaceutically acceptable salts thereof.

17. The compound of claim 1, selected from the group consisting of 5-{N-[2-(1-naphthylmethyl)-3-(morpholinocarbonyl)propionyl]-3-(4-thiazolyl)alanyl-}amino-6-cyclohexyl-4-hydroxy-2-(1-hydroxy-1-methylethyl)-N-(2-methylbutyl)hexanamide and pharmaceutically acceptable salts thereof.

18. The compound of claim 1, selected from the group consisting of (2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide and pharmaceutically acceptable salts thereof.

19. The compound of claim 1, selected from the group consisting of 5-{N-[2-(1-naphthylmethyl)-3-(morpholinocarbonyl)propionyl]-3-(4-thiazolyl)alanyl-}amino-6-cyclohexyl-4-hydroxy-2-(1-hydroxy-1-ethylpropyl)-N-methylhexanamide and pharmaceutically acceptable salts thereof.

20. The compound of claim 1, selected from the group consisting of (2S, 4S, 5S)-5-{N-[2(R)-(1-naphthylmethyl)- 3-(morpholinocarbonyl)propionyl]-3-(4-thiazolyl)-L-alanyl}amino-6-cyclohexyl-4-hydroxy-2-

(1-hydroxy-1-ethylpropyl)-N-methylhexanamide and pharmaceutically acceptable salts thereof.

21. The compound of claim 1, selected from the group consisting of 5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-butylhexanamide and pharmaceutically acceptable salts thereof.

22. The compound of claim 1, selected from the group consisting of (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-butylhexanamide and pharmaceutically acceptable salts thereof.

23. The compound of claim 1, selected from the group consisting of 5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-(2-methylbutyl)hexanamide and pharmaceutically acceptable salts thereof.

24. The compound of claim 1, selected from the group consisting of (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide and pharmaceutically acceptable salts thereof.

25. The compound of claim 1, selected from the group consisting of 5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-methylhexanamide and pharmaceutically acceptable salts thereof.

26. The compound of claim 1, selected from the group consisting of (2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide and pharmaceutically acceptable salts thereof.

27. The compound of claim 1, selected from the group consisting of 5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-ethylhexanamide and pharmaceutically acceptable salts thereof.

28. The compound of claim 1, selected from the group consisting of (2S, 4S, 5S)-5-{N-[2(R)-benzyl-3-morpholinocarbonyl)propionyl]-3-(4-thiazolyl)-N-alanyl}amino-6-cyclohexyl-4-hydroxy-2-(1-hydroxy-1-methylethyl)-N-ethylhexanamide and pharmaceutically acceptable salts thereof.

29. The compound of claim 1, selected from the group consisting of 5-{N-[2-benzyl-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide and pharmaceutically acceptable salts thereof.

30. The compound of claim 1, selected from the group consisting of (2S, 4S, 5S)-5-{N-[2(R)-benzyl-3-morpholinocarbonyl)propionyl]-3-(4-thiazolyl)-N-alanyl}amino-6-cyclohexyl-4-hydroxy-2-(1-hydroxy-1-ethylpropyl)-N-methylhexanamide and pharmaceutically acceptable salts thereof.

31. The compound of claim 1, selected from the group consisting of 5-{N-[2-benzyl-3-(N-benzyl-N-methylcarbamoyl)propionyl]-3-(4-thiazolyl)alanyl}amino-6-cyclohexyl-4-hydroxy-2-(1-hydroxy-1-methylethyl)-N-methylhexanamide and pharmaceutically acceptable salts thereof.

32. The compound of claim 1, selected from the group consisting of (2S, 4S, 5S)-5-{N-[2(R)-benzyl-3-(N-benzyl-N-methylcarbamoyl)propionyl]-3-(4-thiazolyl)-N-alanyl}amino-6-cyclohexyl-4-hydroxy-2-(1-hydroxy-1-methylethyl)-N-methylhexanamide and pharmaceutically acceptable salts thereof.

33. The compound of claim 1, selected from the group consisting of 5-{N-[2-benzyl-3-(N-cyclohexyl-N-methylcarbamoyl)propionyl]-3-(4-thiazolyl)alanyl}amino-6-cyclohexyl-4-hydroxy-2-(1-hydroxy-1-methylethyl)-N-methylhexanamide and pharmaceutically acceptable salts thereof.

34. The compound of claim 1, selected from the group consisting of (2S, 4S, 5S)-5-{N-[2(R)-benzyl-3-(N-cyclohexyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide and pharmaceutically acceptable salts thereof.

35. The compound of claim 1, selected from the group consisting of 5-{N-[2-(p-methoxybenzyl)-3-(morpholinocarbonyl)propionyl]-3-(4-thiazolyl)alanyl}amino-6-cyclohexyl-4-hydroxy-2-(1-hydroxy-1-methylethyl)-N-methylhexanamide and pharmaceutically acceptable salts thereof.

36. The compound of claim 1, selected from the group consisting of (2S, 4S, 5S)-5-{N-[2(R)-(p-methoxybenzyl)-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide and pharmaceutically acceptable salts thereof.

37. The compound of claim 1, selected from the group consisting of 5-{N-[2-(1-naphthylmethyl)-3-(morpholinocarbonyl)propionyl]-3-(4-thiazolyl)alanyl}amino-6-cyclohexyl-4-hydroxy-2-(1-hydroxycyclohexyl)-N-methylhexanamide and pharmaceutically acceptable salts thereof.

38. The compound of claim 1, selected from the group consisting of (2S, 4S, 5S)-5-{N-[2(R)-(1-naphthylmethyl)-3-morpholinocarbonyl)propionyl]-3-(4-thiazolyl)-L-alanyl}amino-6-cyclohexyl-4-hydroxy-2-(1-hydroxycyclohexyl)-N-methylhexanamide and pharmaceutically acceptable salts thereof.

39. A method for the treatment or prophylaxis of angiotensin-induced hypertension in an animal by the administration thereto of fan effective amount of antihypertensive agent, wherein said antihypertensive agent is selected from the group consisting of compounds of claim 1, and pharmaceutically acceptable salts thereof.

40. The method of claim 39, wherein A represents a single bond, and B represents a methylene group.

41. The method of claim 39, wherein A represents a methylene group, and B represents an imino group.

42. The method of claim 39, wherein $R^2$ represents a phenyl group, a 4-methoxyphenyl group or a naphthyl group.

43. The method of claim 39, wherein $R^5$ and $R^6$ each represents a $C_1$-$C_4$ alkyl group, or, together with the carbon atom to which they are attached, represent a cyclopentyl group or a cyclohexyl group.

44. The method of claim 39, wherein said antihypertensive agent is selected from the group consisting of;

5-{N-[N-morpholinoacetyl-3-(1-naphthyl)alanyl]-3-(4-thiazolyl)alanyl}amino-6-cyclohexyl-4-hydroxy-2-(1-hydroxy-1-methylethyl)-N-(2-methylbutyl)hexanamide;

5-{N-[2-(1-naphthylmethyl)-3-(morpholinocarbonyl)propionyl]-3-(4-thiazolyl)alanyl}amino-6- cyclohexyl-4-hydroxy-2-(1-hydroxy-1-methylethyl)-N-methylhexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxy-1-methylethyl)-N-(2-methylbutyl)hexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-butylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-(2-methylbutyl)hexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-methylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-ethylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide;

5-{N-[2-benzyl-3-(N-benzyl-N-methylcarbamoyl)propionyl]-3-f4-thiazolyl)alanyl}amino-6-cyclohexyl-4-hydroxy-2-(1-hydroxy-1-methylethyl)-N-methylhexanamide;

5-{N-[2-benzyl-3-(N-cyclohexyl-N-methylcarbamoyl)propionyl]-3-(4-thiazolyl)alanyl}amino-6-cyclohexyl-4-hydroxy-2-(1-hydroxy-1-methylethyl)-N-methylhexanamide;

5-{N-[2-(p-methoxybenzyl)-3-(morpholinocarbonyl)propionyl]-3-(4-thiazolyl)alanyl}amino-6-cyclohexyl-4-hydroxy-2-(1-hydroxy-1-methylethyl)-N-methylhexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxycyclohexyl)-N-methylhexanamide;

and pharmaceutically acceptable salts thereof.

45. The method of claim 39, wherein said antihypertensive agent is selected from the group consisting of:

(2S, 4S, 5S)-5-{N-[N-morpholinoacetyl-3-(1-naphthyl)-L-alanyl]-3-(4-thiazolyl)-L-alanyl}amino-6-cyclohexyl-4-hydroxy-2-(1-hydroxy-1-methylethyl)-N-[2(S)-methylbutyl]hexanamide;

(2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide;

(2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-ethylpropyl)-N-methylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-butylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-ethylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-ethylpropyl)-N-methylhexanamide;

(2S, 4S, 5S)-5-{N-[2(R)-benzyl-3-(N-benzyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-benzyl-3-(N-cyclohexyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-(p-methoxybenzyl)-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-(1-naphthylmethyl)-3-(morpholino carbonyl)propionyl]-3-(4-thiazolyl)-L-alanyl}amino-6-cyclohexyl-4-hydroxy-2-(1-hydroxycyclohexyl)-N-methylhexanamide;

and pharmaceutically acceptable salts thereof.

46. A composition for the treatment of angiotensin-induced hypertension in an animal which comprises an antihypertensive agent in admixture with a pharmaceutically acceptable carrier or diluent, wherein said antihypertensive agent is selected from the group consisting of compounds of formula (I), as defined in claim 1, and pharmaceutically acceptable salts thereof.

47. The composition of claim 46, wherein said antihypertensive agent is selected from the group consisting of:

5-{N-[N-morpholinoacetyl-3-(1-naphthyl)alanyl]-3-(4-thiazolyl)alanyl}amino-6-cyclohexyl-4-hydroxy-2-(1-hydroxy-1-methylethyl)-N-(2-methylbutyl)hexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxy-1-methylethyl)-N-methylhexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxy-1-methylethyl)-N-(2-methylbutyl)hexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-butylhexanamide;

5-{N-[2-benzyl-3-(morpholinocarbonyl)propionyl]-3-(4-thiazolyl)alanyl}amino-6-cyclohexyl-4- hydroxy-2-(1-hydroxy-1-methylethyl)-N-(2-methylbutyl)hexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-methylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-methylethyl)-N-ethylhexanamide;

5-{N-[2-benzyl-3-(morpholinocarbonyl)propionyl]-3-(4-thiazolyl)alanyl}amino-6-cyclohexyl-4-hydroxy-2-(1-hydroxy-1-ethylpropyl)-N-methylhexanamide;

5-{N-[2-benzyl-3-(N-benzyl-N-methylcarbamoyl)-propionyl]-3-(4-thiazolyl)alanyl}amino-6-cyclohexyl-4-hydroxy-2-(1-hydroxy-1-methylethyl)-N-methylhexanamide;

5-{N-[2-benzyl-3-(N-cyclohexyl-N-methylcarbamoyl)propionyl]-3-(4-thiazolyl)alanyl}amino-6-cyclohexyl-4-hydroxy-2-(1-hydroxy-1-methylethyl)-N-methylhexanamide;

5-{N-[2-(p-methoxybenzyl)-3-(morpholinocarbonyl)propionyl]-3-(4-thiazolyl)alanyl}amino-6-cyclohexyl-4-hydroxy-2-(1-hydroxy-1-methylethyl)-N-methylhexanamide;

5-{N-[2-(1-naphthylmethyl)-3-(morpholinocarbonyl)propionyl]-3-(4-thiazolyl)alanyl}amino-6-cyclohexyl-4-hydroxy-2-(1-hydroxycyclohexyl)-N-methylhexanamide;

and pharmaceutically acceptable salts thereof.

48. The composition of claim 46, wherein said antihypertensive agent is selected from the group consisting of:

(2S, 4S, 5S)-5-{N-[N-morpholinoacetyl-3-(1-naphthyl)-L-alanyl]-3-(4-thiazolyl)-L-alanyl}amino-6-cyclohexyl-4-hydroxy-2-(1-hydroxy-1-methylethyl)-N-[2(S)-methylbutyl]hexanamide;

(2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide;

(2S, 4S, 5S)-5-{N-[2(R)-(1-naphthylmethyl)-3-(morpholinocarbonyl)propionyl]-3-(4-thiazolyl)-L-alanyl}amino-6-cyclohexyl-4-hydroxy-2-(1-hydroxy-1-ethylpropyl)-N-methylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-butylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-[2(S)-methylbutyl]hexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-methylethyl)-N-ethylhexanamide;

(2S, 4S, 5S)-5-{N-[2(R)-benzyl-3-morpholinocarbonyl)propionyl]-3-(4-thiazolyl)-L-alanyl}amino-6-cyclohexyl-4-hydroxy-2-(1-hydroxy-1-ethylpropyl)-N-methylhexanamide;

(2S, 4S, 5S)-5-{N-[2(R)-benzyl-3-(N-benzyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-benzyl-3-(N-cyclohexyl-N-methylcarbamoyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-(p-methoxybenzyl)-3-morpholinocarbonyl)propionyl]-3-(4-thiazolyl)-L-alanyl}amino-6-cyclohexyl-4-hydroxy-2-(1-hydroxy-1-methylethyl)-N-methylhexanamide;

(2S, 4S, 5S)-5-{N-[2(R)-(1-naphthylmethyl)-3-(morpholinocarbonyl)propionyl] -3-(4-thiazolyl)-L-alanyl}amino-6-cyclohexyl-4-hydroxy-2-(1-hydroxycyclohexyl)-N-methylhexanamide;

and pharmaceutically acceptable salts thereof.

49. The compound of claim 1, selected from the group consisting of (2S, 4S, 5S)-5-{N-(2(R)-(1-naphthylmethyl)-3-(N-cyclohexyl-N-methylaminocarbonyl)propionyl)-3(4-thiazolyl)-L-alanyl}amino-4-hydroxy-2-(1-hydroxy-1-methylethyl)-7-methyl-N-(2(RS)-methylbutyl)octanamide and pharmaceutically acceptable salts thereof.

50. The compound of claim 1, selected from the group consisting of (2S, 4S, 5S)-5-{N-(2(R)-benzyl-3-(N-benzyl-N-methyl-aminocarbonyl)propionyl)-3-(4-thiazolyl)-L-alanyl}-amino-6-cyclohexyl-4-hydroxy-2-(1-hydroxy-1-methylethyl)-N-methylhexanamide and pharmaceutically acceptable salts thereof.

51. The compound of claim 1, selected from the group consisting of (2S, 4S, 5S)-5-{N-(N-morpholinoacetyl-L-phenylalanyl)-3-(4-thiazolyl)-L-alanyl}amino-6-cyclohexyl-4-hydroxy-2-(1-hydroxy-1-methylethyl)-N-(2(S)-methylbutyl)hexanamide and pharmaceutically acceptable salts thereof.

52. The compound of claim 1, selected from the group consisting of (2S, 4S, 5S)-5-{N-(N-t-butoxycarbonyl)-3-(1-naphthyl)-L-alanyl)-3-(4-thiazolyl)-L-alanyl}amino-4-hydroxy-2-(1-hydroxy-1-methylethyl)-7-methyl-N-(2(RS)-methylbutyl)octanamide and pharmaceutically acceptable salts thereof.

53. The method of claim 39, wherein said antihypertensive agent is selected from the group consisting of (2S, 4S, 5S)-5-{N-(2(R)-(1-naphthylmethyl)-3-(N-cyclohexyl-N-methylaminocarbonyl)propionyl)-3(4-thiazolyl)-L-alanyl}amino-4-hydroxy-2-(1-hydroxy-2-(1-hydroxyl-1-methylethyl)-7-methyl-N-(2(RS)-methylbutyl)octanamide;

(2S, 4S, 5S)-5-{N-(2(R)-benzyl-3-(N-benzyl-N-methylaminocarbonyl)-propionyl)-3-(4-thiazolyl)-L-alanyl}-amino-6-cyclohexyl-4-hydroxy-2-(1-hydroxy-1-methylethyl)-N-methylhexanamide;

(2S, 4S, 5S)-5-{N-(N-morpholinoacetyl-L-phenylalanyl)-3-(4-thiazolyl)-L-alanyl}amino-6-cyclohexyl-4-hydroxy-2-(1-hydroxyl-1-methylethyl)-N-(2(S)-methylbutyl)hexanamide;

(2S, 4S, 5S)-5-{N-(N-t-butoxycarbonyl)-3-(1-naphthyl)-L-alanyl)-3-(4-thiazolyl)-L-alanyl}amino-4-hydroxy-2-(1-hydroxy-1-methylethyl)-7-methyl-N-(2(RS)-methylbutyl)octanamide; and pharmaceutically acceptable salts thereof.

54. The composition of claim 46, wherein said antihypertensive agent is selected from the group consisting of (2S, 4S, 5S)-5-{N-(2(R)-(1-naphthylmethyl)-3-(N-cyclohexyl-N-methylaminocarbonyl)propionyl)-3(4-thiazolyl)-L-alanyl}amino-4-hydroxy-2-(1-hydroxy-2-(1-hydroxyl-1-methylethyl)-7-methyl-N-(2(RS)-methylbutyl)octanamide;

(2S, 4S, 5S)-5-{N-(2(R)-benzyl-3-(N-benzyl-N-methylaminocarbonyl)-propionyl)-3-(4-thiazolyl)-L-alanyl}-amino-6-cyclohexyl-4-hydroxy-2-(1-hydroxy-1-methylethyl)-N-methylhexanamide;

(2S, 4S, 5S)-5-{N-(N-morpholinoacetyl-L-phenylalanyl)-3-(4-thiazolyl)-L-alanyl}amino-6-cyclohexyl-4-hydroxy-2-(1-hydroxyl-1-methylethyl)-N-(2(S)-methylbutyl)hexanamide;

(2S, 4S, 5S)-5-{N-(N-t-butoxycarbonyl)-3-(1-naphthyl)-L-alanyl)-3-(4-thiazolyl)-L-alanyl}amino-4-hydroxy-2-(1-hydroxy-1-methylethyl)-7-methyl-N-(2(RS)-methylbutyl)octanamide; and pharmaceutically acceptable salts thereof.

55. The compound of claim 1, wherein $R^1$ is an unsubstituted morpholinyl group; a substituted morpholinyl group having methyl substituents; a thiomorpholinyl group; a 2-oxopyrrolidinyl group; a piperazinyl group; or a substituted piperazinyl group substituted by methyl, unsubstituted phenyl or phenyl substituted with methyl, methoxy or halogen atoms.

56. The compound of claim 1, wherein $R^1$ is an unsubstituted morpholinyl group.

57. The compound of claim 55, wherein $R^1$ is an substituted morpholinyl group.

* * * * *

UNITED STATES PATENT AND TRADEMARK OFFICE
CERTIFICATE OF CORRECTION

PATENT NO. : 5,364,844
DATED : November 15, 1994
INVENTOR(S) : MORISAWA et al

It is certified that error appears in the above-indentified patent and that said Letters Patent is hereby corrected as shown below:

Title page, left column, [56] References Cited, page 2, column 2, OTHER PUBLICATIONS, delete lines 15-18 (Burger, Medicinal Chemistry...601...Denkewalter ...512).

Insert -- Verderame (ed), CRC Handbook of Cardiovascular and Anti-inflamatory Agents, CRC Press Inc; Boca Raton, Florida, pp 155-156 (1986).

Burger (ed), Medicinal Chemisrty, 3rd Edition, Part II, Wiley-Interscience, N.Y., pp 1021-24, 1026, 1033 -39, 1048-52 (1970).

Bolis et al., J. Medical Chemical 30 (10), pp 1729-1737 (1987).--.

Column 2, line 48, rewrite "Selected" as --selected--.

Column 66, line 46, (Claim 39), delete "fan" and insert --an--.

Signed and Sealed this

Twenty-ninth Day of October 1996

*Attest:*

BRUCE LEHMAN

*Attesting Officer*  *Commissioner of Patents and Trademarks*